(12) United States Patent
Wai et al.

(10) Patent No.: US 7,517,532 B2
(45) Date of Patent: Apr. 14, 2009

(54) DIHYDROXYPYRIDOPYRAZINE-1,6-DIONE COMPOUNDS USEFUL AS HIV INTEGRASE INHIBITORS

(75) Inventors: John S. Wai, Harleysville, PA (US); Boyoung Kim, Lansdale, PA (US); Thorsten E. Fisher, Hatfield, PA (US); Peter D. Williams, Harleysville, PA (US); H. Marie Langford, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 630 days.

(21) Appl. No.: 10/526,275

(22) PCT Filed: Sep. 10, 2003

(86) PCT No.: PCT/US03/28366

§ 371 (c)(1),
(2), (4) Date: Mar. 1, 2005

(87) PCT Pub. No.: WO2004/024078

PCT Pub. Date: Mar. 25, 2004

(65) Prior Publication Data

US 2006/0024330 A1 Feb. 2, 2006

Related U.S. Application Data

(60) Provisional application No. 60/409,741, filed on Sep. 11, 2002.

(51) Int. Cl.
| | |
|---|---|
| A61K 39/21 | (2006.01) |
| C07D 241/00 | (2006.01) |
| C07D 241/02 | (2006.01) |
| C07D 241/36 | (2006.01) |
| C07D 471/00 | (2006.01) |
| C07D 487/00 | (2006.01) |
| C07D 491/00 | (2006.01) |
| C07D 495/00 | (2006.01) |
| C07D 497/00 | (2006.01) |

(52) U.S. Cl. .................. 424/208.1; 544/336; 544/349; 544/350

(58) Field of Classification Search .................. None
See application file for complete search history.

(56) References Cited

U.S. PATENT DOCUMENTS

| | | | |
|---|---|---|---|
| 5,294,620 | A | 3/1994 | Ratcliffe et al. |
| 5,821,241 | A | 10/1998 | Claremon et al. |
| 6,841,558 | B2 | 1/2005 | Anthony et al. |
| 2003/0055071 | A1 | 3/2003 | Anthony et al. |
| 2004/0034221 | A1 | 2/2004 | Anthony et al. |
| 2005/0010048 | A1 | 1/2005 | Zhuang et al. |
| 2005/0025774 | A1 | 2/2005 | Crescenzi et al. |
| 2005/0288293 | A1 | 12/2005 | Wai |

FOREIGN PATENT DOCUMENTS

| | | |
|---|---|---|
| WO | WO 00/00478 | 1/2000 |
| WO | WO 02/30426 A1 | 4/2002 |
| WO | WO 02/30930 A2 | 4/2002 |
| WO | WO 02/36734 A2 | 5/2002 |
| WO | WO 02/055079 A2 | 7/2002 |
| WO | WO 03/035076 A1 | 5/2003 |
| WO | WO 03/035077 A1 | 5/2003 |
| WO | WO2005/092099 | * 10/2005 |

OTHER PUBLICATIONS

Dorwald F. A. Side Reactions in Organic Synthesis, 2005, Wiley: VCH, Weinheim p. IX of Preface.*
Ratner, L., et al., "Complete Nucleotide Sequence of the AIDS Virus, HTLV-III", Nature, vol. 313, pp. 277-284, (1985).
Toh, H., et al., "Close Structural Resemblance Between Putative Polymerase of a Drosphila Transposable Genetic Element 17.6 and Pol Gene Product of Moloney Murine Leukemia Virus", EMBO Journal, vol. 4, No. 5, pp. 1267-1272, (1985).
Power, M.D., et al., "Nucleotide Sequence of SRV-1, a Type D Simian Acquired Immune Deficiency Syndrome Retrovirus", Science, vol. 231, pp. 1567-1572, (1986).

(Continued)

*Primary Examiner*—James O. Wilson
*Assistant Examiner*—Jeffrey H Murray
(74) *Attorney, Agent, or Firm*—Kenneth R. Walton; Sheldon O. Heber

(57) ABSTRACT

8,9-Dihydroxydihydropyridopyrazine-1,6-diones and 8,9-dihydroxypyridopyrazine-1,6-diones are inhibitors of HIV integrase and inhibitors of HIV replication. In one embodiment, the pyridopyrazinediones are of Formula (I): (I), wherein $R^1$, $R^2$, $R^3$, $R^4$ and $R^5$ are defined herein. The compounds are useful in the prevention and treatment of infection by HIV and in the prevention, delay in the onset, and treatment of AIDS. The compounds are employed against HIV infection and AIDS as compounds per se or in the form of pharmaceutically acceptable salts. The compounds and their salts can be employed as ingredients in pharmaceutical compositions, optionally in combination with other antivirals, immunomodulators, antibiotics or vaccines. Methods of preventing, treating or delaying the onset of AIDS and methods of preventing or treating infection by HIV are described.

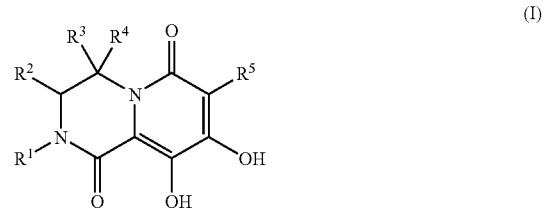

(I)

17 Claims, No Drawings

OTHER PUBLICATIONS

Pearl, L.H., et al., "A Structural Model for the Retroviral Proteases", Nature, vol. 329, pp. 351-354, (1987).

Chemical Abstract No. 33-2525, Abstract of Otiai, et al., "Synthesis of 2,5 napthyridine derivatives. II", J. Pharm. Soc. Japan, vol. 58, pp. 764-770 (1938).

Wai et al., U.S. Appl. No. 10/526,280, Notice of Allowance dated Apr. 4, 2008.

Wai et al., U.S. Appl. No. 10/526,280, Amendment dated Feb. 27, 2008.

Wai et al., U.S. Appl. No. 10/526,280, Office Action dated Nov. 28, 2007.

* cited by examiner

DIHYDROXYPYRIDOPYRAZINE-1,6-DIONE COMPOUNDS USEFUL AS HIV INTEGRASE INHIBITORS

This application is the National Stage of International Application No. PCT/US2003/028366, filed on Sep. 10, 2003, which claims the benefit of U.S. Provisional Application No. 60/409,741, filed Sep. 11, 2002, the disclosure of which is hereby incorporated by reference in its entirety.

FIELD OF THE INVENTION

The present invention is directed to dihydroxypyridopyrazine-1,6-diones and pharmaceutically acceptable salts thereof, their synthesis, and their use as inhibitors of the HIV integrase enzyme. The compounds of the present invention and their pharmaceutically acceptable salts are useful for preventing or treating infection by HIV and for treating, delaying the onset of, or preventing AIDS.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner et al., *Nature* 1985, 313: 277]. Amino acid sequence homology provides evidence that the pol sequence encodes reverse transcriptase, integrase and an HIV protease [Toh et al., *EMBO J.* 1985, 4: 1267; Power et al., *Science* 1986, 231: 1567; Pearl et al., *Nature* 1987, 329: 351]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhbitors such as indinavir and nelfinavir. The compounds of this invention are inhibitors of HIV integrase and inhibitors of HIV replication. The inhibition of integrase in vitro and of HIV replication in cells is a direct result of inhibiting the strand transfer reaction catalyzed by the recombinant integrase in vitro in HIV infected cells. A particular advantage of the present invention is highly specific inhibition of HIV integrase and HIV replication.

The following references are of interest as background:

Chemical Abstracts No. 33-2525 discloses the preparation of 5-chloro-8-hydroxy-1,6-naphthyridine-7-carboxylic acid amide from the corresponding methyl ester.

U.S. Pat. No. 5,294,620 discloses certain 1,6-naphthyridin-2-one derivatives having angiotensin II antagonist activity.

US 2003/0055071 (Publication of U.S. application Ser. No. 09/973,853, filed Oct. 10, 2001) and WO 02/30930 (Publication of International Application No. PCT/US 01/31456, filed Oct. 9, 2001) each disclose certain 8-hydroxy-1,6-naphthyridine-7-carboxamides as HIV integrase inhibitors, wherein the carboxamido nitrogen is directly or indirectly attached to phenyl or phenyl fused to a carbocycle. The carboxamides are disclosed to be useful, inter alia, for treating HIV infection and AIDS. WO 02/30426 discloses another group of 8-hydroxy-1,6-naphthyridine-7-carboxamides as HIV integrase inhibitors, wherein the carboxamido nitrogen is directly or indirectly attached to a heterocycle. WO 02/055079 discloses still another group of 8-hydroxy-1,6-naphthyridine-7-carboxamides as HIV integrase inhibitors, wherein the carboxamido nitrogen is part of a heterocyclic ring system.

WO 02/036734 discloses certain aza- and polyaza-naphthalenyl ketones to be HIV integrase inhbitors. The ketones include certain 1-aryl-1-(poly)azanaphthylenyl methanones and 1-heterocyclyl-1-(poly)azanaphthylenyl methanones. Quinolinyl, naphthyridinyl, and quinoxalinyl are disclosed as suitable (poly)azanaphthalenyl groups in the ketones.

WO 03/35076 discloses certain 5,6-dihydroxypyrimidine-4-carboxamides as HIV integrase inhibitors, and WO 03/35077 discloses certain N-substituted 5-hydroxy-6-oxo-1,6-dihydropyrimidine-4-carboxamides as HIV integrase inhibitors.

SUMMARY OF THE INVENTION

The present invention is directed to novel dihydroxypyridopyrazine-1,6-diones. These compounds and their pharmaceutically acceptable salts are useful in the inhibition of HIV integrase, the prevention of infection by HIV, the treatment of infection by HIV and in the prevention, treatment, and delay in the onset of AIDS, either as compounds or their pharmaceutically acceptable salts, or as pharmaceutical composition ingredients, whether or not in combination with other HIV/AIDS antivirals, anti-infectives, immunomodulators, antibiotics or vaccines. More particularly, the present invention includes a compound of Formula (I), or a pharmaceutically acceptable salt thereof:

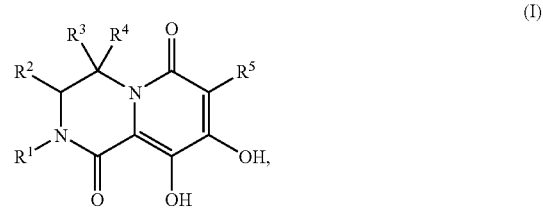

wherein

R¹ is $C_{1-6}$ alkyl which is substituted with 1 or 2 substituents each of which is independently:
  (1) $C_{3-8}$ cycloalkyl,
  (2) aryl,
  (3) a 5- or 6-membered saturated or mono-unsaturated heterocyclic ring containing from 1 to 4 heteroatoms independently selected from N, O and S,
  (4) a 5- or 6-membered heteroaromatic ring containing from 1 to 4 heteroatoms independently selected from N, O and S, or (5) a 9- or 10-membered fused bicyclic heterocycle containing from 1 to 4 heteroatoms independently selected from N, O and S, wherein at least one of the rings is aromatic;

wherein (A) each cycloalkyl is optionally substituted with from 1 to 3 substituents, each of which is independently halo, —$C_{1-6}$ alkyl, or —O—$C_{1-6}$ alkyl;

(B) each aryl is optionally substituted with from 1 to 5 substituents each of which is independently
  (1) —$C_{1-6}$ alkyl, optionally substituted with from 1 to 3 substituents each of which is independently —OH, —O—$C_{1-6}$ alkyl, —O—$C_{1-6}$ haloalkyl, —CN, —NO$_2$, —N(R$^a$R$^b$), —C(=O)N(R$^a$R$^b$), —C(=O)R$^a$, —CO$_2$R$^c$, —S(O)$_n$R$^c$, —SO$_2$N(R$^a$R$^b$), —N(R$^a$)C(=O)R$^b$, —N(R$^a$)CO$_2$R$^c$, —N(R$^a$)SO$_2$R$^c$, —N(R$^a$)SO$_2$N(R$^a$R$^b$), —OC(=O)N(R$^a$R$^b$), or —N(R$^a$)C(=O)N(R$^a$R$^b$),
  (2) —O—$C_{1-6}$ alkyl, optionally substituted with from 1 to 3 substituents each of which is independently —OH, —O—$C_{1-6}$ alkyl, —O—$C_{1-6}$ haloalkyl, —S(O)$_n$R$^c$, —C(=O)N(R$^a$R$^b$), —SO$_2$N(R$^a$R$^b$), —N(R$^a$)C(=O)R$^b$, —N(R$^a$)CO$_2$R$^c$, —N(R$^a$)SO$_2$R$^c$, —N(R$^a$)SO$_2$N(R$^a$R$^b$), —OC(=O)N(R$^a$R$^b$), or —N(R$^a$)C(=O)N(R$^a$R$^b$),
  (3) —$C_{1-6}$ haloalkyl,
  (4) —O—$C_{1-6}$ haloalkyl,
  (5) —OH,
  (6) halo,
  (7) —CN,
  (8) —NO$_2$,
  (9) —N(R$^a$R$^b$),
  (10) —C(=O)N(R$^a$R$^b$),
  (11) —C(=O)R$^a$,
  (12) —CO$_2$R$^c$,
  (13) —SR$^c$,
  (14) —S(=O)R$^c$,
  (15) —SO$_2$R$^c$,
  (16) —N(R$^a$)SO$_2$R$^c$,
  (17) —SO$_2$N(R$^a$R$^b$),
  (18) —N(R$^a$)C(=O)R$^b$,
  (19) —N(R$^a$)CO$_2$R$^c$, or
  (20) phenyl;

(C) each saturated or mono-unsaturated heterocyclic ring is
  (i) optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and
  (ii) optionally substituted with 1 or 2 substituents each of which is independently aryl or a 5- or 6-membered heteroaromatic ring containing from 1 to 4 heteroatoms independently selected from N, O and S; and (D) each heteroaromatic ring or each fused bicyclic heterocycle is
  (i) optionally substituted with from 1 to 7 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and
  (ii) optionally substituted with 1 or 2 substituents each of which is independently aryl or —$C_{1-6}$ alkyl-aryl;

$R^2$ is —H or —$C_{1-6}$ alkyl;

$R^3$ is —H, —$C_{1-6}$ alkyl, —$C_{1-6}$ haloalkyl, or —$C_{1-6}$ alkyl substituted with one of —OH, —O—$C_{1-6}$ alkyl, —O—$C_{1-6}$ haloalkyl, —CN, —NO$_2$, —N(R$^a$R$^b$), —C(=O)N(R$^a$R$^b$), —C(=O)R$^a$, —CO$_2$R$^c$, —S(O)$_n$R$^c$, —SO$_2$N(R$^a$R$^b$), —N(R$^a$)C(=O)R$^b$, —N(R$^a$)CO$_2$R$^c$, —N(R$^a$)SO$_2$R$^c$, —N(R$^a$)SO$_2$N(R$^a$R$^b$), —OC(=O)N(R$^a$R$^b$), or —N(R$^a$)C(=O)N(R$^a$R$^b$);

$R^4$ is:
  (1) —H,
  (2) —$C_{1-6}$ alkyl optionally substituted with one of —OH, —O—$C_{1-6}$ alkyl, —O—$C_{1-6}$ haloalkyl, —CN, —NO$_2$, —N(R$^a$R$^b$), —C(=O)N(R$^a$R$^b$), —C(=O)R$^a$, —CO$_2$R$^c$, —S(O)$_n$R$^c$, —SO$_2$N(R$^a$R$^b$), —N(R$^a$)—C(R$^b$)=O, —N(R$^a$)SO$_2$R$^c$, —N(R$^a$)SO$_2$N(R$^a$R$^b$), —OC(=O)N(R$^a$R$^b$), —N(R$^a$)C(=O)N(R$^a$R$^b$), —O—$C_{1-6}$ alkyl-C(=O)N(R$^a$R$^b$), —S—$C_{1-6}$ alkyl-C(=O)N(R$^a$R$^b$), —N(R$^a$)—$C_{1-6}$ alkyl-C(=O)N(R$^a$R$^b$), or —N(SO$_2$R$^c$)—$C_{1-6}$ alkyl-C(=O)N(R$^a$R$^b$),
  (3) —$C_{1-6}$ haloalkyl,
  (4) —C(=O)R$^a$,
  (5) —CO$_2$R$^c$,
  (6) —C(=O)N(R$^a$R$^b$),
  (7) —SO$_2$N(R$^a$R$^b$),
  (8) —$C_{2-6}$ alkenyl,
  (9) —$C_{2-6}$ alkenyl-C(=O)—N(R$^a$)$_2$,
  (10) —$C_{2-5}$ alkynyl,
  (11) —$C_{2-5}$ alkynyl-CH$_2$N(R$^a$)$_2$,
  (12) —$C_{2-5}$ alkynyl-CH$_2$OR$^a$,
  (13) —$C_{2-5}$ alkynyl-CH$_2$S(O)$_n$R$^c$, or
  (14) —R$^k$,
  (15) —$C_{1-6}$ alkyl substituted with R$^k$,
  (16) —$C_{1-6}$ haloalkyl substituted with R$^k$,
  (17) —$C_{1-6}$ alkyl-O—R$^k$,
  (18) —$C_{1-6}$ alkyl-O—$C_{1-6}$ alkyl-R$^k$,
  (19) —$C_{1-6}$ alkyl-S(O)$_n$—R$^k$,
  (20) —$C_{1-6}$ alkyl-S(O)$_n$$C_{1-6}$ alkyl-R$^k$,
  (21) —$C_{1-6}$ alkyl-N(R$^a$)—R$^k$,
  (22) —$C_{1-6}$ alkyl-N(R$^a$)—$C_{1-6}$ alkyl-R$^k$,
  (23) —$C_{1-6}$ alkyl-N(R$^a$)—$C_{1-6}$ alkyl-OR$^k$, with the proviso that the —N(R$^a$)—moiety and the —OR$^k$ moiety are not both attached to the same carbon of the —$C_{1-6}$ alkyl-moiety,
  (24) —$C_{1-6}$ alkyl-C(=O)—R$^k$,
  (25) —$C_{1-6}$ alkyl-C(=O)N(R$^a$)—R$^k$,
  (26) —$C_{1-6}$ alkyl-N(R$^a$)C(=O)—R$^k$,
  (27) —$C_{1-6}$ alkyl-C(=O)N(R$^a$)—$C_{1-6}$ alkyl-R$^k$, or
  (28) —$C_{1-6}$ alkyl-N(R$^a$)—$C_{0-6}$ alkyl-S(O)$_n$R$^k$;

wherein R$^k$ is
  (i) aryl, which is optionally substituted with from 1 to 5 substituents each of which is independently —$C_{1-6}$ alkyl, —$C_{1-6}$ alkyl-OH, —$C_{1-6}$ alkyl-O—$C_{1-6}$ alkyl, —$C_{1-6}$ alkyl-O—$C_{1-6}$ haloalkyl, —$C_{1-6}$ alkyl-N(R$^a$R$^b$), —$C_{1-6}$ alkyl-C(=O)N(R$^a$R$^b$), —$C_{1-6}$ alkyl-C(=O)R$^a$, —$C_{1-6}$ alkyl—CO$_2$R$^c$, —$_{1-6}$ alkyl-S(O)$_n$R$^c$, —O—$C_{1-6}$ alkyl, —$C_{1-6}$ haloalkyl, —O—$C_{1-6}$ haloalkyl, —OH, halo, —N(R$^a$R$^b$), —C(=O)N(R$^a$R$^b$), —C(=O)R$^a$, —CO$_2$R$^c$, —S(O)$_n$R$^c$, or —SO$_2$N(R$^a$R$^b$);
  (ii) a 4- to 7-membered saturated or mono-unsaturated heterocyclic ring containing at least one carbon atom and from 1 to 4 heteroatoms independently selected from N, O and S, wherein the heterocyclic ring is:
    (a) optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and
    (b) optionally mono-substituted with aryl or HetA; wherein HetA is a 5- or 6-membered heteroaromatic ring containing from 1 to 4 heteroatoms independently selected from N, O and S, wherein the heteroaromatic ring is optionally fused with a benzene ring, and HetA is optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, or oxo; or (iii) a 5- or 6-membered heteroaromatic ring containing from 1 to 4 heteroatoms independently selected from N, O and S, wherein the heteroaromatic ring is optionally substituted with from optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, or oxo;

or alternatively $R^3$ and $R^4$ are joined together to form $C_{5-8}$ cycloalkyl or a 5- to 7-membered saturated heterocyclic ring containing from 1 to 4 heteroatoms independently selected from N, O and S; wherein the cycloalkyl is optionally substituted with from 1 to 3 substituents each of which is independently halo, —$C_{1-6}$ alkyl, or —O—$C_{1-6}$ alkyl; and the heterocyclic ring is optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, or oxo;

or alternatively:

(i) $R^2$ and $R^3$ together form a direct bond to give a ring double bond, and $R^4$ is an independent group as defined above;

(ii) $R^2$ and $R^3$ together with the ring carbon atoms to which they are attached form a fused cyclopropyl ring which is optionally substituted at the non-fused cyclopropyl ring carbon with —$OR^d$, and $R^4$ is —H; or (iii) $R^2$ and $R^3$ together with the ring carbon atoms to which they are attached form a fused phenyl ring or a fused pyridyl ring, and $R^4$ is absent;

$R^5$ is:
(1) —H,
(2) —$C_{1-6}$ alkyl,
(3) —$C_{1-6}$ alkyl-N($R^a R^b$),
(4) —$C_{1-6}$ alkyl-C(=O)N($R^a R^b$),
(5) —$C_{1-6}$ alkyl-C(=O)$R^a$,
(6) —$C_{1-6}$ alkyl—$CO_2 R^c$,
(7) —$C_{1-6}$ alkyl-$SR^c$,
(8) —$C_{1-6}$ alkyl—S(=O)$R^c$,
(9) —$C_{1-6}$ alkyl-$SO_2 R^c$,
(10) —$C_{1-6}$ alkyl-$SO_2$N($R^a R^b$)
(11) —$C_{1-6}$ haloalkyl,
(12) —O—$C_{1-6}$ alkyl,
(13) —O—$C_{1-6}$ haloalkyl,
(14) halo,
(15) —CN,
(16) —C(=O)$R^a$,
(17) —$CO_2 R^c$,
(18) —$SR^c$,
(19) —S(=O)$R^c$,
(20) —$SO_2 R^c$,
(21) —N($R^a R^b$),
(22) —C(=O)N($R^a R^b$), or
(23) —$SO_2$N($R^a R^b$);
(24) aryl
(25) —$C_{1-6}$ alkyl-aryl
(26) HetB,
(27) —$C_{1-6}$ alkyl-HetB,
(28) HetC, or
(29) —$C_{1-6}$ alkyl-HetC, wherein
HetB is a 5- or 6-membered saturated or mono-unsaturated ring containing from 1 to 4 heteroatoms independently selected from N, O and S, wherein the ring is optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, oxo, —C(=O)—$C_{1-6}$ alkyl, —C(=O)—$C_{1-6}$ haloalkyl, or —$C_{1-6}$ alkyl-$C_{3-8}$ cycloalkyl; and HetC is a 5- or 6-membered heteroaromatic ring containing from 1 to 4 heteroatoms independently selected from N, O and S, wherein the heteroaromatic ring is optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, or oxo;

each $R^a$ and $R^b$ is independently —H or —$C_{1-6}$ alkyl;
each $R^c$ is independently a —$C_{1-6}$ alkyl;
$R^d$ is a —$C_{1-6}$ alkyl, allyl, or benzyl; and
each n is independently an integer equal to 0, 1 or 2.

An aspect of the present invention is a compound of Formula (I) as defined above, except that: in the definition of $R^1$, the optional substitution on each aryl is restricted to 1 to 5 substituents each of which is independently one of groups (1) to (19) (i.e., the choice of optional substituents on aryl does not include phenyl); in the alternative definitions of $R^2$ and $R^3$, $R^2$ and $R^3$ are restricted to definition (i) (i.e., the formation of a ring double bond; the joining of $R^2$ and $R^3$ to form a fused cyclopropyl ring, a fused phenyl ring, or a fused pyridyl ring is excluded); and in the definition of HetB in $R^5$, the optional substitution on the saturated or mono-unsaturated ring is restricted to 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo.

The present invention also includes pharmaceutical compositions containing a compound of the present invention and methods of preparing such pharmaceutical compositions. The present invention further includes methods of treating AIDS, methods of delaying the onset of AIDS, methods of preventing AIDS, methods of preventing infection by HIV, and methods of treating infection by HIV.

Other embodiments, aspects and features of the present invention are either further described in or will be apparent from the ensuing description, examples and appended claims.

DETAILED DESCRIPTION OF THE INVENTION

The present invention includes the dihydroxypyridopyrazine-1,6-diones of Formula (I) above. These compounds and pharmaceutically acceptable salts thereof are HIV integrase inhibitors.

A first embodiment of the present invention is a compound of Formula (I), or a pharmaceutically acceptable salt thereof, wherein $R^1$ is -$C_{1-4}$ alkyl mono-substituted with aryl; wherein the aryl is optionally substituted with from 1 to 4 substituents each of which is independently (1) —$C_{1-4}$ alkyl, optionally mono-substituted with —OH, —O—$C_{1-4}$ alkyl, —O—$C_{1-4}$ haloalkyl, —CN, —N($R^a R^b$), —C(=O)N($R^a R^b$), —C(=O)$R^a$, —$CO_2 R^c$, —S(O)$_n R^c$, —$SO_2$N($R^a R^b$), —N($R^a$)C(=O) $R^b$, —N($R^a$) $CO_2 R^c$, —N($R^a$)$SO_2 R^c$, —N($R^a$)$SO_2$N ($R^a R^b$), —OC(=O)N($R^a R^b$), or —N($R^a$)C(=O)N ($R^a R^b$), (2) —O—$C_{1-4}$ alkyl, optionally mono-substituted with —OH, —O—$C_{1-4}$ alkyl, —O—$C_{1-4}$ haloalkyl, —S(O)$_n R^c$, —N($R^a$)—$CO_2 R^c$, —C(=O)N($R^a R^b$), —SO$_2$N(R$^a$R$^b$), —N(R$^a$)C(=O)R$^b$, —N(R$^a$)CO$_2$R$^c$, —N(R$^a$)SO$_2$R$^c$, —N(R$^a$)SO$_2$N(R$^a$R$^b$), —OC(=O)N(R$^a$R$^b$), or —N(R$^a$)C(=O)N(R$^a$R$^b$), (3) —C$_{1-4}$ haloalkyl,
(4) —O—C$_{1-4}$ haloalkyl,
(5) —OH,
(6) halo,
(7) —CN,
(8) —NO$_2$,
(9) —N(R$^a$R$^b$),
(10) —SR$^c$,
(11) —S(=O)R$^c$,
(12) —SO$_2$R$^c$,
(13) —N(R$^a$)SO$_2$R$^c$,
(14) —SO$_2$N(R$^a$R$^b$),
(15) —N(R$^a$)C(=O)R$^b$,
(16) —N(R$^a$)CO$_2$R$^c$, or
(17) phenyl;

and all other variables are as originally defined above.

In an aspect of the first embodiment, each of the optional substituents on the aryl is independently one of the groups (1) to (16) set forth above (i.e., phenyl is excluded as a possible optional substituent).

A second embodiment of the present invention is a compound of Formula (I), or a pharmaceutically acceptable salt thereof, wherein R$^1$ is —(CH$_2$)$_{1-4}$-phenyl, wherein the phenyl is optionally substituted with from 1 to 3 substituents each of which is independently (1) —C$_{1-4}$ alkyl, optionally mono-substituted with —OH, —O—C$_{1-4}$ alkyl, —O—C$_{1-4}$ haloalkyl, —CN, —N(R$^a$R$^b$), —C(=O)N(R$^a$R$^b$), —C(=O)R$^a$, —CO$_2$R$^c$, —S(O)$_n$R$^c$, or —SO$_2$N(R$^a$R$^b$),
(2) —O—C$_{1-4}$ alkyl,
(3) —C$_{1-4}$ haloalkyl,
(4) —O—C$_{1-4}$ haloalkyl,
(5) —OH,
(6) halo,
(7) —CN,
(8) —NO$_2$,
(9) —N(R$^a$R$^b$),
(10) —SR$^c$,
(11) —S(=O)R$^c$,
(12) —SO$_2$R$^c$,
(13) —N(R$^a$)SO$_2$R$^c$,
(14) —SO$_2$N(R$^a$R$^b$),
(15) —N(R$^a$)C(=O)R$^b$,
(16) —N(R$^a$)CO$_2$R$^c$, or
(17) phenyl;

and all other variables are as originally defined above.

In an aspect of the second embodiment, each of the optional substituents on the phenyl is independently one of the groups (1) to (16) set forth above (i.e., phenyl is excluded as a possible optional substituent).

A third embodiment of the present invention is a compound of Formula (I), or a pharmaceutically acceptable salt thereof, wherein R$^1$ is

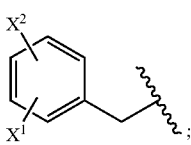

wherein X$^1$ and X$^2$ are each independently
(1) —H,
(2) methyl,
(3) ethyl,
(4) methoxy,
(5) ethoxy,
(6) —CF$_3$,
(7) fluoro,
(8) bromo, or
(9) chloro,
(10) —CN,
(11) —S—CH$_3$, or
(12) phenyl;

and all other variables are as originally defined above.

In an aspect of the third embodiment, X$^1$ and X$^2$ are each independently selected from one of groups (1) to (9) set forth above (i.e., —CN, —S—CH$_3$, and phenyl are each excluded as possible substituents).

In another aspect of the third embodiment, R$^1$ is 4-fluorobenzyl.

A fourth embodiment of the present invention is a compound of Formula (I), or a pharmaceutically acceptable salt thereof, wherein R$^2$ is —H or —C$_{1-4}$ alkyl; and all other variables are as originally defined or as defined in any of the preceding embodiments or aspects. In an aspect of this embodiment, R$^2$ is —H.

A fifth embodiment of the present invention is a compound of Formula (I), or a pharmaceutically acceptable salt thereof, wherein R$^3$ is —H or —C$_{1-4}$ alkyl; and all other variables are as originally defined or as defined in any of the preceding embodiments or aspects thereof. In an aspect of this embodiment, R$^3$ is —H.

A sixth embodiment of the present invention is a compound of Formula (I), or a pharmaceutically acceptable salt thereof, wherein R$^4$ is:
(1) —H,
(2) —C$_{1-4}$ alkyl optionally substituted with one of —OH, —O—C$_{1-4}$ alkyl, —O—C$_{1-4}$ haloalkyl, —CN, —N(R$^a$R$^b$), —C(=O)N(R$^a$R$^b$), —C(=O)R$^a$, —CO$_2$R$^c$, —S(O)$_n$R$^c$, —SO$_2$N(R$^a$R$^b$), —N(R$^a$)—C(R$^b$)=O, —N(R$^a$)SO$_2$R$^b$, or —N(R$^a$)SO$_2$N(R$^a$R$^b$),
(3) —C(=O)N(R$^a$R$^b$),
(4) —R$^k$,
(5) —C$_{1-4}$ alkyl substituted with R$^k$,
(6) —C$_{1-4}$ alkyl-O—R$^k$, or
(7) —C$_{1-4}$ alkyl-O—C$_{1-4}$ alkyl-R$^k$;

and all other variables are as originally defined or as defined in any of the preceding embodiments or aspects thereof.

A seventh embodiment of the present invention is a compound of Formula (I), or a pharmaceutically acceptable salt thereof, wherein R$^4$ is:
(1) —H,
(2) —C$_{1-4}$ alkyl optionally substituted with one of —OH, —N(R$^a$R$^b$), or —C(=O)N(R$^a$R$^b$),
(3) —C(=O)N(R$^a$R$^b$),
(4) —(CH$_2$)$_{1-3}$—R$^k$,
(5) —(CH$_2$)$_{1-3}$—O—R$^k$, or
(6) —(CH$_2$)$_{1-3}$—O—(CH$_2$)$_{1-3}$—R$^k$;

and all other variables are as originally defined or as defined in any of the first five embodiments or aspects thereof.

An eighth embodiment of the present invention is a compound of Formula (I), or a pharmaceutically acceptable salt thereof, wherein $R^k$ is:
(i) phenyl, which is optionally substituted with from 1 to 3 substituents each of which is independently —$C_{1-4}$ alkyl, —$C_{1-4}$ alkyl-OH, —$C_{1-4}$ alkyl-O—$C_{1-4}$ alkyl, —$C_{1-4}$ alkyl-O—$C_{1-4}$ haloalkyl, —$C_{1-4}$ alkyl-N($R^aR^b$), —$C_{1-4}$ alkyl-C(=O)N($R^aR^b$), —$C_{1-4}$ alkyl-C(=O)$R^a$, —$C_{1-4}$ alkyl-CO$_2R^c$, —$C_{1-4}$ alkyl—S(O)$_nR^c$, —O—$C_{1-4}$ alkyl, —$C_{1-4}$ haloalkyl, —O—$C_{1-4}$ haloalkyl, —OH, halo, —N($R^aR^b$), —C(=O)N($R^aR^b$), —C(=O)$R^a$, —CO$_2R^c$, —S(O)$_nR^c$, or —SO$_2$N($R^aR^b$);
(ii) a 4- to 7-membered saturated heterocyclic ring containing at least one carbon atom and a total of from 1 to 4 heteroatoms independently selected from 1 to 4 N atoms, from 0 to 2 O atoms, and from 0 to 2 S atoms, wherein the heterocyclic ring is:
   (a) optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, or oxo; and
   (b) optionally mono-substituted with phenyl or HetA;
      wherein HetA is a 5- or 6-membered heteroaromatic ring containing a total of from 1 to 4 heteroatoms independently selected from 1 to 4 N atoms, from 0 to 2 O atoms, and from 0 to 2 S atoms, wherein HetA is optionally substituted with from 1 to 3 substituents each of which is independently —$C_{1-4}$ alkyl, —$C_{1-4}$ haloalkyl, —O—$C_{1-4}$ alkyl, —O—$C_{1-4}$ haloalkyl, or oxo; or
(iii) a 5- or 6-membered heteroaromatic ring containing a total of from 1 to 4 heteroatoms independently selected from 1 to 4 N atoms, from 0 to 2 O atoms, and from 0 to 2 S atoms, wherein the heteroaromatic ring is optionally substituted with from optionally substituted with from 1 to 3 substituents each of which is independently —$C_{1-6}$ alkyl, —$C_{1-6}$ haloalkyl, —O—$C_{1-6}$ alkyl, —O—$C_{1-6}$ haloalkyl, or oxo;

and all other variables are as originally defined or as defined in any of the preceding embodiments or aspects thereof.

In an aspect of the eighth embodiment, HetA is a 5- or 6-membered heteroaromatic ring containing 1 or 2 N atoms, wherein HetA is optionally substituted with from 1 to 3 substituents each of which is independently —$C_{1-4}$ alkyl, —$C_{1-4}$ haloalkyl, —O—$C_{1-4}$ alkyl, —O—$C_{1-4}$ haloalkyl, or oxo. In another aspect of the eighth embodiment, HetA is pyrrolyl, pyrazolyl, imidazolyl, pyridyl, or pyrazinyl; which is optionally substituted with from 1 to 3 substituents each of which is independently —$C_{1-4}$ alkyl (e.g., methyl), —$C_{1-4}$ haloalkyl (e.g., trifluoromethyl), —O—$C_{1-4}$ alkyl (e.g., methoxy), —O—$C_{1-4}$ haloalkyl (e.g., —OCF$_3$), or oxo.

A ninth embodiment of the present invention is a compound of Formula (I), or a pharmaceutically acceptable salt thereof, wherein $R^k$ is:
(i) phenyl, which is optionally substituted with from 1 to 3 substituents each of which is independently —$C_{1-4}$ alkyl, —$C_{1-4}$ alkyl-OH, —$C_{1-4}$ alkyl-O—$C_{1-4}$ alkyl, —$C_{1-4}$ alkyl-O—$C_{1-4}$ haloalkyl, —$C_{1-4}$ alkyl-N($R^aR^b$), —$C_{1-4}$ alkyl-C(=O)N($R^aR^b$), —$C_{1-4}$ alkyl-C(=O)$R^a$, —$C_{1-4}$ alkyl-CO$_2R^c$, —$C_{1-4}$ alkyl—S(O)$_nR^c$, —O—$C_{1-4}$ alkyl, —$C_{1-4}$ haloalkyl, —O—$C_{1-4}$ haloalkyl, —OH, halo, —N($R^aR^b$), —C(=O)N($R^aR^b$), —C(=O)$R^a$, —CO$_2R^c$, —S(O)$_nR^c$, or —SO$_2$N($R^aR^b$); or
(ii) a saturated heterocyclic ring selected from the group consisting of piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, and dioxanyl; wherein the saturated heterocyclic ring is:
   (a) optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, or oxo; and
   (b) optionally mono-substituted with phenyl or HetA;
wherein HetA is a heteroaromatic ring selected from the group consisting of pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl; wherein the heteroaromatic ring is optionally substituted with from 1 to 3 substituents each of which is independently —$C_{1-4}$ alkyl, —$C_{1-4}$ haloalkyl, —O—$C_{1-4}$ alkyl, —O—$C_{1-4}$ haloalkyl, or oxo;

and all other variables are as originally defined or as defined in any of the first seven embodiments or aspects thereof.

A tenth embodiment of the present invention is a compound of Formula (I), or a pharmaceutically acceptable salt thereof, wherein $R^5$ is:
(1) —H,
(2) —$C_{1-4}$ alkyl,
(3) —$C_{1-4}$ alkyl-N($R^aR^b$),
(4) —$C_{1-4}$ alkyl-C(=O)N($R^aR^b$),
(5) —$C_{1-4}$ alkyl-SO$_2$N($R^aR^b$)
(6) —$C_{1-4}$ haloalkyl,
(7) halo,
(8) —CN,
(9) aryl
(10) —$C_{1-4}$ alkyl-aryl
(11) HetB,
(12) —$C_{1-4}$ alkyl-HetB,
(13) HetC, or
(14) —$C_{1-4}$ alkyl-HetC,
wherein
   HetB is a 5- or 6-membered saturated ring containing a total of from 1 to 4 heteroatoms independently selected from 1 to 4 N atoms, from 0 to 2 O atoms, and from 0 to 2 S atoms, wherein the saturated ring is optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, oxo, —C(=O)—$C_{1-4}$ alkyl, —C(=O)—$C_{1-4}$ haloalkyl, or —$C_{1-4}$ alkyl-$C_{3-6}$ cycloalkyl; and
   HetC is a 5- or 6-membered heteroaromatic ring containing a total of from 1 to 4 heteroatoms independently selected from 1 to 4 N atoms, from 0 to 2 O atoms, and from 0 to 2 S atoms, wherein the heteroaromatic ring is optionally substituted with from 1 to 3 substituents each of which is independently —$C_{1-4}$ alkyl, —$C_{1-4}$ haloalkyl, —O—$C_{1-4}$ alkyl, —O—$C_{1-4}$ haloalkyl, or oxo;

and all other variables are as originally defined or as defined in any of the preceding embodiments or aspects thereof.

In an aspect of the tenth embodiment, in the definition of HetB, the optional substitution on the saturated ring is restricted to 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, or oxo.

An eleventh embodiment of the present invention is a compound of Formula (I), or a pharmaceutically acceptable salt thereof, wherein $R^5$ is:
(1) —H,
(2) —$C_{1-4}$ allyl,
(3) —$C_{1-4}$ alkyl-N($R^aR^b$),
(4) halo,
(5) —CN, or
(6) —$C_{1-4}$ alkyl-HetB;
wherein
HetB is a 5- or 6-membered saturated ring containing 1 or 2 N atoms and carbon atoms, wherein the saturated ring is optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, oxo, —C(=O)—$C_{1-4}$ alkyl, —C(=O)—$C_{1-4}$ haloalkyl, or —$C_{1-4}$ alkyl-$C_{3-6}$ cycloalkyl;
and all other variables are as originally defined or as defined in any of the first nine embodiments or aspects thereof.

In an aspect of the eleventh, in the definition of HetB, the optional substitution on the saturated ring is restricted to 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, or oxo.

In another aspect of the eleventh embodiment, HetB is pyrrolidinyl, pyrazolidinyl, imidazolidinyl, piperidinyl, or piperazinyl, which is optionally substituted with from 1 to 4 substituents each of which is independently halogen (e.g., fluoro, chloro, or bromo), —$C_{1-4}$ alkyl (e.g., methyl), —$C_{1-4}$ haloalkyl (e.g., trifluoromethyl), —O—$C_{1-4}$ alkyl (e.g., methoxy), —O—$C_{1-4}$ haloalkyl (e.g., —$OCF_3$), or oxo.

Other embodiments of the present invention include compounds of Formula (I), wherein each $R^a$ and $R^b$ is independently —H or —$C_{1-4}$ alkyl; each $R^c$ is independently a —$C_{1-4}$ alkyl; and all other variables are as originally defined or as defined in any of the foregoing embodiments or aspects thereof.

Still other embodiments of the present invention include compounds of Formula (I), wherein each $R^a$ and $R^b$ is independently —H, methyl, or ethyl; each $R^c$ is independently methyl or ethyl; and all other variables are as originally defined or as defined in any of the foregoing embodiments or aspects thereof.

Still other embodiments of the present invention include compounds of Formula (I), wherein $R^d$ is a —$C_{1-4}$ alkyl (e.g., methyl, ethyl or n-propyl), allyl, or benzyl; and all other variables are as originally defined or as defined in any of the foregoing embodiments or aspects thereof.

A class of the present invention includes compounds of Formula (II), or a pharmaceutically acceptable salt thereof:

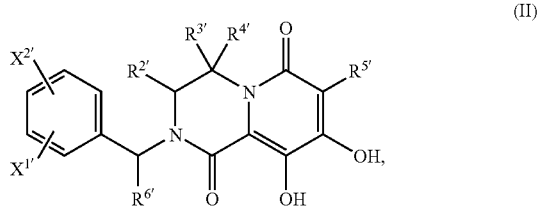

(II)

wherein:
$X^{1'}$ and $X^{2'}$ are each independently:
(1) —H,
(2) $C_{1-4}$ alkyl,
(2) —O—$C_{1-4}$ alkyl,
(3) —$C_{1-4}$ haloalkyl,
(4) —O—$C_{1-4}$ haloalkyl,
(5) halo,
(6) —CN,
(7) —S—$C_{1-4}$ alkyl, or
(8) phenyl;
$R^{2'}$ is —H or —$C_{1-4}$ alkyl;
$R^{3'}$ is —H or —$C_{1-4}$ alkyl;
$R^{4'}$ is:
(1) —H,
(2) —$C_{1-4}$ alkyl optionally substituted with one of —OH, —N($R^{a'}R^{b'}$), or —C(=O)N($R^{a'}R^{b'}$),
(3) —C(=O)N($R^{a'}R^{b'}$),
(4) —$(CH_2)_{1-3}$—$R^{k'}$,
(5) —$(CH_2)_{1-3}$—O—$R^{k'}$, or
(6) —$(CH_2)_{1-3}$—O—$(CH_2)_{1-3}$—$R^{k'}$;
wherein $R^{k'}$ is:
(i) phenyl, which is optionally substituted with from 1 to 3 substituents each of which is independently —$C_{1-4}$ alkyl, —O—$C_{1-4}$ alkyl, —$C_{1-4}$ haloalkyl, —O—$C_{1-4}$ haloalkyl, or halo; or
(ii) HetD, wherein HetD is a 5- or 6-membered saturated ring containing 1 or 2 N atoms, 0 or 1 S atoms, and a balance of carbon atoms, wherein the saturated ring is optionally substituted with from 1 to 4 substituents each of which is independently halo, —$C_{1-4}$ alkyl, —$C_{1-4}$ haloalkyl, —O—$C_{1-4}$ alkyl, —O—$C_{1-4}$ haloalkyl, or oxo;

or alternatively:
(i) $R^{2'}$ and $R^{3'}$ together form a direct bond to give a ring double bond, and $R^{4'}$ is an independent group as defined above;
(ii) $R^{2'}$ and $R^{3'}$ together with the ring carbon atoms to which they are attached form a fused cyclopropyl ring which is optionally substituted at the non-fused cyclopropyl ring carbon with —$OR^{d'}$, and $R^{4'}$ is —H; or
(iii) $R^{2'}$ and $R^{3'}$ together with the ring carbon atoms to which they are attached form a fused phenyl ring or a fused pyridyl ring, and $R^{4'}$ is absent;
$R^{5'}$ is:
(1) —H,
(2) —$C_{1-4}$ alkyl,
(3) —$C_{1-4}$ alkyl-N($R^{a'}R^{b'}$),
(4) halo,
(5) —CN, or
(6) —$(CH_2)_{1-3}$-HetB;
wherein
HetB is a 5- or 6-membered saturated ring containing 1 or 2 N atoms, zero or 1 O atom, zero or 1 S atom, and a balance of carbon atoms, wherein the saturated ring is optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, oxo, —C(=O)—$C_{1-4}$ alkyl, —C(=O)—$C_{1-4}$ haloalkyl, or —$C_{1-4}$ alkyl-$C_{3-6}$ cycloalkyl;
$R^6$ is —H or methyl;
each $R^{a'}$ and $R^{b'}$ is independently —H or —$C_{1-4}$ alkyl; and
$R^{d'}$ is —$C_{1-4}$ alkyl, allyl, or benzyl.

A sub-class of the present invention includes compounds of Formula (II), or a pharmaceutically acceptable salt thereof, wherein:

wherein $X^{1'}$ and $X^{2'}$ are each independently:
(1) —H,
(2) methyl,
(2) —OCH$_3$,
(3) —CF$_3$,
(4) —O—CF$_3$,
(5) chloro,
(6) fluoro,
(7) bromo;
(6) —CN,
(7) —S—CH$_3$, or
(8) phenyl;

$R^{2'}$ is —H or methyl;
$R^{3'}$ is —H or methyl;
$R^{4'}$ is:
(1) —H,
(2) methyl,
(3) —CH$_2$OH,
(3) —C(=O)N(CH$_3$)$_2$,
(4) —CH$_2$—R$^{k_1}$, or
(5) —CH$_2$—O—CH$_2$—R$^{k_1}$;
  wherein R$^{k_1}$ is:
  (i) phenyl, which is optionally substituted with from 1 to 3 substituents each of which is independently —CH$_3$, —OCH$_3$, —CF$_3$, —OCF$_3$, chloro, bromo or fluoro; or
  (ii) HetD, wherein HetD is a 5- or 6-membered saturated ring containing 1 or 2 N atoms, 0 or 1 S atoms, and a balance of carbon atoms, wherein the saturated ring is optionally substituted with from 1 to 4 substituents each of which is independently chloro, bromo, fluoro, —CH$_3$, —CF$_3$, —OCH$_3$, —OCF$_3$, or oxo;

or alternatively:
(i) $R^{2'}$ and $R^{3'}$ together form a direct bond to give a ring double bond, and $R^{4'}$ is an independent group as defined above;
(ii) $R^{2'}$ and $R^{3'}$ together with the ring carbon atoms to which they are attached form a fused cyclopropyl ring which is optionally substituted at the non-fused cyclopropyl ring carbon with —OMe, —OEt, —O-allyl, or —O-benzyl, and $R^{4'}$ is —H; or
(iii) $R^{2'}$ and $R^{3'}$ together with the ring carbon atoms to which they are attached form a fused phenyl ring or a fused pyridyl ring, and $R^{4'}$ is absent;

$R^5$ is:
(1) —H,
(2) methyl,
(3) —(CH$_2$)$_{1-2}$—N(CH$_3$)$_2$,
(4) fluoro,
(5) bromo,
(6) iodo,
(7) —CN, or
(8) —CH$_2$-HetB;
  wherein
    HetB is a 5- or 6-membered saturated ring containing 1 or 2 N atoms, zero or 1 O atom, zero or 1 S atom, and a balance of carbon atoms, wherein the saturated ring is optionally substituted with from 1 to 4 substituents each of which is independently chloro, bromo, fluoro, —CH$_3$, —CF$_3$, —OCH$_3$, —OCF$_3$, oxo, —C(=O)—CH$_3$, —C(=O)—CF$_3$, or —CH$_2$-cyclopropyl; and
$R^6$ is —H or methyl.

In an aspect of the preceding sub-class, $R^{2'}$ and $R^{3'}$ are each —H or methyl, with the proviso that $R^{2'}$ and $R^{3'}$ are not both methyl; or alternatively $R^{2'}$ and $R^{3'}$ together form a direct bond to give a ring double bond, with the proviso that when $R^{2'}$ and $R^{3'}$ together form a direct bond, $R^{4'}$ is —H.

In another aspect of the preceding sub-class, HetB is pyrrolidinyl, pyrazolidinyl, imidazolidinyl, piperidinyl, piperazinyl, morpholinyl, or thiomorpholinyl, which is optionally substituted with from 1 to 4 substituents each of which is independently chloro, bromo, fluoro, —CH$_3$, —CF$_3$, —OCH$_3$, —OCF$_3$, oxo, —C(=O)—CH$_3$, —C(=O)—CF$_3$, or —CH$_2$-cyclopropyl.

Another sub-class of the present invention includes compounds of Formula (IIa), or a pharmaceutically acceptable salt thereof, wherein:

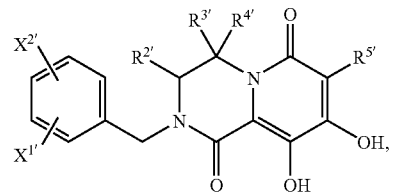

(IIa)

wherein:
$X^{1'}$ and $X^{2'}$ are each independently:
(1) —H,
(2) C$_{1-4}$ alkyl,
(2) —O—C$_{1-4}$ alkyl,
(3) —C$_{1-4}$ haloalkyl,
(4) —O—C$_{1-4}$ haloalkyl, or
(5) halo;

$R^{2'}$ is —H or —C$_{1-4}$ alkyl;
$R^{3'}$ is —H or —C$_{1-4}$ alkyl;
or alternatively $R^{2'}$ and $R^{3'}$ together form a direct bond to give a ring double bond;
$R^{4'}$ is:
(1) —H,
(2) —C$_{1-4}$ alkyl optionally substituted with one of —OH, —N(R$^{a'}$R$^{b'}$), or —C(=O)N(R$^{a'}$R$^{b'}$),
(3) —C(=O)N(R$^{a'}$R$^{b'}$),
(4) —(CH$_2$)$_{1-3}$—R$^{k_1}$,
(5) —(CH$_2$)$_{1-3}$—O—R$^{k_1}$, or
(6) —(CH$_2$)$_{1-3}$—O—(CH$_2$)$_{1-3}$—R$^{k_1}$;
  wherein R$^{k_1}$ is:
  (i) phenyl, which is optionally substituted with from 1 to 3 substituents each of which is independently —C$_{1-4}$ alkyl, —O—C$_{1-4}$ alkyl, —C$_{1-4}$ haloalkyl, —O—C$_{1-4}$ haloalkyl, or halo; or
  (ii) HetD, wherein HetD is a 5- or 6-membered saturated ring containing 1 or 2 N atoms, 0 or 1 S atoms, and a balance of carbon atoms, wherein the saturated ring is optionally substituted with from 1 to 4 substituents each of which is independently halo, —C$_{1-4}$ alkyl, —C$_{1-4}$ haloalkyl, —O—C$_{1-4}$ alkyl, —O—C$_{1-4}$ haloalkyl, or oxo;

$R^{5'}$ is:
(1) —H,
(2) —C$_{1-4}$ alkyl,
(3) —C$_{1-4}$ alkyl-N(R$^{a'}$R$^{b'}$), (4) halo,
(5) —CN, or
(6) —(CH$_2$)$_{1-3}$-HetB;
wherein
HetB is a 5- or 6-membered saturated ring containing 1 or 2 N atoms and carbon atoms, wherein the saturated ring is optionally substituted with from 1 to 4 substituents each of which is independently halogen, —C$_{1-4}$ alkyl, —C$_{1-4}$ haloalkyl, —O—C$_{1-4}$ alkyl, —O—C$_{1-4}$ haloalkyl, or oxo; and each R$^{a\prime}$ and R$^{b\prime}$ is independently —H or —C$_{1-4}$ alkyl.

In an aspect of the preceding sub-class, R$^{2\prime}$ and R$^{3\prime}$ are each —H or methyl, with the proviso that R$^{2\prime}$ and R$^{3\prime}$ are not both methyl; or alternatively R$^{2\prime}$ and R$^{3\prime}$ together form a direct bond to give a ring double bond, with the proviso that when R$^{2\prime}$ and R$^{3\prime}$ together form a direct bond, R$^{4\prime}$ is —H.

In another aspect of the preceding sub-class, HetB is pyrrolidinyl, pyrazolidinyl, imidazolidinyl, piperidinyl, or piperazinyl, which is optionally substituted with from 1 to 4 substituents each of which is independently halogen (e.g., fluoro, chloro, or bromo), —C$_{1-4}$ alkyl (e.g., methyl), —C$_{1-4}$ haloalkyl (e.g., trifluoromethyl), —O—C$_{1-4}$ alkyl (e.g., methoxy), —O—C$_{1-4}$ haloalkyl (e.g., —OCH$_3$), or oxo.

Still another sub-class of the present invention includes compounds of Formula (IIa), or a pharmaceutically acceptable salt thereof, wherein:

X$^{1\prime}$ and X$^{2\prime}$ are each independently:
(1) —H,
(2) methyl,
(2) —OCH$_3$,
(3) —CF$_3$,
(4) —O—CF$_3$,
(5) chloro,
(6) fluoro, or
(7) bromo;

R$^{2\prime}$ is —H or methyl;
R$^3$ is —H or methyl;
or alternatively R$^{2\prime}$ and R$^{3\prime}$ together form a direct bond to give a ring double bond;

R$^{4\prime}$ is:
(1) —H,
(2) methyl,
(3) —CH$_2$OH,
(3) —C(=O)N(CH$_3$)$_2$,
(4) —CH$_2$—R$^{k\prime}$, or
(5) —CH$_2$—O—CH$_2$—R$^{k\prime}$;
wherein R$^{k\prime}$ is:
(i) phenyl, which is optionally substituted with from 1 to 3 substituents each of which is independently —CH$_3$, —OCH$_3$, —CF$_3$, —OCF$_3$, chloro, bromo or fluoro; or
(ii) HetD, wherein HetD is a 5- or 6-membered saturated ring containing 1 or 2 N atoms, 0 or 1 S atoms, and a balance of carbon atoms, wherein the saturated ring is optionally substituted with from 1 to 4 substituents each of which is independently chloro, bromo, fluoro, —CH$_3$, —CF$_3$, —OCH$_3$, —OCF$_3$, or oxo; and R$^{5\prime}$ is:
(1) —H,
(2) methyl,
(3) —(CH$_2$)$_{1-2}$—N(CH$_3$)$_2$,
(4) fluoro,
(5) bromo,
(6) iodo,
(7) —CN, or
(8) —CH$_2$-HetB;

wherein
HetB is a 5- or 6-membered saturated ring containing 1 or 2 N atoms and carbon atoms, wherein the saturated ring is optionally substituted with from 1 to 4 substituents each of which is independently chloro, bromo, fluoro, —CH$_3$, —CF$_3$, —OCH$_3$, —OCF$_3$, or oxo.

In an aspect of the preceding sub-class, R$^{2\prime}$ and R$^{3\prime}$ are each —H or methyl, with the proviso that R$^{2\prime}$ and R$^{3\prime}$ are not both methyl; or alternatively R$^{2\prime}$ and R$^{3\prime}$ together form a direct bond to give a ring double bond, with the proviso that when R$^{2\prime}$ and R$^{3\prime}$ together form a direct bond, R$^{4\prime}$ is —H.

In another aspect of the preceding sub-class, HetB is pyrrolidinyl, pyrazolidinyl, imidazolidinyl, piperidinyl, or piperazinyl, which is optionally substituted with from 1 to 4 substituents each of which is independently chloro, bromo, fluoro, —CH$_3$, —CF$_3$, —OCH$_3$, —OCF$_3$, or oxo.

Another class of the present invention includes compounds of Formula (III), or a pharmaceutically acceptable salt thereof:

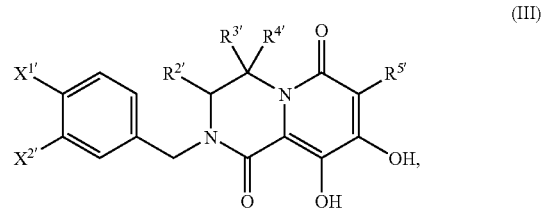

(III)

wherein:
X$^{1\prime}$ and X$^{2\prime}$ are each independently —H or halo;
and all other variables are as set forth in Formula (II) for the preceding class. A sub-class of this class includes compounds of Formula (III), or a pharmaceutically acceptable salt thereof, wherein X$^{1\prime}$ and X$^{2\prime}$ are each independently -H or halo; and all other variables are as defined above in any one of the sub-classes of the preceding class defined by Formula (II) (including sub-classes defined by Formula (IIa)). Aspects of this sub-class are analogous to the aspects set forth above for the preceding Formula (II) sub-class (including aspects defined by Formula (IIa)).

Another sub-class of this class includes compounds of Formula (III), or a pharmaceutically acceptable salt thereof, wherein X$^{1\prime}$ and X$^{2\prime}$ are each independently —H, fluoro, chloro, or bromo; and all other variables are as defined for the class or as defined in a sub-class thereof. In still another sub-class, X$^{1\prime}$ is fluoro and X$^{2\prime}$ is —H; and all other variables are as defined for the class or as defined in a sub-class thereof.

Other embodiments of the present invention include compounds of Formula (II), (IIa), or (III) respectively, wherein each R$^{a\prime}$ and R$^{b\prime}$ is independently —H or —C$_{1-4}$ alkyl; and all other variables are as originally defined or as defined in any of the foregoing embodiments or aspects thereof.

Still other embodiments of the present invention include compounds of Formula (II), (IIa), or (III) respectively, wherein each R$^{a\prime}$ and R$^{b\prime}$ is independently —H, methyl, or ethyl; and all other variables are as originally defined or as defined in any of the foregoing embodiments or aspects thereof.

Still other embodiments of the present invention include compounds of Formula (II), wherein R$^{a\prime}$ is a —C$_{1-4}$ alkyl (e.g., methyl, ethyl or n-propyl), allyl, or benzyl; and all other variables are as originally defined or as defined in any of the foregoing embodiments or aspects thereof.

Another embodiment of the present invention is a compound selected from the group consisting of 2-benzyl-8,9-dihydroxy-3,4-dihydro-2H-pyrido[1,2-a]pyrazine-1,6-dione;

2-(4-fluorobenzyl)-8,9-dihydroxy-3,4-dihydro-2H-pyrido[1,2-a]pyrazine-1,6-dione;

2-(4-fluorobenzyl)-8,9-dihydroxy-7-methyl-3,4-dihydro-2H-pyrido[1,2-a]pyrazine-1,6-dione;

2-(4-fluorobenzyl)-8,9-dihydroxy-7-bromo-3,4-dihydro-2H-pyrido[1,2-a]pyrazine-1,6-dione;

2-(4-fluorobenzyl)-8,9-dihydroxy-7-iodo-3,4-dihydro-2H-pyrido[1,2-a]pyrazine-1,6-dione;

2-(3-chlorobenzyl)-8,9-dihydroxy-3,4-dihydro-2H-pyrido[1,2-a]pyrazine-1,6-dione;

2-(4-chlorobenzyl)-8,9-dihydroxy-3,4-dihydro-2H-pyrido[1,2-a]pyrazine-1,6-dione 2-(3,4-dichlorobenzyl)-8,9-dihydroxy-3,4-dihydro-2H-pyrido[1,2-a]pyrazine-1,6-dione;

2-(3,4-difluorobenzyl)-8,9-dihydroxy-3,4-dihydro-2H-pyrido[1,2-a]pyrazine-1,6-dione 2-(3-chloro-fluorobenzyl)-8,9-dihydroxy-3,4-dihydro-2H-pyrido[1,2-a]pyrazine-1,6-dione 2-(4-fluorobenzyl)-8,9-dihydroxy-7-(piperidin-1-ylmethyl)-3,4-dihydro-2H-pyrido[1,2-a]pyrazine-1,6-dione;

2-(3-chloro-4-fluorobenzyl)-8,9-dihydroxy-7-(piperidin-1-ylmethyl)-3,4-dihydro-2H-pyrido[1,2-a]pyrazine-1,6-dione;

2-(4-fluorobenzyl)-8,9-dihydroxy-7-[(dimethylamino)methyl]-3,4-dihydro-2H-pyrido[1,2-a]pyrazine-1,6-dione;

2-(4-fluorobenzyl)-8,9-dihydroxy-2H-pyrido[1,2-a]pyrazine-1,6-dione 2-benzyl-8,9-dihydroxy-2H-pyrido[1,2-a]pyrazine-1,6-dione;

2-(4-fluorobenzyl)-8,9-dihydroxy4-methyl-3,4-dihydro-2H-pyrido[1,2-a]pyrazine-1,6-dione 2-(4-fluorobenzyl)-8,9-dihydroxy4,4-dimethyl-3,4-dihydro-2H-pyrido[1,2-a]pyrazine-1,6-dione;

2-(4-fluorobenzyl)-8,9-dihydroxy-3-methyl-3,4-dihydro-2H-pyrido[1,2-a]pyrazine-1,6-dione;

2-(4-fluorobenzyl)-8,9-dihydroxy-1,6-dioxo-1,3,4,6-tetrahydro-2H-pyrido[1,2-a]-pyrazine-7-carbonitrile;

2-(4-fluorobenzyl)-8,9-dihydroxy-7-[(4-methyl-3-oxopiperazin-1-yl)methyl]-3,4-dihydro-2H-pyrido[1,2-a]pyrazine-1,6-dione;

2-(4-fluorobenzyl)-8,9-dihydroxy-7-[(3-oxopiperazin-1-yl)methyl]-3,4-dihydro-2H-pyrido[1,2-a]pyrazine-1,6-dione;

4-[(benzyloxy)methyl]-2-(4-fluorobenzyl)-8,9-dihydroxy-3,4-dihydro-2H-pyrido[1,2-a]pyrazine-1,6-dione;

4(hydroxymethyl)-2-(4-fluorobenzyl)-8,9-dihydroxy-3,4-dihydro-2H-pyrido[1,2-a]pyrazine-1,6-dione;

4-[(1,1-dioxido-1,2-thiazinan-2-yl)methyl]-2-(4-fluorobenzyl)-8,9-dihydroxy-3,4-dihydro-2H-pyrido[1,2-a]pyrazine-1,6-dione;

2-(4-fluorobenzyl)-8,9-dihydroxy-7-(piperidin-1-ylmethyl)-2H-pyrido[1,2-a]pyrazine-1,6-dione;

2-(4-fluorobenzyl)-8,9-dihydroxy-7-[(3-oxopiperazin-1-yl)methyl]-2H-pyrido[1,2-a]pyrazine-1,6-dione;

2-(4-fluorobenzyl)-8,9-dihydroxy-7-[(4-methyl-3-oxopiperazin-1-yl)methyl]-2H-pyrido[1,2-a]pyrazine-1,6-dione;

2-(4-fluorobenzyl)-8,9-dihydroxy-7-[(morpholin-4-yl)methyl]-2H-pyrido[1,2-a]pyrazine-1,6-dione;

2-(4-fluorobenzyl)-8,9-dihydroxy-7-[(thiomorpholin-4-yl)methyl]-2H-pyrido[1,2-a]pyrazine-1,6-dione;

2-[4-fluoro-2-(methylthio)benzyl)-8,9-dihydroxy-2H-pyrido[1,2-a]pyrazine-1,6-dione;

7-[(1-acetylpiperidin-4-yl)methyl]-2-(4-fluorobenzyl)-8,9-dihydroxy-3,4-dihydro-2H-pyrido[1,2-a]pyrazine-1,6-dione;

2-(4-fluorobenzyl)-8,9-dihydroxy-7-{[1-(trifluoroacetyl)piperidin-4-yl]methyl}-3,4-dihydro-2H-pyrido[1,2-a]pyrazine-1,6-dione;

7-{[1-(cyclopropylmethyl)piperidin-3-yl]methyl}-2-(4-fluorobenzyl)-8,9-dihydroxy-3,4-dihydro-2H-pyrido[1,2-a]pyrazine-1,6-dione;

7-[(1-acetylpiperidin-3-yl)methyl]-2-(4-fluorobenzyl)-8,9-dihydroxy-3,4-dihydro-2H-pyrido[1,2-a]pyrazine-1,6-dione;

7-[(1-acetylpiperidin-2-yl)methyl]-2-(4-fluorobenzyl)-8,9-dihydroxy-3,4dihydro-2H-pyrido[1,2-a]pyrazine-1,6-dione;

7-{[1-(cyclopropylmethyl)piperidin-2-yl]methyl}-2-(4-fluorobenzyl)-8,9-dihydroxy-3,4-dihydro-2H-pyrido[1,2-a]pyrazine-1,6-dione;

2-(3-cyanobenzyl)-8,9-dihydroxy-3,4-dihydro-2H-pyrido[1,2-a]pyrazine-1,6-dione 2-(biphenyl-3-ylmethyl)-8,9-dihydroxy-3,4-dihydro-2H-pyrido [1,2-a]pyrazine-1,6-dione (±)-1-[(benzyloxy)methyl]-2-(4-fluorobenzyl)-4,5-dihydroxy-1,1a,2,8a-tetrahydrocyclo-propa[e]pyrido[1,2-a]pyrazine-3,7-dione;

(±)-1-(methoxymethyl)-2-(4-fluorobenzyl)4,5-dihydroxy-1,1a,2,8a-tetrahydrocyclo-propa[e]pyrido[1,2-a]pyrazine-3,7-dione;

(±)-1-[(allyloxy)methyl]-2-(4-fluorobenzyl)-4,5-dihydroxy-1,1a,2,8a-tetrahydrocyclo-propa[e]pyrido[1,2-a]pyrazine-3,7-dione;

(±)-1-(ethoxymethyl)-2-(4-fluorobenzyl)-4,5-dihydroxy-1,1a,2,8a-tetrahydrocyclo-propa[e]pyrido[1,2-a]pyrazine-3,7-dione;

(±)-1-(n-propoxymethyl)-2-(4-fluorobenzyl)-4,5-dihydroxy-1,1a,2,8a-tetrahydrocyclo-propa[e]pyrido[1,2-a]pyrazine-3,7-dione;

2-[1-(4-fluorophenyl)ethyl]-8,9-dihydroxy-3,4-dihydro-2H-pyrido[1,2-a]pyrazine-1,6-dione;

5-(4-fluorobenzyl)-7,8-dihydroxy-5H-pyrido[1,2-a]quinoxaline-6,10-dione;

5-(4-fluorobenzyl)-7,8-dihydroxy-5H-pyrido[1,2-a:3',2'-e]pyrazine-6,10-dione;

5-(4-fluorobenzyl)-7,8-dihydroxy-5H-pyrido[1,2-a:2',3'-e]pyrazine-6,10-dione;

and pharmaceutically acceptable salts thereof.

Other embodiments of the present invention include the following:

(a) A pharmaceutical composition comprising a therapeutically effective amount of a compound of the invention (e.g., a compound of Formula (I) or Formula (II) or Formula (III) or any of the specific compounds set forth above) and a pharmaceutically acceptable carrier.

(b) A pharmaceutical composition which comprises the product prepared by combining (e.g., mixing) a therapeutically effective amount of a compound of the invention and a pharmaceutically acceptable carrier.

(c) The pharmaceutical composition of (a) or (b), further comprising a therapeutically effective amount of an HIV infection/AIDS treatment agent selected from the group consisting of HIV/AIDS antiviral agents, immunomodulators, and anti-infective agents.

(d) The pharmaceutical composition of (c), wherein the HIV infection/AIDS treatment agent is an antiviral selected from the group consisting of HIV protease inhibitors, non-nucleoside HIV reverse transcriptase inhibitors, and nucleoside HIV reverse transcriptase inhibitors.

(e) A combination useful for inhibiting HIV integrase, for treating or preventing infection by HIV, or for preventing, treating or delaying the onset of AIDS, which is a therapeutically effective amount of a compound of the invention and a therapeutically effective amount of an HIV infection/AIDS treatment agent selected from the group consisting of HIV/AIDS antiviral agents, immunomodulators, and anti-infective agents.

(f) The combination of (e), wherein the HIV infection/AIDS treatment agent is an antiviral selected from the group consisting of HIV protease inhibitors, non-nucleoside HIV reverse transcriptase inhibitors and nucleoside HIV reverse transcriptase inhibitors.

(g) A method of inhibiting HIV integrase in a subject in need thereof which comprises administering to the subject a therapeutically effective amount of a compound of the invention.

(h) A method of preventing or treating infection by HIV in a subject in need thereof which comprises administering to the subject a therapeutically effective amount of a compound of the invention.

(i) The method of (h), wherein the compound of the invention is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors.

(j) A method of preventing, treating or delaying the onset of AIDS in a subject in need thereof which comprises administering to the subject a therapeutically effective amount of a compound of the invention.

(k) The method of (j), wherein the compound is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors (l) A method of inhibiting HIV integrase in a subject in need thereof which comprises administering to the subject the pharmaceutical composition of (a), (b), (c) or (d) or the combination of (e) or (f).

(m) A method of preventing or treating infection by HIV in a subject in need thereof which comprises administering to the subject the pharmaceutical composition of (a), (b), (c) or (d) or the combination of (e) or (f).

(n) A method of preventing, treating or delaying the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) inhibiting HIV integrase, (b) preventing or treating infection by HIV, or (c) preventing, treating or delaying the onset of AIDS. In these uses, the compounds of the present invention can optionally be employed in combination with one or more HIV/AIDS treatment agents selected from HIV/AIDS antiviral agents, anti-infective agents, and immunomodulators.

Additional embodiments of the invention include the pharmaceutical compositions, combinations and methods set forth in (a)-(n) above and the uses set forth in the preceding paragraph, wherein the compound of the present invention employed therein is a compound of one of the embodiments, or an aspect or feature or sub-feature thereof, described above.

In all of the foregoing embodiments describing compositions, combinations and methods, the compound may optionally be used in the form of a pharmaceutically acceptable salt.

As used herein, the term "$C_{1-6}$ alkyl" (or "$C_1$-$C_6$ alkyl") means a linear or branched chain alkyl group having from 1 to 6 carbon atoms and includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl.

The term "$C_0$" as employed in expressions such as "—$C_{0-6}$ alkyl-" means a direct covalent bond. For example, in the group —$C_{1-6}$ alkyl—$N(R^a)$—$C_{0-6}$ alkyl-$S(O)_n R^k$, when the second alkylene group is "$C_0$", then the group is —$C_{1-6}$ alkyl—$N(R^a)$—$S(O)_n R^k$.

The term "—$C_{1-6}$ alkyl-" refers to a $C_1$ to $C_6$ linear or branched alkyl group as just defined which is bivalent. It can alternatively be referred to as "$C_{1-6}$ alkylene" or "$C_{1-6}$ alkanediyl". A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—.

The term "$C_{2-6}$ alkenyl" (or "$C_2$-$C_6$ alkenyl") means a linear or branched chain alkenyl group having from 2 to 6 carbon atoms and includes all of the hexenyl and pentenyl isomers as well as 1-butenyl, 2-butenyl, 3-butenyl, isobutenyl, 1-propenyl, 2-propenyl, and ethenyl (or vinyl). Similar terms such as "$C_{2-4}$ alkenyl" have an analogous meaning. A class of alkenyls of particular interest with respect to the invention is —$CH_2$—$CH$=$CH$—$(CH_2)_{0-4}$H, and sub-classes of particular interest include —$CH$=$CH$—$(CH_2)_{1-2}$H, —$CH$=$CH$—$CH_3$, and —$CH$=$CH_2$. Another class of alkenyls of particular interest with respect to the invention is alkenyls selected from —$(CH_2)_2$—$CH$=$CH$—$(CH_2)_{0-2}$H and —$CH_2$—$CH$=$CH$—$(CH_2)_{0-3}$H.

The term "$C_{2-5}$ alkynyl" (or "$C_2$-$C_5$ alkynyl") means a linear or branched chain alkynyl group having from 2 to 5 carbon atoms and includes all of the pentynyl isomers as well as 1-butynyl, 2-butynyl, 3-butynyl, 1-propynyl, 2-propynyl, and ethynyl (or acetylenyl). Similar terms such as "$C_{2-4}$ alkynyl" have an analogous meaning. A class of alkynyls of particular interest with respect to the invention is —C≡C—$(CH_2)_{1-4}$H (e.g., —C≡C—$CH_3$). Another class of alkynyls of particular interest with respect to the invention is alkynyls selected from —$CH_2$—≡—$(CH_2)_{1-3}$H and —$(CH_2)_2$—≡—$(CH_2)_{1-2}$H.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). Similar terms such as "$C_{3-6}$ cycloalkyl" have an analogous meaning.

The term "halogen" (or "halo") refers to fluorine, chlorine, bromine and iodine (alternatively referred to as fluoro, chloro, bromo, and iodo).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning. The term "$C_{1-6}$ fluoroalkyl" has an analogous meaning except that the halogen substituents are restricted to fluoro. A class of fluoroalkyls of particular interest with respect to the invention is the series $(CH_2)_{0-4}CF_3$ (i.e., trifluoromethyl, 2,2,2-trifluoroethyl, 3,3,3-trifluoro-n-propyl, etc.).

The term "oxo" means a divalent oxygen substituent; i.e., =O. An oxo substituent on a carbon atom in a heteroaromatic ring refers to the keto form of the keto-enol tautomer, as exemplified here for an oxopyridinyl substituent:

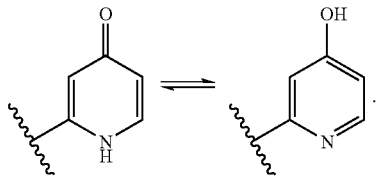

Compounds of the present invention having an oxo substituent on a carbon atom of a heteroaromatic ring are understood to include compounds in which only the keto form is present, compounds in which only the enol form is present, and compounds in which the keto and enol forms are both present.

The term "aryl" as used herein refers to an aromatic carbocyclic ring or an aromatic carbocyclic fused ring system. The fused ring system contains two or more carbocyclic rings in which each ring shares two adjacent carbon atoms with at least one other ring. The aryl group may be attached to the rest of the molecule at any carbon atom which results in a stable compound. A subset of aryl groups particularly suitable for use in the present invention (e.g., in the definition of $R^k$) includes those selected from phenyl, naphthyl, anthryl, and phenanthryl. Another particularly suitable subset of aryl groups is phenyl and naphthyl. Still another particularly suitable subset of aryl groups is phenyl per se.

The term "heterocyclic ring" refers to a 4- to 8-membered, saturated or unsaturated monocyclic ring that contains one or more heteroatoms (e.g., from 1 to 6 heteroatoms, from 1 to 5 heteroatoms, from 1 to 4 heteroatoms, from 1 to 3 heteroatoms, 1 or 2 heteroatoms, or 1 heteroatom) independently selected from N, O and S and a balance of carbon atoms (the ring typically contains at least one carbon atom); and wherein any one or more of the nitrogen and sulfur heteroatoms is optionally oxidized, and any one or more of the nitrogen heteroatoms is optionally quaternized. The heterocyclic ring may be attached to the rest of the molecule via any heteroatom or carbon atom in the ring, provided that attachment results in the creation of a stable structure. When the heterocyclic ring has substituents, it is understood that the substituents may be attached to any atom in the ring, whether a heteroatom or a carbon atom, provided that a stable chemical structure results.

A subset of the heterocyclic rings useful in the present invention (e.g., in the definition of $R^k$) includes any 4- to 7-membered saturated or mono-unsaturated heterocyclic ring, wherein the ring contains at least one carbon atom and from 1 to 4 heteroatoms independently selected from N, O and S. A subgroup of this subset includes any 4- to 7-membered saturated or mono-unsaturated heterocyclic ring in which the ring contains at least one carbon atom and a total of from 1 to 4 heteroatoms independently selected from 1 to 4 N atoms, from 0 to 2 O atoms, and from 0 to 2 S atoms. Representative examples of saturated heterocyclic rings include piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, tetrahydrothienyl, pyrazolidinyl, hexahydropyrimidinyl, thiazinanyl (e.g., 1,2-thiazinanyl 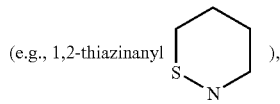), thiazepanyl, thiadiazepanyl, dithiazepanyl, azepanyl (i.e., 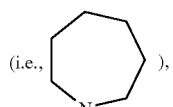), diazepanyl, thiadiazinanyl, (e.g., 1,2,6-thiadiazinanyl 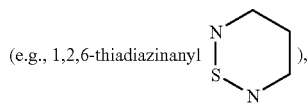), and dioxanyl. Representative examples of mono-unsaturated rings are the same as the saturated rings listed in the preceding sentence except that each ring contains a double bond.

Another subset of the heterocyclic rings useful in the present invention (e.g., in the definition of HetB) includes any 5- or 6-membered saturated or mono-unsaturated ring containing from 1 to 4 heteroatoms independently selected from N, O and S. A useful subgroup of this subset includes any 5- or 6-membered saturated or mono-unsaturated heterocyclic ring in which the ring contains at least one carbon atom and a total of from 1 to 4 heteroatoms independently selected from 1 to 4 N atoms, from 0 to 2 O atoms, and from 0 to 2 S atoms. Another useful subgroup is identical to the preceding subgroup, except that it is limited to saturated heterocyclic rings. Still another subgroup of this subset of heterocyclic rings suitable for use in the present invention includes any 5- or 6-membered saturated ring containing 1 or 2 N atoms and carbon atoms. Representative examples of this subgroup include piperidinyl, pyrazolidinyl, imidazolidinyl, piperazinyl, piperidinyl, and hexahydropyrimidinyl.

Another subset of the heterocyclic rings useful in the present invention (e.g., in the definition of HetD) includes any 5- or 6-membered saturated ring containing 1 or 2 N atoms, 0 or 1 S atoms, and a balance of carbon atoms.

Still another subset of the heterocyclic rings useful in the present invention are the heteroaromatic rings. The term "heteroaromatic ring" (alternatively "heteroaryl ring") generally refers to a heterocyclic ring as defined above in which the ring is an aromatic ring. A useful subgroup of this subset (e.g., in the definition of $R^k$, HetA, or HetC) includes any 5- or 6-membered monocyclic aromatic ring which consist of carbon atoms and from 1 to 4 heteroatoms independently selected from N, O and S. Representative examples of this subgroup include pyridyl, pyrrolyl, pyrazinyl, pyrimidinyl, pyridazinyl, triazinyl, thienyl (or thiophenyl), thiazolyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. Another useful subgroup of this subset includes any 5- or 6-membered heteroaromatic ring in which the ring contains a total of from 1 to 4 heteroatoms independently selected from 1 to 4 N atoms, from 0 to 2 O atoms, and from 0 to 2 S atoms. Another useful subgroup includes any 5- or 6-membered heteroaromatic ring containing 1 or 2 N atoms and carbon atoms.

The term "fused bicyclic heterocycle" refers to any 8- to 12-membered bicyclic ring system containing one or more heteroatoms (e.g., from 1 to 6 heteroatoms, from 1 to 5 heteroatoms, from 1 to 4 heteroatoms, from 1 to 3 heteroatoms, 1 or 2 heteroatoms, or 1 heteroatom) independently selected from N, O and S, in which one ring contains all of the heteroatoms or each ring contains at least one of the heteroatoms, and wherein each ring is saturated or unsaturated, and two adjacent ring atoms are shared by each of the rings in the ring system and each of the two shared atoms is independently a carbon atom or a heteroatom. Any one or more of the nitrogen and sulfur heteroatoms in the ring system is optionally oxidized, and any one or more of the nitrogen heteroatoms is optionally quaternized. The fused bicyclic heterocycle may be attached to the rest of the molecule via any heteroatom or carbon atom in the ring, provided that attachment results in the creation of a stable structure. When the bicyclic heterocycle has substituents, it is understood that the substituents may be attached to any atom in the ring, whether a heteroatom or a carbon atom, provided that a stable chemical structure results.

A subset of the fused bicyclic heterocycles useful in the present invention (e.g., in the definition of $R^1$) includes any 9- or 10-membered fused bicyclic heterocycle containing from 1 to 4 heteroatoms independently selected from N, O and S, wherein at least one of the rings is aromatic. Representative examples of bicyclic heterocycles in this subset include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e., 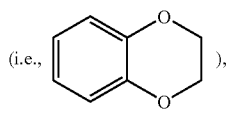 ), and benzo-1,3-dioxolyl (i.e., 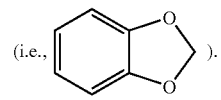 ).

Unless expressly stated to the contrary, an "unsaturated" ring is a partially or fully unsaturated ring.

Unless expressly stated to the contrary, all ranges cited herein are inclusive. For example, a heterocyclic ring described as containing from "1 to 4 heteroatoms" means the ring can contain 1, 2, 3 or 4 heteroatoms.

When any variable (e.g., $R^a$, $R^b$, or $R^c$) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "each aryl is optionally substituted with from 1 to 5 substituents...") includes mono- and poly-substitution by a named substituent to the extent such single and multiple substitution (including multiple substitution at the same site) is chemically allowed.

The symbol "⌇⌇⌇" in front of an open bond in the structural formula of a group marks the point of attachment of the group to the rest of the molecule.

The compounds of the present invention may have asymmetric centers and may occur, except when specifically noted, as mixtures of stereoisomers or as individual diastereomers, or enantiomers, with all isomeric forms being included in the present invention.

As would be recognized by one of ordinary skill in the art, all of the compounds of the present invention can exist as tautomers such as the following:

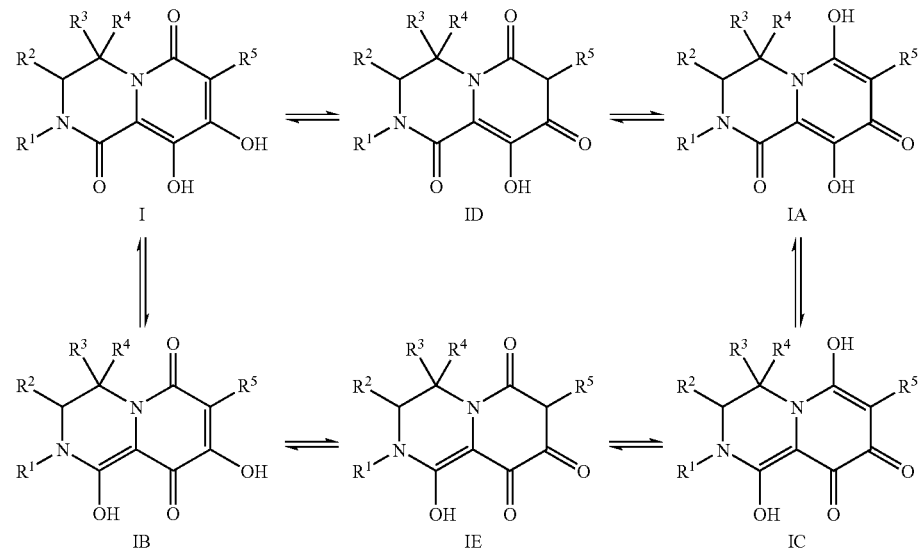

It is to be understood for the purposes of the present invention that a reference herein to a compound of Formula I is a reference to compound I per se, or to any one of its tautomers per se (e.g., IA, IB, IC, ID or IE), or to mixtures of two or more tautomers (e.g., two or more of I, IA, IB, IC, ID and IE).

The compounds of the present invention are useful in the inhibition of HIV integrase, the prevention or treatment of infection by human immunodeficiency virus (HIV) and the prevention, treatment or the delay in the onset of consequent pathological conditions such as AIDS. Preventing AIDS, treating AIDS, delaying the onset of AIDS, or preventing or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The compounds of the present invention can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. When the compounds of the invention carry an acidic moiety, suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

For the purpose of preventing or treating HIV infection or preventing, treating or delaying the onset of AIDS, the compounds of the present invention can be administered orally, parenterally (including subcutaneous injections, intravenous, intramuscular, intrasternal injection or infusion techniques), by inhalation spray, or rectally, in the form of a unit dosage of a pharmaceutical composition containing a therapeutically effective amount of the compound and conventional non-toxic pharmaceutically-acceptable carriers, adjuvants and vehicles.

The term "administration" and variants thereof (e.g., "administering" a compound) in reference to a compound of the invention mean providing the compound to the individual in need of treatment. When a compound of the invention is provided in combination with one or more other active agents (e.g., antiviral agents useful for treating HIV infection or AIDS), "administration" and its variants are each understood to include concurrent and sequential provision of the compound and other agents.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" (which may be alternatively referred to herein as "patient") as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated. When the active compound (i.e., active ingredient) is administered as the salt, references to the amount of active ingredient are to the free acid or free base form of the compound.

The pharmaceutical compositions can be in the form of orally-administrable suspensions or tablets or capsules, nasal sprays, sterile injectable preparations, for example, as sterile injectable aqueous or oleagenous suspensions or suppositories. These compositions can be prepared by methods and contain excipients which are well known in the art. Suitable methods and ingredients are described in *Remington's Pharmaceutical Sciences,* $18^{th}$ edition, edited by A. R. Gennaro, Mack Publishing Co., 1990, which is herein incorporated by reference in its entirety.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of the HIV integrase inhibitor compounds of the present invention with one or more agents useful in the treatment of HIV infection or AIDS. For example, the compounds of this invention may be effectively administered, whether at periods of pre-exposure and/or post-exposure, in combination with effective amounts of one or more of the HIV/AIDS antivirals, imunomodulators, antiinfectives, or vaccines useful for treating HIV infection or AIDS. Suitable antiviral agents include those listed in the following

TABLE

| Drug Name | Manufacturer (Tradename and/or Location) | Indication (Activity) |
|---|---|---|
| abacavir GW 1592 1592U89 | Glaxo Welcome (ZIAGEN ®) | HIV infection, AIDS, ARC (nRTI) |
| abacavir + lamivudine + zidovudine | GlaxoSmithKline (TRIZIVIR ®) | HIV infection, AIDS, ARC (nRTIs) |
| acemannan | Carrington Labs (Irving, TX) | ARC |
| ACH 126443 | Achillion Pharm. | HIV infections, AIDS, ARC (nRTI) |
| acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| adefovir dipivoxil GS 840 | Gilead | HIV infection, AIDS, ARC (reverse transcriptase inhibitor) |
| AL-721 | Ethigen (Los Angeles, CA) | ARC, PGL, HIV positive, AIDS |
| alpha interferon | GlaxoSmithKline | Kaposi's sarcoma, HIV, in combination w/Retrovir |
| AMD3100 | AnorMed | HIV infection, AIDS, ARC (CXCR4 antagonist) |
| amprenavir 141 W94 GW 141 VX478 (Vertex) | GlaxoSmithKline (AGENERASE ®) | HIV infection, AIDS, ARC (PI) |
| ansamycin LM 427 | Adria Laboratories (Dublin, OH) Erbamont (Stamford, CT) | ARC |
| antibody which neutralizes pH labile alpha aberrant interferon | Advanced Biotherapy Concepts (Rockville, MD) | AIDS, ARC |
| AR177 | Aronex Pharm | HIV infection, AIDS, ARC |
| atazanavir (BMS 232632) | Bristol-Myers Squibb (REYATAZ ™) | HIV infection, AIDS, ARC (PI) |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (PI) |
| BMS-234475 (CGP-61755) | Bristol-Myers Squibb/ Novartis | HIV infection, AIDS, ARC (PI) |
| capravirine (AG-1549, S-1153) | Pfizer | HIV infection, AIDS, ARC (nnRTI) |
| CI-1012 | Warner-Lambert | HIV-1 infection |
| cidofovir | Gilead Science | CMV retinitis, herpes, papillomavirus |
| curdlan sulfate | AJI Pharma USA | HIV infection |
| cytomegalovirus immune globin | MedImmune | CMV retinitis |
| cytovene ganciclovir | Syntex | sight threatening CMV peripheral CMV retinitis |
| delavirdine | Pharmacia-Upjohn (RESCRIPTOR ®) | HIV infection, AIDS, ARC (nnRTI) |
| dextran Sulfate | Ueno Fine Chem. Ind. Ltd. (Osaka, Japan) | AIDS, ARC, HIV positive asymptomatic |
| ddC (zalcitabine, dideoxycytidine) | Hoffman-La Roche (HIVID ®) | HIV infection, AIDS, ARC (nucleosdie reverse transcriptase inhibitor) |
| ddI (didanosine, dideoxyinosine) | Bristol-Myers Squibb (VIDEX ®) | HIV infection, AIDS, ARC; combination with AZT/d4T (nRTI) |
| DPC 681 &DPC 684 | DuPont | HIV infection, AIDS, ARC (PIs) |
| DPC 961 &DPC 083 | Bristol-Myers Squibb (from DuPont Pharma) | HIV infection AIDS, ARC (nnRTIs) |
| EL10 | Elan Corp, PLC (Gainesville, GA) | HIV infection |
| efavirenz (DMP 266) | Bristol-Myers Squibb (SUSTIVA ®) Merck (STOCRIN ®) | HIV infection, AIDS, ARC (non-nucleoside RT inhibitor) |
| famciclovir | Novartis (FAMVIR ®) | herpes zoster, herpes simplex |

TABLE-continued

| Drug Name | Manufacturer (Tradename and/or Location) | Indication (Activity) |
|---|---|---|
| emtricitabine FTC | Gilead (from Triangle Pharmaceuticals) (COVIRACIL ®) Emory University | HIV infection, AIDS, ARC (nRTI) |
| emvirine | Gilead (from Triangle Pharmaceuticals) (COACTINON ®) | HIV infection, AIDS, ARC (nnRTI) |
| enfuvirtide T-20 | Trimeris &Roche (FUZEON ®) | HIV infection, AIDS, ARC (fusion inhibitor) |
| HBY097 | Hoechst Marion Roussel | HIV infection, AIDS, ARC (nnRTI) |
| fosamprenavir | Glaxo Smith Kline | HIV infection, AIDS, ARC (prodrug of amprenavir) |
| hypericin | VIMRx Pharm. | HIV infection, AIDS, ARC |
| recombinant human interferon beta | Triton Biosciences (Almeda, CA) | AIDS, Kaposi's sarcoma, ARC |
| interferon alfa-n3 | Interferon Sciences | ARC, AIDS |
| indinavir | Merck (CRIXIVAN ®) | HIV infection, AIDS, ARC, asymptomatic HIV positive, (PI) |
| ISIS 2922 | ISIS Pharmaceuticals | CMV retinitis |
| JE2147/AG1776 | Agouron | HIV infection, AIDS, ARC (PI) |
| KNI-272 | Nat'l Cancer Institute | HIV-assoc. diseases |
| lamivudine, 3TC | GlaxoSmithKline (EPIVIR ®) | HIV infection, AIDS, ARC (nRTI) |
| lamivudine + zidovudine | GlaxoSmithKline (COMBIVIR ®) | HIV infection, AIDS, ARC (nRTI) |
| lobucavir | Bristol-Myers Squibb | CMV infection |
| lopinavir (ABT-378) | Abbott | HIV infection, AIDS, ARC (PI) |
| lopinavir + ritonavir (ABT-378/r) | Abbott (KALETRA ®) | HIV infection, AIDS, ARC (PI) |
| mozenavir (DMP-450) | AVID (Camden, NJ) | HIV infection, AIDS, ARC (PI) |
| nelfinavir | Agouron (VIRACEPT ®) | HIV infection, AIDS, ARC (PI) |
| nevirapine | Boeheringer Ingleheim (VIRAMUNE ®) | HIV infection, AIDS, ARC (nnRTI) |
| novapren | Novaferon Labs, Inc. (Akron, OH) | HIV inhibitor |
| peptide T octapeptide sequence | Peninsula Labs (Belmont, CA) | AIDS |
| PRO 140 | Progenics | HIV infection, AIDS, ARC (CCR5 co-receptor inhibitor) |
| PRO 542 | Progenics | HIV infection, AIDS, ARC (attachment inhibitor) |
| trisodium phosphonoformate | Astra Pharm. Products, Inc | CMV retinitis, HIV infection, other CMV infections |
| PNU-140690 | Pharmacia Upjohn | HIV infection, AIDS, ARC (PI) |
| probucol | Vyrex | HIV infection, AIDS |
| RBC-CD4 | Sheffield Med. Tech (Houston TX) | HIV infection, AIDS, ARC |
| ritonavir (ABT-538) | Abbott (NORVIR ®) | HIV infection, AIDS, ARC (PI) |
| saquinavir | Hoffmann-LaRoche (FORTOVASE ®) | HIV infection, AIDS, ARC (PI) |
| stavudine; d4T didehydrodeoxy- thymidine | Bristol-Myers Squibb (ZERIT ®) | HIV infection, AIDS, ARC (nRTI) |
| T-1249 | Trimeris | HIV infection, AIDS, ARC (fusion inhibitor) |
| TAK-779 | Takeda | HIV infection, AIDS, ARC (injectable CCR5 receptor antagonist) |
| tenofovir | Gilead (VIREAD ®) | HIV infection, AIDS, ARC (nucleotide reverse transcriptase inhibitor) |
| tipranavir (PNU-140690) | Boehringer Ingelheim | HIV infection, AIDS, ARC (PI) |
| TMC-120 &TMC-125 | Tibotec | HIV infections, AIDS, ARC (nuRTIs) |

TABLE-continued

| Drug Name | Manufacturer (Tradename and/or Location) | Indication (Activity) |
|---|---|---|
| TMC-126 | Tibotec | HIV infection, AIDS, ARC (PI) |
| valaciclovir | GlaxoSmithKline | genital HSV &CMV infections |
| virazole ribavirin | Viratek/ICN (Costa Mesa, CA) | asymptomatic HIV positive, LAS, ARC |
| zidovudine; AZT | GlaxoSmithKline (RETROVIR ®) | HIV infection, AIDS, ARC, Kaposi's sarcoma in combination with other therapies (nRTI) |

PI = protease inhibitor
nnRTI = non-nucleoside reverse transcriptase inhibitor
nRTI = nucleoside reverse transcriptase inhibitor A compound of the present invention can also be administered in combination with an HIV integrase inhibitor such as a compound described in WO 99/62513,WO 99/62520, or WO 99/62897. A compound of the present invention can also be administered in combination with a CCR5 receptor antagonist, such as a compound described in WO 99/04794, WO 99/09984, WO 99/38514, WO 00/59497, WO 00/59498, WO 00/59502, WO 00/59503, WO 00/76511, WO 00/76512, WO 00/76513, WO 00/76514, WO 00/76792, or WO 00/76793. The compounds of this invention may be effectively administered, whether at periods of pre-exposure and/ or post-exposure, in combination with effective amounts of one or more HIV/AIDS antivirals, immunomodulators, anti-infectives, or vaccines useful for treating HIV infection or AIDS disclosed in the Table in WO 02/30930, which is herein incorporated by reference in its entirety.

It will be understood that the scope of combinations of the compounds of this invention with HIV/AIDS antivirals, immunomodulators, anti-infectives or vaccines is not limited to those described or referenced above, but includes in principle any combination with any pharmaceutical composition useful for the treatment of AIDS. The HIV/AIDS antivirals and other agents will typically be employed in these combinations in their conventional dosage ranges and regimens as reported in the art, including the dosages described in the *Physicians' Desk Reference*, 54$^{th}$ edition, Medical Economics Company, 2000. The dosage ranges for a compound of the invention in these combinations are the same as those set forth above.

Abbreviations used in the instant specification, particularly the Schemes and Examples, include the following:
AIDS=acquired immunodeficiency syndrome
ARC=AIDS related complex
Bn=benzyl
BOP=benzotriazol-1-yloxytris-(dimethylamino)phosphonium hexafluorophosphate
CBZ=carbobenzoxy (alternatively, benzyloxycarbonyl)
DMAP=dimethylaminopyridine
DMF=dimethylformamide
DMSO=dimethyl sulfoxide
EDC or EDAC=1-ethyl-3-(3-dimethylaminopropyl) carbodiimide
ES-MS=eletron spray mass spectroscopy
Et=ethyl
FT ICR=fourier transform ion cyclotron resonance
Hal=halide
HIV=human immunodeficiency virus
HOBt=1-hydroxy benzotriazole hydrate
HPLC=high performance liquid chromatography
LC=liquid chromatography
Me=methyl
MS=mass spectroscopy
NBS=N-bromosuccinimide
NMR=nuclear magnetic resonance
TFA=trifluoroacetic acid
THF=tetrahydrofuran The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

The compounds of the present invention, 8,9-dihydroxy-dihydropyridopyrazine-1,6-diones and 8,9-dihydroxypyridopyrazine-1,6-diones, can be prepared by subjecting 1-alkyl-4-acyl piperazin-2-ones and 1-alkyl-4-acyl-3,4-dihydropyrazine-2(1H)-ones, respectively, to an oxalation-cyclization sequence. Scheme 1 depicts the general approach to the preparation of compounds of Formula (I). In Scheme 1, piperazin-2-one 1-1 is treated with oxalate 1-2 in the presence of base (e.g., lithium or sodium bis(trimethylsilyl)amide, or lithium diisopropylamide) at low temperature (e.g., from about 0 to about 25° C.) in an anhydrous non-protic solvent (e.g., DMF) to give a dihydroxypyridopyrazinedione of Formula (I). Scheme 2 exemplifies the same approach for the preparation of compounds of Formula (II). An analogous procedure can be used to prepare compounds of Formula (III) as earlier defined and described.

SCHEME 1

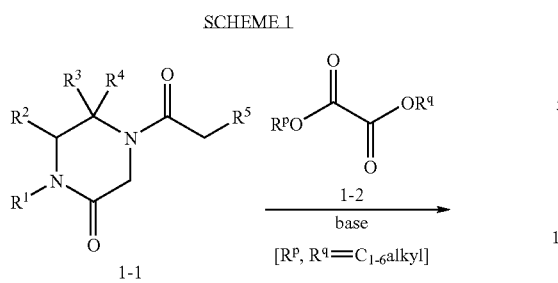

Compound I

SCHEME 2

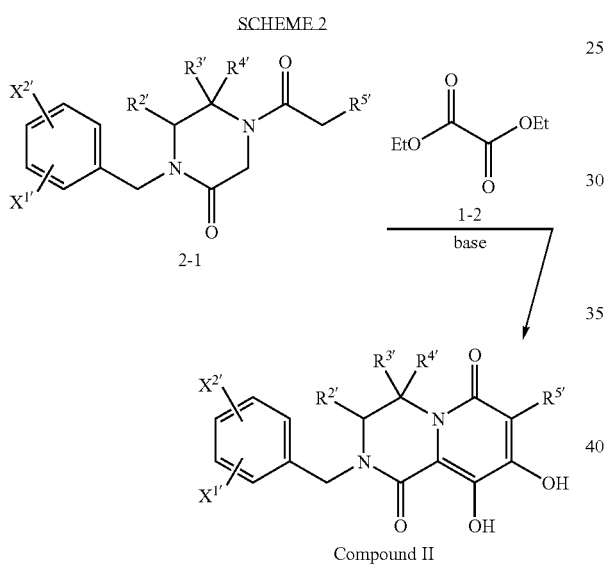

Compound II

1-Alkyl-4-acyl piperazin-2-ones of formula 1-1 can be prepared by alkylating a piperazin-2-one having a protective group on the 4-piperazinyl nitrogen, deprotecting the alkylated product, and then acylating with a suitable acylating agent to introduce $R^5$. The protection and deprotection of the amine in the piperazin-2-one can be accomplished using conventional amine protecting groups, such as those described in *Protective Groups in Organic Chemistry,* ed. J. F. W. McOmie, Plenum Press, 1973 and in T. W. Greene & P. G. M. Wuts, *Protective Groups in Organic Synthesis,* John Wiley & Sons, 1991. Further description of the preparation of piperazin-2-ones 1-1 via this chemistry is provided in Bernotas et al., *Tetrahedron Lett.* 1996, 7339; Saari et al., *J. Med. Chem.* 1990, 2590; Sugihara et al., *J. Med. Chem.* 1998, 489. This method is exemplified in Scheme 3 for the preparation of compound 2-1, wherein CBZ-protected piperazin-2-one 3-1 is alkylated with benzyl halide (e.g., benyl bromide) 3-2 in the presence of a base (e.g., in the presence of Li or Na bis (trimethylsilyl)amide or Li diisopropylamide at 0-25° C. in an anhydrous non-protic solvent such as DMF), and the alkylated product 3-3 is then treated with a reducing agent (e.g., $H_2$ over Pd/C) to remove the CBZ protective group. The deprotected product is then acylated with anhydride 3-4 to afford 2-1. Further description of this chemistry can be found in Wei et al., *Bioorg. Med. Chem.* 2000, 1737. Compound 3-1 can be prepared using methods described in Choi et al., *J. Med. Chem.* 1999, 3647; Najman-Bronzewska et al., *Pharmazie* 1997, 198; Fryer et al., *J. Org. Chem.* 1991, 3715, or routine variations thereof.

SCHEME 3

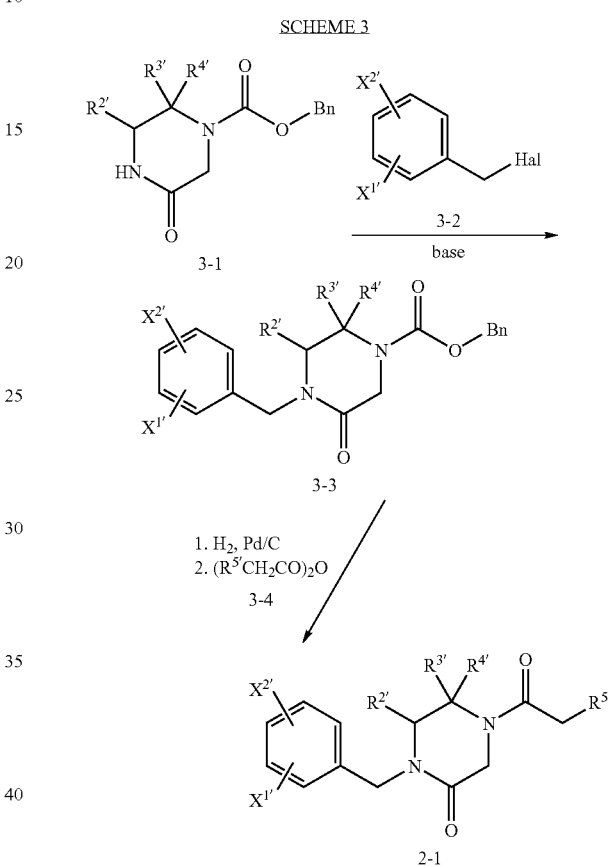

Other methods for preparing piperazin-2-ones 1-1 are exemplified in Schemes 4 and 5 showing the preparation of piperazin-2-ones 2-1 and 5-4 respectively. (Note: Piperazin-2-one 5-4 is equivalent to 2-1 having $R^{2'}=R^{3'}=R^{4'}=H$.) In Scheme 4, 4-acylpiperazin-2-one 4-1 is alkylated with benzyl halide (e.g., benzyl bromide) 3-2 in the presence of a base such as Li or Na bis(trimethylsilyl)amide or Li diisopropylamide at low temperature (e.g., 0 to 25° C.) in an anhydrous non-protic solvent such as DMF. Further description of this chemistry can be found in Hori et al., *Chem. Pharm. Bull.* 1981, 1594. In Scheme 5, N-(2,2-dimethoxyethyl)-N-benzylamine is obtained by reductive alkylation of the corresponding benzaldehyde and dimethoxyethylamine. The alkylation product is acylated with N-acyl-glycine with standard coupling reagents (eg. EDC, BOP, etc). Treatment of the acylation product with acid (e.g., $MeSO_3H$ in $CH_2Cl_2$, Kim et al., *Heterocycles* 1998, 2279; aqueous TFA, Horwell et al., *Tetrahedron* 1998, 4591; p-TsOH in toluene, Uchida et al., *Chem. Pharm. Bull.* 1997, 1228; HCl-acetonitrile, Kurihara et al., *Heterocycles* 1982, 191) provided the cyclization product, which was catalytically hydrogenated to produce 4-acyl-1-(benzyl)piperazin-2-one 5-4.

SCHEME 4

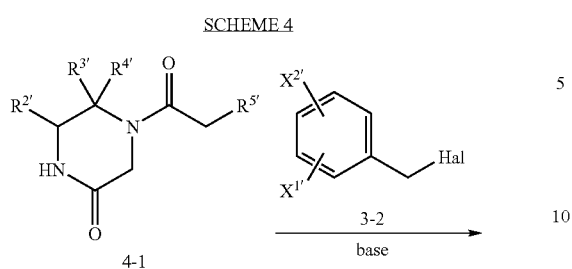

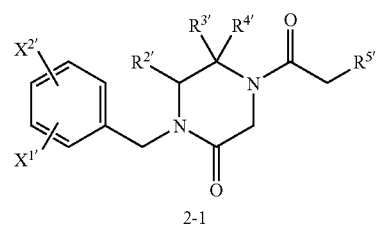

SCHEME 5

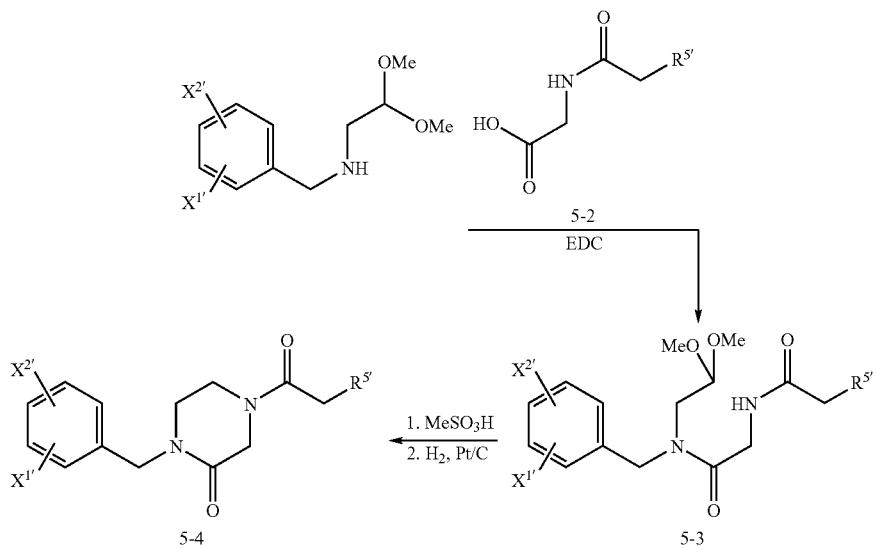

Scheme 6 illustrates a method for introducing functional groups at the 7-position of pyridopyrazine ring subsequent to the preparation of the dihydroxypyridopyrazinedione. As shown in Part A of Scheme 6, halogen can be introduced by treating the dihydroxypyridopyrazinedione 6-1 with a suitable halogenating agent (e.g., $Br_2$, NBS, ICl, etc). Further description of this chemistry can be found in March, *Advanced Organic Chemistry*, 531-534, 4th edition. Part B of Scheme 6 shows the introduction of an alkylamino group via the Mannich reaction, which is described in March, *Advanced Organic Chemistry*, 900-902, 4th edition. In Part B, dihydroxypyridopyrazinedione 6-1 is treated with a mixture of an aldehyde and a nucleophilic secondary amine in an alcoholic solution to provide the 7-aminoalkylated dihydroxypyridopyrazinedione 6-3.

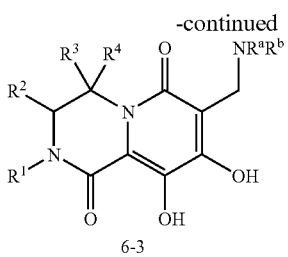

SCHEME 6

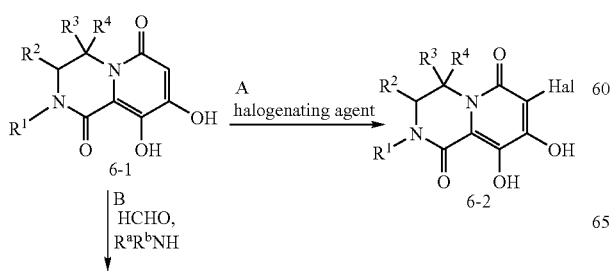

Scheme 7 depicts a method for preparing dihydroxypyridopyrazine-1,6-diones embraced by Formula (I) of the present invention. In Scheme 7, N-(2,2-dimethoxyethyl)-N-alkylamine is acylated with N-acyl-glycine with standard coupling reagents (eg. EDC, BOP, etc). Treatment of the acylation product 7-1 with acid (suitable acids include those disclosed above in the discussion of Scheme 5) will afford 4-acylpyrazin-2-one 7-2, which can be cyclized to provide dihydroxypyridopyrazinedione 7-3 via the oxalation-cyclization procedure depicted in Schemes 1 and 2.

SCHEME 7

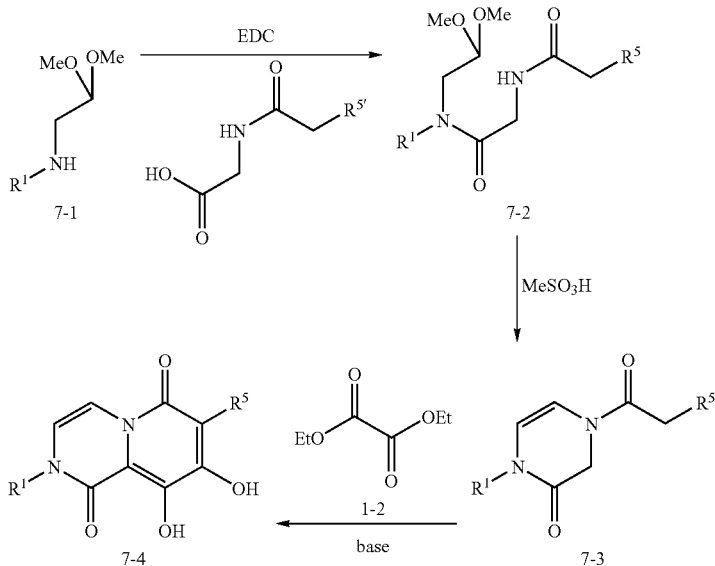

Scheme 8 shows a method for preparing dihydroxydihydropyrido-pyrazine-1,6-diones having an alkyl or substituted alkyl at the 4-position of the ring. In Scheme 8, treatment of alkyl (2-substituted aziridin-1-yl)acetate 8-1 with benzylamine 8-2 in the presence of borontrifluoride etherate provided the 5-substituted 1-benzylpiperazin-2-one 8-3. Acylation of the piperazinone, followed by the oxalation-cyclization procedure depicted in Scheme 1 provided the 4-substituted dihydroxydihydropyrido-pyrazine-1,6-diones 8-5. Note that in the case where $R^{4'}$=benzyloxymethyl, compound 8-5 can be hydrogenated (e.g., $H_2$ over Pd) to afford $R^{4'}$=hydroxymethyl.

SCHEME 8

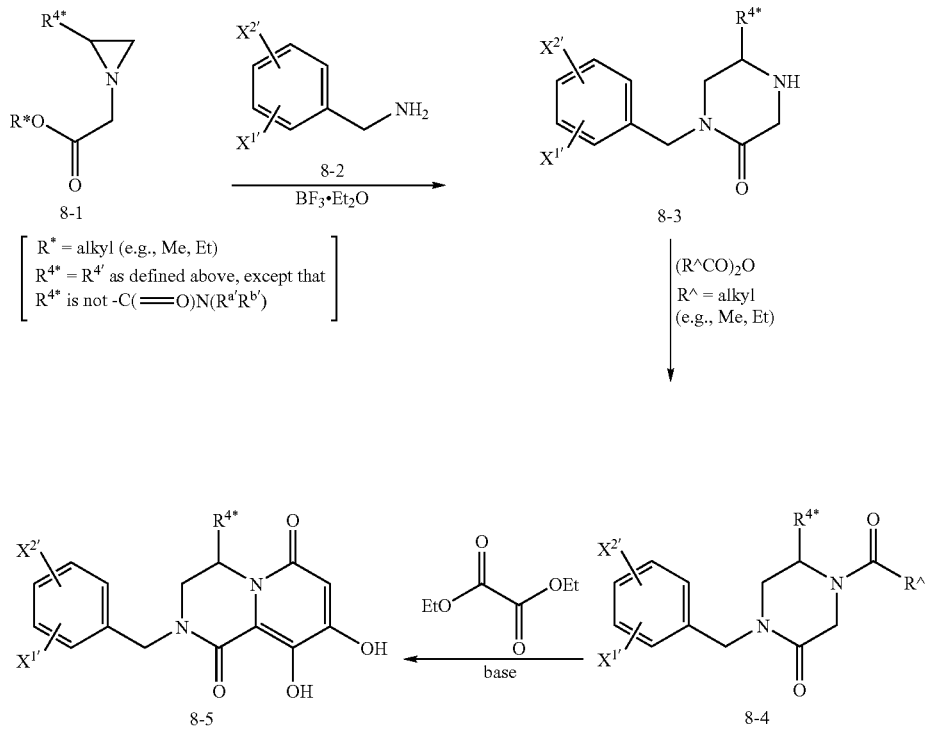

Scheme 9 shows a method for preparing dihydroxydihydropyrido-pyrazine-1,6-diones having an aminocarbonyl substituent at the 4-position of the ring. In Scheme 9, the hydroxymethylpiperazinone 9-1 was oxidized with an oxidizing reagent such as Jones reagent. The resulting acid 9-2 was converted to the corresponding amide 9-3 with coupling reagent such as EDC in the presence of an amine. Treatment of 9-3 with the oxalation-cyclization procedure depicted in Scheme 1 can provide the amide substituted dihydroxydihydropyrido-pyrazine-1,6-diones 9-4.

SCHEME 9

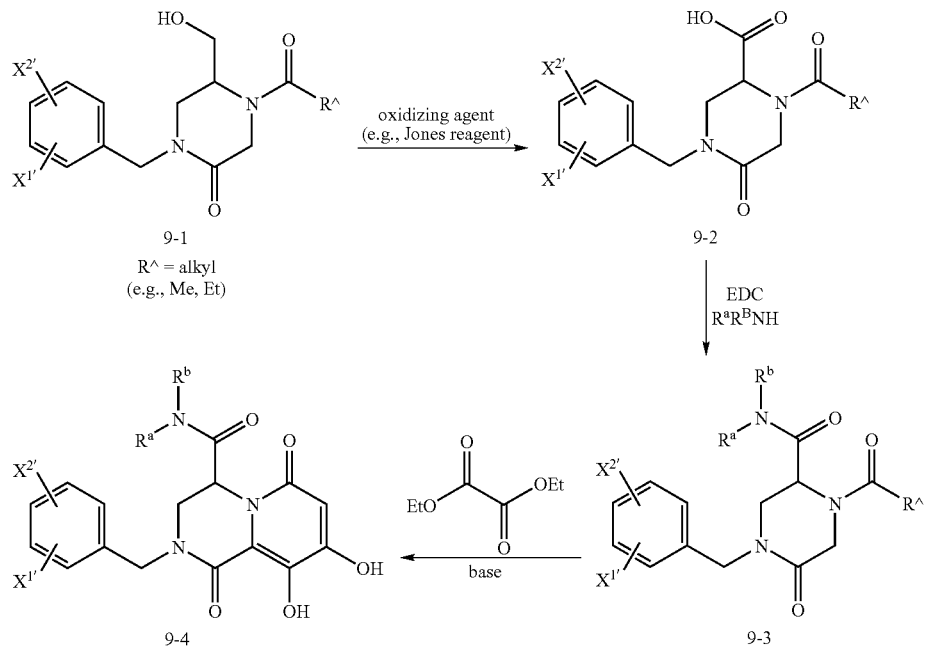

Scheme 10 depicts a method for preparing dihydroxydihydropyrido-pyrazine-1,6-diones having a heterocyclylmethyl substituent at the 4-position of the ring. According to Scheme 10, the hydroxymethylpiperazinone 10-1 can be treated with heterocyclic sulfonamides or amide in the presence of coupling reagent such as cyanomethylene tri-n-butylphosphorane or diethylazodicarboxylate-triphenylphosphine to provide the 4-heterocyclic-methyl susbtituted piperazin-2-one 10-2. Treatment of 10-2 with the oxalation-cyclization procedure depicted in Scheme 1 can provide the heterocyclicmethyl susbtituted dihydroxydihydropyrido-pyrazine-1,6-diones 10-3.

SCHEME 10

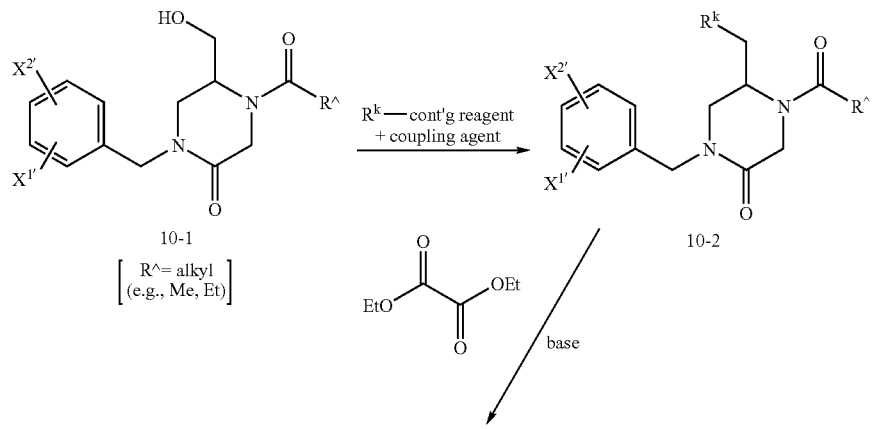

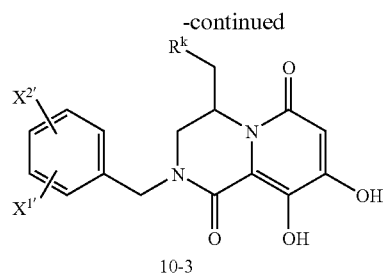

10-3

Scheme 11 depicts a method for preparing 4,5-dihydroxy-tetrahydrocyclopropapyrido-pyrazine-3,7-diones, wherein 3,4-dihydropyrazine 11-1 is cyclopropanated with a cyclopropanation reagent such as ethyl diazoacetate and copper bronze. The resulting ester 11-2 can be treated with a reducing agent (e.g., sodium borohydride) to proivee the corresponding alcohol 11-3, which can be treated with an alkylating reagent (e.g., benzyl bromide or an alkyl halide such as methyl iodide) and a base (e.g., NaH) to afford alkylation product 11-4. Subjecting 11-4 to the oxalation-cyclization procedure depicted in Scheme 1 can then proivde the desired 4,5-dihydroxy-tetrahydrocyclopropapyrido-pyrazine-3,7-dione 11-5.

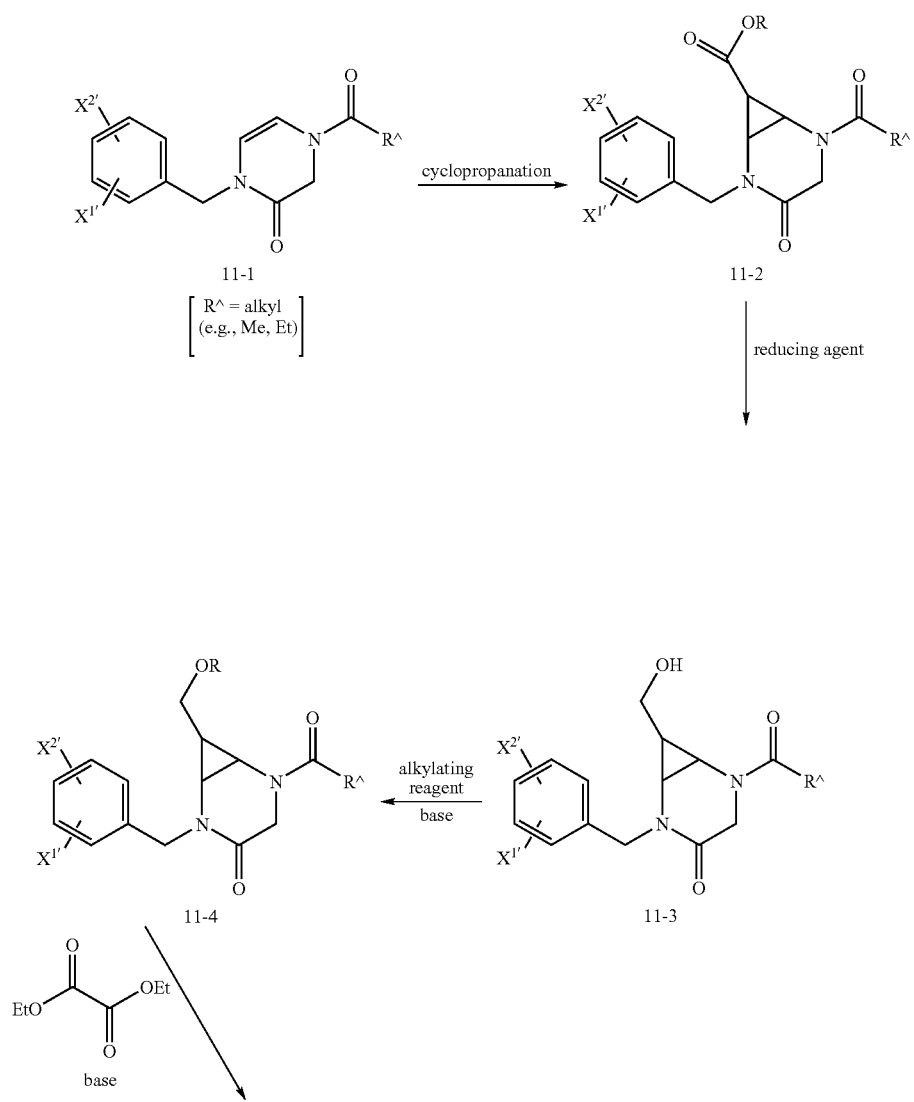

-continued

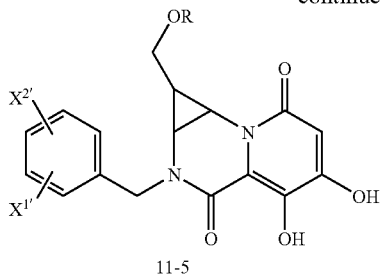

11-5

In the processes for preparing compounds of the present invention set forth in the foregoing schemes, functional groups in various moieties and substituents may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 1991. The protective groups may be removed at a convenient subsequent stage using methods known in the art.

The following examples serve only to illustrate the invention and its practice. The examples are not to be construed as limitations on the scope or spirit of the invention.

EXAMPLE 1

2-Benzyl-8,9-dihydroxy-3,4-dihydro-2H-pyrido[1,2-a]pyrazine-1,6-dione

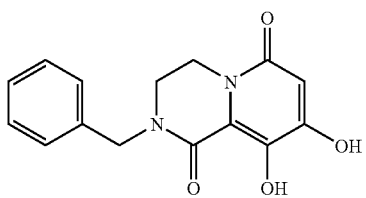

Step 1: Benzyl 4-benzyl-3-oxopiperazine-1-carboxylate

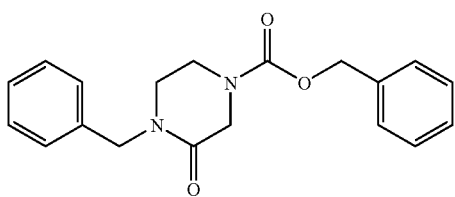

To a cold (0° C.) solution of benzyl 3-oxopiperazine-1-carboxylate (4.7 g, 20 mmol) in DMF (75 mL) under an atmosphere of nitrogen, a solution of lithium bis(trimethylsilyl)amide in THF (24 mL, 24 mmol) was added and stirred at the temperature for 30 min. The resultant solution was treated with benzyl bromide (2.9 mL, 24 mmol), and stirred at room temperature overnight. The product mixture was concentrated under vacuum, and the residue partitioned between aqueous HCl and ethyl acetate. The organic extracted was washed with brine, dried over anhydrous magnesium sulfate, filtered, and concentrated under vacuum. The residue was subjected to column chromatography on silica gel eluting with a 50-50 mixture of ethyl acetate and hexane. Collection and concentration of appropriate fractions provided the benzylated product.

$^1$H NMR (400 MHz, CDCl$_3$) δ 7.4-7.2 (m, 10H), 5.15 (s, 2H), 4.63 (s, 2H), 4.25 (s, 2H), 3.66 (br t, J=5.3 Hz, 2H), 3.27 (br s, 2H).

ES MS M+1=325

Step 2: 4-Acetyl-1-benzylpiperazin-2-one

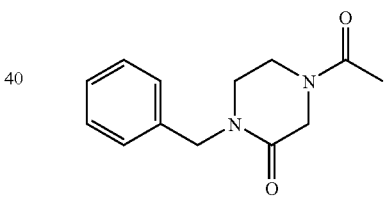

A mixture of benzyl 4-benzyl-3-oxopiperazine-1-carboxylate (4.7 g, 14.5 mmol) and 10% Pd/C (0.47 g) in ethanol (150 mL) was stirred under an atmosphere of hydrogen (1 atm) at room temperature overnight. The product mixture was filtered through a pad of Celite, and concentrated under vacuum to provide 1-benzylpiperazin-2-one. A portion of the resultant oil (1.06 g, 5.5 mmol) was treated with a mixture of N,N-diisopropylethylamine (1.46 mL, 8.3 mmol), DMAP (68 mg, 0.55 mmol), and acetic anhydride (0.73 mL, 7.8 mmol) in methylene chloride (30 mL) at 0° C. After stirring at room temperature overnight, the resultant mixture was concentrated and the residue was subjected to column chromatography on silica gel eluting with a 10-90 mixture of methanol and ethyl acetate. Collection and concentration of appropriate fractions provided the title piperazinone.

$^1$H NMR (400 MHz, CDCl$_3$) ~2:1 mixture of rotomers δ 7.4-7.2 (m, 5H), 4.64 (s, 2/3H), 4.63 (s, 1 1/3H), 4.32 (s, 2/3H), 4.21 (s, 1 1/3H), 3.76 (br t, J=5.3 Hz, 1 1/3H), 3.63 (br t, J=5.3 Hz, 2/3H), 3.30 (br t, J=5.3 Hz, 2/3H), 3.27 (br t, J=5.3 Hz, 1 1/3H), 2.11 (s, 2H), 2.10 (s, 1H).

ES MS M+1=233

Step 3: 2-Benzyl-8,9-dihydroxy-3,4-dihydro-2H-pyrido[1,2-a]pyrazine-1,6-dione To a cold (0° C.) solution of 4-acetyl-1-benzylpiperazin-2-one (0.49 g, 2.1 mmol) in DMF (10 mL) under an atmosphere of nitrogen, a solution of lithium bis(trimethylsilyl)amide in THF (2.5 mL, 2.5 mmol) was added and stirred at the temperature for 30 min. The resultant solution was treated with diethyl oxalate (0.43 mL, 3.1 mmol), and stirred at room temperature overnight. The resultant mixture was then treated with additional lithium bis(trimethylsilyl)amide in THF (10 mL, 10 mmol) and stirred at room temperature for 6 h. The product mixture was concentrated under vacuum, and the residue partitioned between aqueous HCl and ethyl acetate. The organic extract was dried over anhydrous magnesium sulfate, filtered, and concentrated under vacuum. The residue was subjected to HPLC purification on C-18 stationary phase eluted with water/acetonitrile/TFA mobile phase. Collection and lyophilization of appropriate fractions provided the title compound as white solid.

$^1$H NMR (400 MHz, DMSO-$d_6$) δ 12.33 (s, 1H), 11.07 (br s, 1H), 7.39-7.25 (m, 5H), 5.93 (s, 1H), 4.70 (s, 2H), 3.97 (t, J=5.5 Hz, 2H), 3.56 (t, J=5.5 Hz, 2H).

ES MS M+1=287

EXAMPLE 2

2-(4-Fluorobenzyl)-8,9-dihydroxy-3,4-dihydro-2H-pyrido[1,2-a]pyrazine-1,6-dione

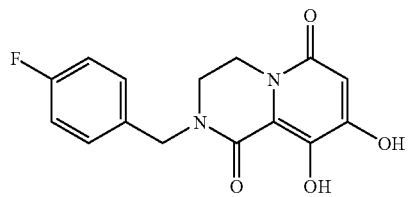

Step 1: N-(2,2-Dimethoxyethyl)-N-(4-fluorobenzyl)amine

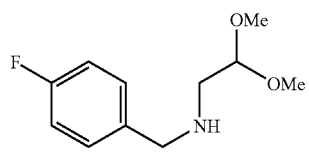

A mixture of 4-fluorobenzaldehyde (227.6 g, 1.83 mol) and dimethoxy-ethylamine (192.6 g, 1.83 mol) in methanol (2.5 L) was heated at 65° C. for 1.5 h. The solution was allowed to cool to room temperature overnight and treated with sodium borohydride (47.6 g 1.26 mol) in portions over a period of 2 h. The resultant mixture was stirred at room temperature for 3 h and quenched with water (1 L). The product mixture was concentrated to about 1 L and extracted with diethyl ether (3×). The ethereal extracts were combined, washed with brine, dried over anhydrous sodium sulfate, filtered, and concentrated under vacuum to provide the title compound as yellow oil.

$^1$H NMR (400 MHz, CDCl$_3$) δ 7.28 (dd, J=5.5, 8.6 Hz, 2H), 7.00 (t, J=6.8 Hz, 2H), 4.48 (t, J=5.5 Hz, 1H), 3.77 (s, 21H), 3.37 (s, 61H), 2.73 (d, J=5.5 Hz, 2H).

ES MS M+1=214

Step 2: N$^2$-acetyl-N$^1$-(2,2-dimethoxyethyl)-N$^1$-(4-fluorobenzyl)glycinamide

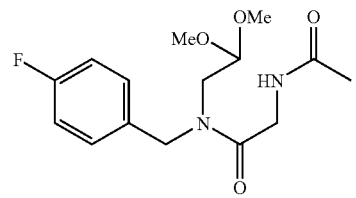

To a solution of N-(2,2-dimethoxyethyl)-N-(4-fluorobenzyl)amine (366.5 g, 1.72 mol), N-acetylglycine (213.7 g, 1.83 mol), EDC (350.0 g, 1.83 mol), and HOBt (29.1 g, 0.19 mol) in anhydrous DMF (2.5 L), N,N-diisopropylethylamine (~250 mL) was added until the solution is about pH 8. The reaction mixture was stirred at room temperature overnight and concentrated under vacuum. The residue was partitioned between dichloromethane (4 L) and water (1 L). The organic extract was washed with brine, dried over anhydrous sodium sulfate, filtered, and concentrated under vacuum to provide the title compound.

$^1$H NMR (400 MHz, CDCl$_3$) ~1:1 mixture of rotomers δ 7.27-6.99 (m, 4H), 6.57 (br s, 1H), 4.67 (s, 1H), 4.58 (s, 1H), 4.52 (t, J=5.3 Hz, 0.5H), 4.32 (t, J=5.3 Hz, 0.5H), 4.20 (d, J=4.0 Hz, 1H), 4.11 (d, J=4.0 Hz, 1H), 3.46 (d, J=5.3 Hz, 1H), 3.39 (s, 3H), 3.35 (s, 3H), 3.31 (d, J=5.3 Hz, 1H), 2.06 (s, 1.5H), 2.04 (s, 1.5H).

ES MS M-OCH$_3$=281

Step 3: 4-Acetyl-1-(4-fluorobenzyl)-3,4-dihydropyrazin-2(1H)-one

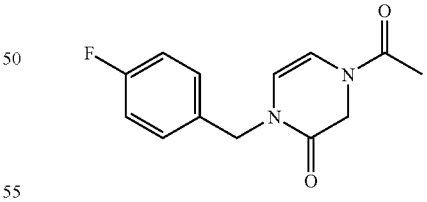

To a solution of methanesulfonic acid (314 g) in dichloromethane (10 L) at room temperature, a solution of N$^2$-acetyl-N$^1$-(2,2-dimethoxyethyl)-N$^1$-(4-fluoro-benzyl)glycinamide (438 g, 1.07 mol) in dichloromethane (2 L) was added slowly over a period of 2 h. The reaction mixture was stirred at room temperature overnight and treated with saturated aqueous sodium carbonate (3 L). The organic extract was washed with brine, dried over anhydrous sodium sulfate, filtered, and concentrated under vacuum. To the residual oil, ethyl acetate (1 L) was added and stirred at room temperature.

The solid precipitated was filtered to provide the title compound.

¹H NMR (400 MHz, CDCl₃) ~5:1 mixture of rotomers δ 7.3-7.2 (m, 2H), 7.1-7.0 (m, 2H), 6.70(d, J=6.4 Hz, 1/5H), 6.11(d, J=6.4 Hz, 4/5H), 5.61( d, J=6.4 Hz, 1/5H), 5.53(d, J=6.4 Hz, 4/5H), 4.68 (s, 1 3/5H), 4.66 (s, 2/5H), 4.42 (s, 1 3/5H), 4.36 (s, 2/5H), 2.16 (s, 3H).

ES MS M+1=249

Step 4: 4-Acetyl-1-(4-fluorobenzyl)piperazin-2-one

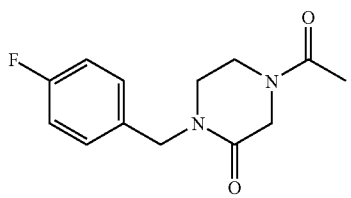

A mixture of 4-acetyl-1-(4-fluorobenzyl)-3,4-dihydropyrazin-2(1H)-one (141 g, 0.57 mol) and 5% Pd/C (10.4 g) in ethanol (500 mL) was stirred under an atmosphere of hydrogen (1 atm) at room temperature overnight. The product mixture was filtered through a pad of Celite, and concentrated under vacuum to provide the title compound. Residual ethanol was removed by co-evaporation with toluene (3×) under vacuum. The resultant oil solidify on standing and was used in the next step without further purification.

¹H NMR (400 MHz, CDCl₃) ~2:1 mixture of rotomers δ 7.3 (m, 2H), 7.0 (m, 2H), 4.58 (s, 2H), 4.32 (s, 2/3H), 4.20 (s, 1 1/3H), 3.77 (br t, J=5.4 Hz, 1 1/3 H), 3.63 (br t, J=5.4 Hz,2/3 H), 3.30 (br t, J=5.4 Hz,2/3 H), 3.26 (br t, J=5.4 Hz, 1 1/3H), 2.12 (s, 2H), 2.11 (s, 1H).

ES MS M+1=251

Step 5: 2-(4-Fluorobenzyl)-8,9-dihydroxy-3,4-dihydro-2H-pyrido[1,2-a]pyrazine-1,6-dione To a cold (0° C.) solution of 4-acetyl-1-(4-fluorobenzyl) piperazin-2-one (30.6 g, 122 mmol) in DMF (700 mL) under an atmosphere of nitrogen, a solution of sodium bis(trimethylsilyl)amide in THF (2 M, 73 mL, 146 mmol) was added and stirred at the temperature for 30 min. The resultant solution was treated with diethyl oxalate (16.7 mL, 123 mmol), and stirred at room temperature overnight. The resultant mixture was then treated with additional sodium bis(trimethylsilyl) amide in THF (2 M, 73 mL, 146 mmol) and stirred at room temperature for 4 h. The product mixture was concentrated under vacuum, and the residue treated with a mixture of aqueous HCl and ethyl acetate. The resultant precipitate was obtained by filtration to provide the title compound.

¹H NMR (400 MHz, DMSO-d₆) δ 12.31 (s, 1H), 11.07 (br s, 1H), 7.40 (dd, J=8.3, 5.8 Hz, 2H), 7.20 (t, J=8.3 Hz, 2H), 5.98 (s, 1H), 4.68 (s, 2H), 3.97 (t, J=5.3 Hz, 2H), 3.56 (t, J=5.3 Hz, 2H).

ES MS M+1=305

EXAMPLE 3

2-(4-Fluorobenzyl)-8,9-dihydroxy-7-methyl-3,4-dihydro-2H-pyrido[1,2-a]pyrazine-1,6-dione

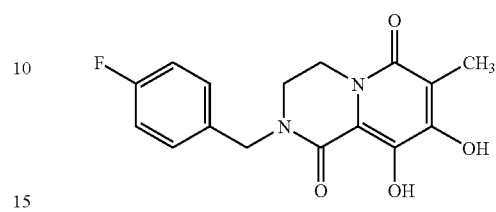

The title compound was prepared using a procedure similar to that described in Example 1, except that benzyl bromide (Step 1) was substituted with 4-fluorobenzyl bromide, and acetic anhydride (Step 2) was substituted with propionic anhydride.

¹H NMR (400 MHz, CDCl₃) δ 12.50 (s, 1H1), 7.4-7.0 (m, 4H), 6.40 (br s, 1H), 4.74 (s, 2H), 4.22 (t, J=5.5 Hz, 2H), 3.55 (t, J=5.5 Hz, 2H), 2.17 (s, 3H).

ES MS M+1=319

EXAMPLE 4

2-(4-Fluorobenzyl)-8,9-dihydroxy-7-bromo-3,4-dihydro-2H-pyrido[1,2-a]pyrazine-1,6-dione

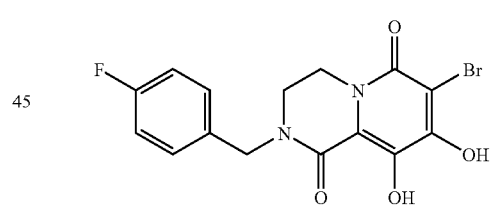

To a suspension of 2-(4-fluorobenzyl)-8,9-dihydroxy-3,4-dihydro-2H-pyrido[1,2-a]pyrazine-1,6-dione (0.1 g, 0.33 mmol) in chloroform (5 mL), N-bromo-succinimide (64 mg, 0.36 mmol) was added and stirred at room temperature overnight. The product mixture was concentrated and the residue was subjected to HPLC purification on C-18 stationary phase eluted with water/acetonitrile/TFA mobile phase. Collection and lyophilization of appropriate fractions provided the title compound as white solid.

¹H NMR (400 MHz, DMSO-d₆) δ 12.69 (s, 1H), 11.62 (br s, 1H), 7.41 (dd, J=5.8, 8.4 Hz, 2H), 7.20 (t, J=8.8 Hz, 2H), 4.69 (s, 2H), 4.07 (t, J=5.3 Hz, 2H), 3.59 (t, J=5.3 Hz, 2H).

ES MS M+1=383/385

EXAMPLE 5

2-(4-Fluorobenzyl)-8,9-dihydroxy-7-iodo-3,4-dihydro-2H-pyrido[1,2-a]pyrazine-1,6-dione

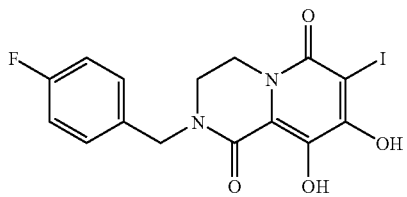

To a suspension of 2-(4-fluorobenzyl)-8,9-dihydroxy-3,4-dihydro-2H-pyrido[1,2-a]pyrazine-1,6-dione (5 g, 16.4 mmol) in methylene chloride (300 mL) at room temperature, a solution of iodine monochloride (2.8 g, 17.2 mmol) in methylene chloride (50 mL) was added. The suspension was stirred at room temperature overnight and concentrated under vacuum. The residue was dissolved in ethyl acetate and washed subsequently with an aqueous solution of sodium metabisulfite and brine. The organic extract was dried over anhydrous magnesium sulfate, filtered, concentrated. The residual solid was stirred in diethyl ether overnight, and collected by filtration.

$^1$H NMR (400 MHz, DMSO-$d_6$) δ 12.65 (s, 1H), 11.82 (s, 1H), 7.41 (dd, J=6.0, 8.4 Hz, 2H), 7.20 (t, J=8.8 Hz, 2H), 4.69 (s, 2H), 4.07 (t, J=5.3 Hz, 2H), 3.59 (t, J=5.3 Hz, 2H).

ES MS M+1=431

EXAMPLE 6

2-(3-Chlorobenzyl)-8,9-dihydroxy-3,4-dihydro-2H-pyrido[1,2-a]pyrazine-1,6-dione

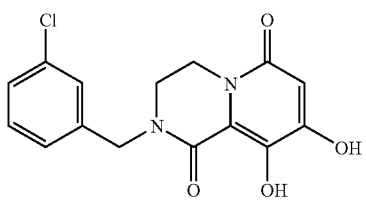

Step 1: 4-Acetylpiperazin-2-one

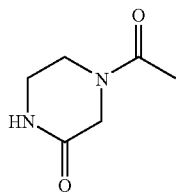

To a cold (0° C.) solution of piperazin-2-one (2.50 g, 24.9 mmol) and N,N-diisopropylethylamine (4.78 mL, 27.5 mmol) in methylene chloride (50 mL) under an atmosphere of nitrogen, acetic anhydride (2.47 mL, 26.2 mmol) was added and stirred at the temperature for overnight. The resultant solution was concentrated under vacuum. The residue was subjected to column chromatography on silica gel eluting with a 90:10:1 mixture of chloroform, methanol, and ammonium hydroxide. Collection and concentration of appropriate fractions provided the title product.

$^1$H NMR (400 MHz, CDCl$_3$) ~2:3 mixture of rotomers δ 6.81 (br s, 2/5H), 6.59 (br s, 3/5 H), 4.25 (s, 4/5H), 4.13 (s, 1 1/5 H), 3.82 (t, J=5.4 Hz, 11/5 H), 3.67 (t, J=5.4 Hz, 4/5 H), 3.46 (m, 4/5 H), 3.40 (m, 1 1/5 H), 2.15 (s, 1H), 2.12 (s, 2H).

ES MS M+1=143

Step 2: 2-(3-chlorobenzyl)-8,9-dihydroxy-3,4-dihydro-2H-pyrido[1,2-a]pyrazine-1,6-dione To a cold (0° C.) solution of 4-acetylpiperazin-2-one (1.0 g, 7.0 mmol) in DMF (75 mL) under an atmosphere of nitrogen, a solution of lithium bis(trimethylsilyl)-amide in THF (7.7 mL, 7.7 mmol) was added and stirred at the temperature for 30 min. The resultant solution was treated with 3-chlorobenzyl bromide (0.92 mL, 7.0 mmol), and stirred at room temperature overnight. The resultant mixture was cooled to 0° C., treated with a solution of lithium bis(trimethylsilyl) amide in THF (8.4 mL, 8.4 mmol) and stirred for 30 min, and then treated with diethyl oxalate (0.96 mL, 7.0 mmol). The resultant mixture was stirred at room temperature overnight. Additional solution of lithium bis(trimethylsilyl)amide in THF (16.8 mL, 16.8 mmol) was added and stirred for 4 hrs. The product mixture was concentrated under vacuum, and the residue was treated with a mixture of aqueous HCl and ethyl acetate. The white solid precipitated was collected by filtration and was subjected to HPLC purification on C-18 stationary phase eluted with water/acetonitrile/TFA mobile phase. Collection and lyophilization of appropriate fractions provided the title compound.

$^1$H NMR (400 MHz, DMSO-$d_6$) δ 12.25 (s, 1H), 11.07 (br s, 1H), 7.44-7.31 (m, 4H), 5.93 (s, 1H), 4.69 (s, 2H), 3.98 (t, J=5.5 Hz, 2H), 3.59 (t, J=5.5 Hz, 2H).

ES MS M+1=322

EXAMPLE 7

2-(4-Chlorobenzyl)-8,9-dihydroxy-3,4-dihydro-2H-pyrido[1,2-a]pyrazine-1,6-dione

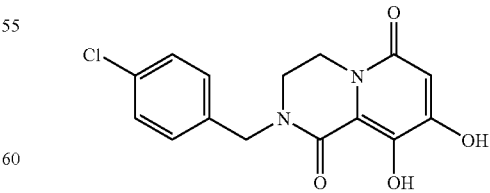

The title compound was prepared using a procedure similar to that described in Example 6, except that 3-chlorobenzyl bromide (Step 2) was substituted with 4-chlorobenzyl bromide.

$^1$H NMR (400 MHz, DMSO-d$_6$) δ 12.28 (s, 1H), 11.10 (br s, 1H), 7.42 (t, J=8.6 Hz, 2H), 7.37 (t, J=8.6 Hz, 2H), 5.94 (s, 1H), 4.68 (s, 2H), 3.97 (t, J=6.1 Hz, 2H), 3.57 (t, J=6.1 Hz, 2H).

ES MS M+1=322

EXAMPLE 8

2-(3,4-Dichlorobenzyl)-8,9-dihydroxy-3,4-dihydro-2H-pyrido[1,2-a]pyrazine-1,6-dione

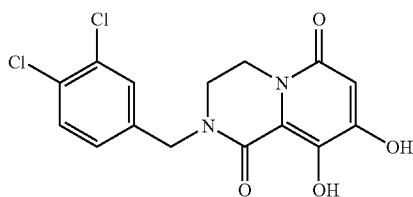

The title compound was prepared using a procedure similar to that described in Example 6, except that 3-chlorobenzyl bromide (Step 2) was substituted with 3,4-dichlorobenzyl bromide.

$^1$H NMR (400 MHz, DMSO-d$_6$) δ 12.22 (s, 1H), 11.09 (br s, 1H), 7.65 (d, J=2.0 Hz, 1H), 7.62 (d, J=8.3 Hz, 1H), 7.35 (dd, J=1.8, 8.8 Hz, 1H), 5.94 (s, 1H), 4.69 (s, 2H), 3.96 (t, J=5.3 Hz, 2H), 3.59 (t, J=5.3 Hz, 2H).

ES MS M+1=356

EXAMPLE 9

2-(3,4-Difluorobenzyl)-8,9-dihydroxy-3,4-dihydro-2H-pyrido[1,2-a]pyrazine-1,6-dione

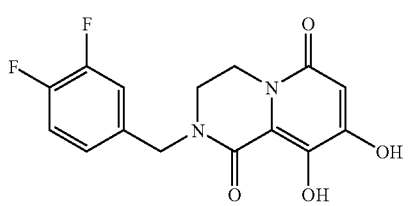

The title compound was prepared using a procedure similar to that described in Example 6, except that 3-chlorobenzyl bromide (Step 2) was substituted with 3,4-difluorobenzyl bromide.

$^1$H NMR (400 MHz, DMSO-d$_6$) δ 12.24 (s, 1H), 11.19 (br s, 1H), 7.48-7.39 (m, 2H), 7.23-7.20 (m, 1H), 6.00 (s, 1H), 4.68 (s, 2H), 3.99 (t, J=5.9 Hz, 2H), 3.59 (t, J=5.9 Hz, 2H).

ES MS M+1=323

EXAMPLE 10

2-(3-Chloro-4-fluorobenzyl)-8,9-dihydroxy-3,4-dihydro-2H-pyrido[1,2-a]pyrazine-1,6-dione

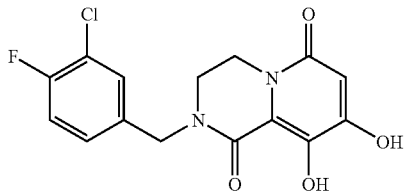

The title compound was prepared using a procedure similar to that described in Example 6, except that 3-chlorobenzyl bromide (Step 2) was substituted with 3-chloro4-fluorobenzyl bromide.

$^1$H NMR (400 MHz, DMSO-d$_6$) δ 12.23 (s, 1H), 11.05 (br s, 1H), 7.60 (d, J=7.0 Hz, 2H), 7.43-7.36 (m, 2H), 5.93 (s, 1H), 4.67 (s, 2H), 3.98 (t, J=5.6 Hz, 2H), 3.59 (t, J=5.6 Hz, 2H).

ES MS M+1=339

EXAMPLE 11

2-(4-Fluorobenzyl)-8,9-dihydroxy-7-(piperidin-1-ylmethyl)-3,4-dihydro-2H-pyrido[1,2-a]pyrazine-1,6-dione

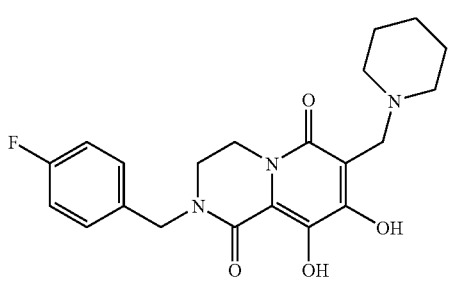

A mixture of 2-(4-fluorobenzyl)-8,9-dihydroxy-3,4-dihydro-2H-pyrido[1,2-a]pyrazine-1,6-dione (0.2 g, 0.66 mmol), piperidine (0.13 mL, 1.3 mmol), and formaldehyde (0.08 mL, 37% solution in water) in absolute ethanol (5 mL) was stirred at room temperature for 6 h. The product mixture was concentrated under vacuum, and the residue was subjected to HPLC purification on C-18 stationary phase eluted with water/acetonitrile/TFA mobile phase. Collection and lyophilization of appropriate fractions provided the title compound.

$^1$H NMR (400 MHz, DMSO-d$_6$) δ 12.62 (s, 1H), 11.91 (s, 1H), 7.41 (dd, J=5.8, 8.4 Hz, 2H), 7.22 (t, J=8.8 Hz, 2H), 4.72 (s, 2H), 4.08 (br s, 4H), 3.62 (t, J=5.5 Hz, 2H), 3.3 (br s, 2H), 2.9 (br s, 2H), 1.7 (br m, 6H).

ES MS M+1=402

EXAMPLE 12

2-(3-Chloro4-fluorobenzyl)-8,9-dihydroxy-7-(piperidin-1-ylmethyl)-3,4dihydro-2H-pyrido[1,2-a]pyrazine-1,6dione

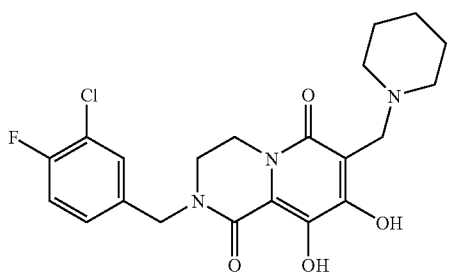

The title compound was prepared using a procedure similar to that described in Example 11, except that 2-(4-fluorobenzyl)-8,9-dihydroxy-3,4-dihydro-2H-pyrido[1,2-a]pyrazine-1,6-dione was substituted with 2-(3-chloro4-fluorobenzyl)-8,9-dihydroxy-3,4-dihydro-2H-pyrido[1,2-a]pyrazine-1,6-dione.

$^1$H NMR (400 MHz, DMSO-$d_6$) δ 12.54 (s, 1H), 11.95 (br s, 1H), 7.62 (br d, J=6.9 Hz, 1H), 7.45-7.40 (m, 2H), 4.71 (s, 21), 4.08 (br signal, 4H), 3.65 (t, J=5.5 Hz, 2H), 2.96 (br signal, 2H), 2.68 (br s, 2H), 2.33 (br s, 2H), 1.7 (br m, 6H).

ES MS M+1=436

EXAMPLE 13

2-(4-Fluorobenzyl)-8,9-dihydroxy-7-[(dimethylamino)methyl]-3,4-dihydro-2H-pyrido[1,2-a]pyrazine-1,6-dione

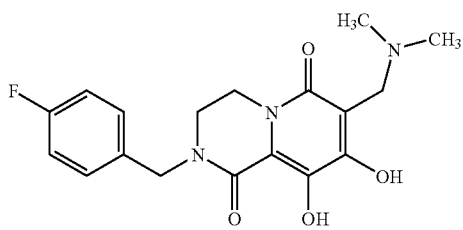

The title compound was prepared using a procedure similar to that described in Example 11, except that piperidine was substituted with dimethylamine.

$^1$H NMR (400 MHz, DMSO-$d_6$) δ 12.63 (s, 1H), 11.90 (br s, 1H), 7.41 (dd, J=6.0, 8.4 Hz, 2H), 7.21 (t, J=8.8 Hz, 2H), 4.72 (s, 2H), 4.22 (s, 2H), 4.08 (t, J=5.5 Hz, 2H), 3.63 (t, J=5.5 Hz, 2H), 2.74 (s, 6H).

ES MS M+1=362

EXAMPLE 14

2-(4-Fluorobenzyl)-8,9-dihydroxy-2H-pyrido[1,2-a]pyrazine-1,6-dione

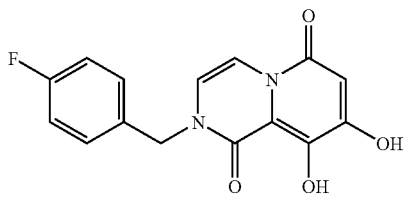

A mixture of anhydrous DMSO and sodium hydride (0.24 g, 60% oil dispersion, washed 3× with hexane) under an atmosphere of nitrogen was heated with stirring at 50° C. for 3 h. After cooling to room temperature, a solution of 4-acetyl-1-(4-fluorobenzyl)-3,4-dihydropyrazin-2(1H)-one (0.5 g, 2.0 mmol; Example 2, Step 3) in anhydrous DMSO (5 mL) was added over a period of 10 min and the resultant mixture stirred at room temperature for 30 min. The mixture was then treated with diethyl oxalate (0.29 mL, 2.1 mmol) and stirred at room temperature overnight. The product mixture was subjected to HPLC purification on C-18 stationary phase eluted with water/acetonitrile/TFA mobile phase. Collection and lyophilization of appropriate fractions provided the title compound.

$^1$H NMR (400 MHz, DMSO-$d_6$) δ 11.77 (s, 1H), 11.40 (s, 1H), 7.44 (dd, J=5.6, 8.1 Hz, 2H), 7.39 (d, J=6.4 Hz, 1H), 7.21 (t, J=8.1 Hz, 2H), 6.76 (d, J=6.4 Hz, 1H), 6.09 (s, 1H), 4.92 (s, 2H).

ES MS M+1=303

The title compound was also prepared as follows:

To a cold (0 C) solution of 4-acetyl-1-(4-fluorobenzyl)-3,4-dihydro-pyrazin-2(1H)-one (0.41 g, 1.65 mmol; Example 2, Step 3) in anhydrous DMF (16 mL) under an atmosphere of nitrogen, a solution of lithium bis(trimethylsilyl)amide in THF (3.3 mL, 3.3 mmol) was added and stirred at that temperature for 15 min. The resultant solution was treated with N,N'-dimethyloxy-N,N'-dimethyloxalamide (0.29 g, 1.65 mmol; J. Org. Chem. 1995, p. 5016) in one portion, allowed to warm to, and stirred at room temperature overnight. After 16 hrs. the resultant mixture was treated with additional lithium bis(trimethylsilyl)amide in THF (1.6 mL, 1.6 mmol) and stirred at room temperature for 1 h. The product mixture was concentrated under vacuum, and the dark brown residue was stirred in a mixture of 1M aqueous hydrochloric acid (75 mL) in ice for 15 min. The dark brown solid formed was isolated by filtration and air dried. The dried solid was washed with diethyl ether 2 times, air dried, then dried under vacuum to afford the crude product which was used without further purification in the preparation of the compound of Example 25.

EXAMPLE 15

2-Benzyl-8,9-dihydroxy-2H-pyrido[1,2-a]pyrazine-1,6-dione

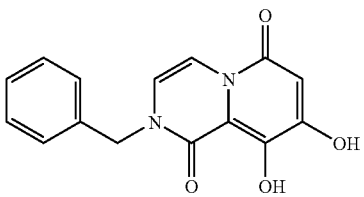

The title compound was prepared using procedures similar to that described in Examples 2 and 14, except that N-(2,2-dimethoxyethyl)-N-(4-fluoro-benzyl)amine (Example 2, Step 2) was substituted with N-benzylaminoacetaldehyde diethyl acetal.

$^1$H NMR (400 MHz, CDCl$_3$) δ 11.95 (s, 1H), 10.56 (br s, 1H), 7.52 (d, J=6.6 Hz, 1H), 7.4-7.3 (m, 5H), 6.33 (s, 1H), 6.22 (d, J=6.6 Hz, 1H), 4.92 (s, 2H).

ES MS M+1=285

EXAMPLE 16

2-(4-Fluorobenzyl)-8,9-dihydroxy-4-methyl-3,4-dihydro-2H-pyrido[1,2-a]pyrazine-1,6-dione

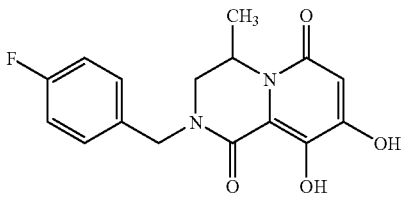

Step 1: Ethyl (2-methylaziridin-1-yl)acetate

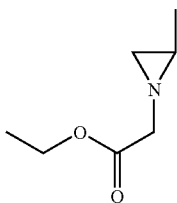

To a cold (−78° C.) solution of 2-methylaziridine (5.6 g, 99 mmol) and N,N-diisopropylethylamine (18.8 mL, 108 mmol) in dichloromethane (250 mL) under an atmosphere of nitrogen, ethyl bromoacetate (10 mL, 90 mmol) was added over a period of 1 h. The resultant mixture was allowed to slowly warm up and stirred at room temperature overnight. The resultant mixture was concentrated under vacuum, and the residue was suspended in chloroform. A stream of anhydrous ammonia gas was bubbled into the mixture with stirring for a period of 15 min. The resultant suspension was filtered, and the filtrate concentrated under vacuum. The residue was further treated with anhydrous diethyl ether and the milky solution filtered through a pad of Celite. The filtrate was concentrated under vacuum, and the residue subjected to distillation under reduced pressure (bp ~60° C., 18 torr) to provide the title compound as colorless oil.

$^1$H NMR (400 MHz, CDCl$_3$) δ 4.21 (q, J=7.1 Hz, 2H), 3.13 (d, J=16.1 Hz, 1H), 3.00 (d, J=16.1 Hz, 1H), 1.64 (d, J=3.7 Hz, 1H), 1.47 (m, 1H), 1.33 (d, J=6.2 Hz, 1H), 1.29 (t, J=7.1 Hz, 3H), 1.23 (d, J=5.5 Hz, 3H).

Step 2: 4-Acetyl-1-(4-fluorobenzyl)-5-methylpiperazin-2-one

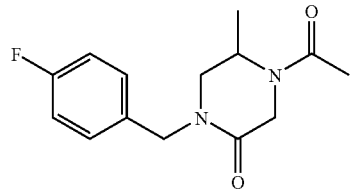

A mixture of ethyl (2-methylaziridin-1-yl)acetate (4.0 g, 28 mmol), 4-fluorobenzylamine (5.3 g, 42 mmol), and boron trifluoride etherate (0.5 mL) was heated in a sealed stainless steel vessel inside a Teflon liner at 95° C. for 60 h (*Bull. Chem. Soc. Jpn.* 1986, 59: 321). The resulting mixture was dissolved in dichloromethane (50 mL), cooled to 0° C., and treated with a mixture of triethylamine (13 mL, 95 mmol) and acetic anhydride (6.7 mL, 71 mmol). The reaction mixture was stirred at room temperature overnight, and extracted successively with saturated aqueous solution of sodium bicarbonate, dilute aqueous HCl, and brine. The organic extract was dried over anhydrous magnesium sulfate, filtered, and concentrated under vacuum. The residue was subjected to column chromatography on silica gel eluting with a mixture of 7-10% methanol in ethyl acetate. Collection and concentration of appropriate fractions provided the title piperazinone.

ES MS M+1=265

Step 3: 2-(4-Fluorobenzyl)-8,9-dihydroxy-4-methyl-3,4-dihydro-2H-pyrido[1,2-a]pyrazine-1,6-dione The title compound was prepared using a procedure similar to that described in Example 1 (Step 3), except that 4-acetyl-1-benzylpiperazin-2-one was substituted with 4-acetyl-1-(4-fluorobenzyl)-5-methylpiperazin-2-one. After the product solution was concentrated, the residue was treated with a mixture of dichloromethane and aqueous HCl. The chalky organic extract was isolated and concentrated under vacuum. The residue was subjected to HPLC purification on C-18 stationary phase eluted with water/acetonitrile/TFA mobile phase. Collection and lyophilization of appropriate fractions provided the title compound.

$^1$H NMR (400 MHz, DMSO-d$_6$) δ 12.41 (s, 1H), 11.04 (br s, 1H), 7.43 (dd, J=8.6, 5.7 Hz, 2H), 7.21 (t, J=8.6 Hz, 2H), 5.92 (s, 1H), 4.83 (d, J=14.5 Hz, 2H), 4.50 (d, J=14.5 Hz, 1H), 3.74 (dd, J=13.2, 4.0 Hz, 1H), 3.35 (d, J=14.5 Hz, 1H), 0.98 (d, J=6.0 Hz, 3H).

ES MS M+1=319

EXAMPLE 17

2-(4-Fluorobenzyl)-8,9-dihydroxy4,4dimethyl-3,4-dihydro-2H-pyrido[1,2-a]pyrazine-1,6-dione

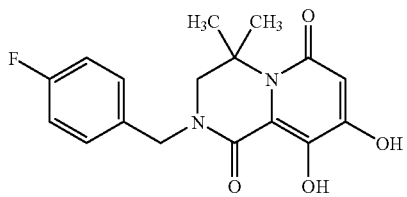

Step 1: $N^1$-(4-Fluorobenzyl)-2-methylpropane-1,2-diamine

A mixture of 4-fluorobenzaldehyde (3.1 g, 25 mmol), 1,2-diamino-2-methylpropane

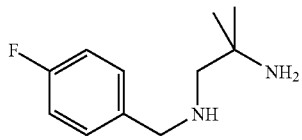

(2.2 g, 25 mmol), and a few drop of acetic acid in absolute ethanol (150 mL) was stirred at room temperature overnight. The resultant mixture was cooled to 0° C., and treated with sodium borohydride to provide predominately a major mono alkylation product. The reaction mixture was quenched with trifluoroacetic acid, and concentrated under vacuum. The residue was dissolved in methanol and subjected to HPLC purification on C-18 stationary phase eluted with water/acetonitrile/TFA mobile phase. Collection and lyophilization of appropriate fractions provided the TFA salt of the title compound. This was converted to the corresponding HCl salt by addition of HCl in diethyl ether and concentration under vacuum. The reaction is regioselective and the regiochemistry of the product was confirmed with NOE experiments on the bis HCl salt.

$^1$H NMR (400 MHz, DMSO-d$_6$) δ 9.89 (br s, 2H), 8.67 (br s, 3H), 7.72 (dd, J=8.4, 5.9 Hz, 2H), 7.29 (t, J=8.8 Hz, 2H), 4.20 (s, 2H), 3.17 (s, 2H), 1.39(s, 6H).

Step 2: 1-(4-Fluorobenzyl)-5,5-dimethylpiperazin-2-one

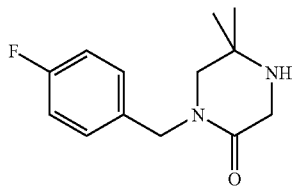

A mixture of $N^1$-(4-fluorobenzyl)-2-methylpropane-1,2-diamine bis hydrochloride salt (0.6 g, 2.23 mmol), N,N-diisopropylethylamine (2 mL, 11.5 mmol), and methyl bromoacetate (0.5 mL, 5.3 mmol) in dichloromethane (20 mL) was stirred at room temperature overnight to provide selectively a major alkylation/cyclization product (LC-MS). The resultant mixture was concentrated under vacuum, treated with a saturated solution of ammonia in chloroform, and filtered through a pad of Celite. The filtrate was concentrated and the residue was dissolved in methanol and subjected to HPLC purification on C-18 stationary phase eluted with water/acetonitrile/TFA mobile phase. Collection and lyophilization of appropriate fractions provided the TFA salt of the title compound. This was converted to the corresponding HCl salt by addition of HCl in diethyl ether and concentration under vacuum. The reaction is regioselective and the regiochemistry assigned is substantiated with subsequent successful acetylation.

$^1$H NMR (400 MHz, DMSO-d$_6$) δ 9.80 (br s, 2H), 7.34 (dd, J=8.4, 5.9 Hz, 2H), 7.19 (t, J=8.8 Hz, 2H), 4.55 (s, 2H), 3.85 (s, 2H), 3.34 (s, 2H), 1.31(s, 6H).

ES MS M+1=237

Step 3: 2-(4-Fluorobenzyl)-8,9-dihydroxy4-methyl-3,4-dihydro-2H-pyrido[1,2-a]pyrazine-1,6-dione The title compound was prepared using a procedure similar to that described in Example 1 (Step 2-3), except that 1-benzylpiperazin-2-one (Step 2) was substituted with 1-(4-fluorobenzyl)-5,5-dimethylpiperazin-2-one dihydrochloride salt. After the product solution was concentrated, the residue was treated with a mixture of dichloromethane and aqueous HCl. The chalky organic extract was isolated and concentrated under vacuum. The residue was subjected to HPLC purification on C-18 stationary phase eluted with water/acetonitrile/TFA mobile phase. Collection and lyophilization of appropriate fractions provided the title compound.

$^1$H NMR (400 MHz, DMSO-d$_6$) δ 12.91 (s, 1H), 10.95 (br s, 1H), 7.43 (dd, J=8.6, 5.7 Hz, 2H), 7.20 (t, J=8.6 Hz, 2H), 5.82 (s, 1H1), 4.64 (s, 2H), 3.23 (s, 2H), 1.45 (s, 2H).

ES MS M+1=333

EXAMPLE 18

2-(4-Fluorobenzyl)-8,9-dihydroxy-3-methyl-3,4-dihydro-2H-pyrido[1,2-a]pyrazine-1,6-dione

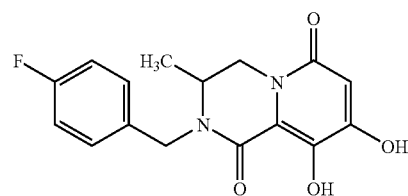

Step 1: N-[(tert-Butoxy)carbonyl]-N-(2-oxopropyl)glycine

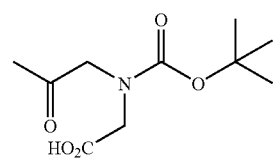

To a cold (0° C.) solution of N-[(tert-butoxy)carbonyl]-N-[(methoxy)-(methyl)carbamoylmethyl]glycine (1.0 g, 3.6 mmol; *Helvetica Chimica Acta* 2000, 83 1825), in anhydrous THF (30 mL) under an atmosphere of nitrogen, a solution of methyl magnesium bromide in ether (2.6 mL, 3M, 7.8 mmol) was added. The reaction mixture was stirred at room temperature for 1 h, cooled back to 0° C., quenched with aqueous HCl, and diluted with ether. The organic extract was washed with brine (pH adjusted to ~4-5 with addition of aqueous sodium hydroxide), dried over anhydrous magnesium sulfate, filtered, and concentrated under vacuum to provide the title compound.

$^1$H NMR (400 MHz, DMSO-$d_6$) ~1:1 mixture of rotomers δ 4.06 (s, 1H), 4.03 (s, 1H), 3.88 (s, 1H), 3.84 (s, 1H), 2.05 (s, 3H), 1.36 (s, 9/2H), 1.33 (s, 9/2H).

Step 2: 4-[(tert-Butoxy)carbonyl]-1-(4-fluorobenzyl)-6-methylpiperazin-2-one

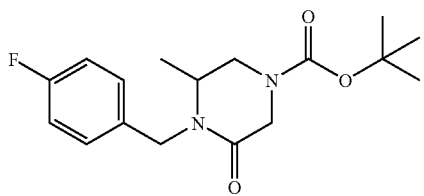

A mixture of N-[(tert-butoxy)carbonyl]-N-(2-oxopropyl)glycine (0.66 g, 2.87 mmol), 4-fluorobenzylamine (0.23 g, 1.87 mmol) in dichloroethane (14 mL) was stirred at room temperature for one hour. Sodium triacetoxyborohydride (0.79 g, 3.73 mmol) was added and the reaction mixture stirred at room temperature overnight. The resultant mixture was concentrated under vacuum. The residue was dissolved in DMF (12 mL), treated with EDC (0.55 g), and stirred at room temperature overnight. The resultant mixture was concentrated under vacuum. The residue was partitioned between ethyl acetate and dilute aqueous HCl. The organic extract was washed with brine (to pH 7), dried over anhydrous magnesium sulfate, filtered, and concentrated to provide the title compound.

ES MS M+1=323

Step 3: 4-Acetyl-1-(4-fluorobenzyl)-6-methylpiperazin-2-one

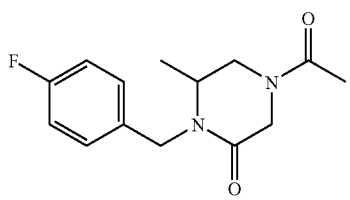

A steady stream of anhydrous HCl gas was bubbled through a cold (0° C.) solution of 4-[(tert-butoxy)carbonyl]-1-(4-fluorobenzyl)-6-methylpiperazin-2-one (0.62 g, 1.9 mmol) in ethyl acetate (20 mL) for 5 minutes. The resultant mixture was capped and stirred at the same temperature for 1 h. The product mixture was concentrated under vacuum. The residue was treated with a mixture of N,N-diisopropylethylamine (1.00 mL, 5.8 mmol), DMAP (5 mg), and acetic anhydride (0.22 mL, 2.3 mmol) in methylene chloride (10 mL). The resultant mixture was concentrated and the residue was subjected to column chromatography on silica gel eluting with a mixture of 10% methanol in ethyl acetate. Collection and concentration of appropriate fractions provided the title piperazinone.

$^1$H NMR (400 MHz, CDCl$_3$) ~2:1 mixture of rotomers δ 7.72 (dd, J=8.4, 5.9 Hz, 2H), 7.29 (t, J=8.8 Hz, 2H), . . . 2.14 (s, 2H), 2.11 (s, 1H), .1.24 (d, J=6.8 Hz, 1H), 1.19 (d, J=6.8 Hz, 2H).

ES MS M+1=265

Step 3: 2-(4-Fluorobenzyl)-8,9-dihydroxy-4-methyl-3,4-dihydro-2H-pyrido[1,2-a]pyrazine-1,6-dione The title compound was prepared using a procedure similar to that described in Example 2 (Step 5), except that 4-acetyl-1-(4-fluorobenzyl)piperazin-2-one was substituted with 4-acetyl-1-(4-fluorobenzyl)-6-methylpiperazin-2-one. After the product solution was concentrated, the residue was treated with a mixture of dichloromethane and aqueous HCl. The chalky organic extract was isolated and concentrated under vacuum. The residue was subjected to HPLC purification on C-18 stationary phase eluted with water/acetonitrile/TFA mobile phase. Collection and lyophilization of appropriate fractions provided the title compound.

$^1$H NMR (400 MHz, DMSO-$d_6$) δ 12.23 (s, 1H), 10.10 (br s, 1H), 7.43 (dd, J=8.6, 5.7 Hz, 2H), 7.20 (t, J=8.6 Hz, 2H), 5.94 (s, 1H), 4.98 (d, J=15.0 Hz, 1H), 4.40 (d, J=15.0 Hz, 2H), 3.85 (m, 1H), 3.49 (dd, J=14, 3.8 Hz, 1H), 1.08 (d, J=6.6 Hz, 3H).

ES MS M+1=319

EXAMPLE 19

2-(4-Fluorobenzyl)-8,9-dihydroxy-1,6-dioxo-1,3,4,6-tetrahydro-2H-pyrido[1,2-a]-pyrazine-7-carbonitrile

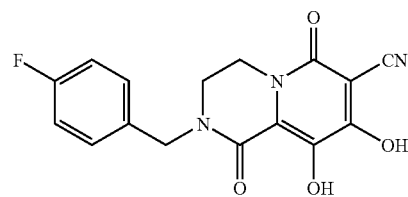

Step 1: 3-[4-(4-Fluorobenzyl)-3-oxopiperazin-1-yl]-3-oxopropanenitrile

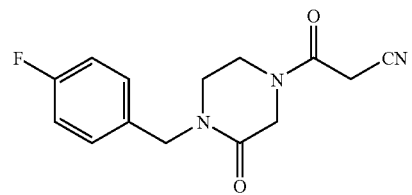

To a solution of 1-(4-fluorobenzyl)piperazin-2-one (1.99 g, 9.6 mmol), cyanoacetic acid (0.82 g, 9.6 mmol), EDC (2.02 g, 10.5 mmol), and HOBt (0.15 g, 0.96 mmol) in anhydrous DMF (40 mL), N,N-diisopropylethylamine was added until the solution is about pH 6. The reaction mixture was stirred at room temperature overnight and concentrated under vacuum. The residue was partitioned between chloroform and water. The organic extract was washed with brine, dried over anhydrous magnesium sulfate, filtered, and concentrated under vacuum to provide the title compound. The residue was subjected to column chromatography on silica gel eluting with a mixture of 9:1:0.1 mixture of chloroform, methanol, and aq ammonium hydroxide. Collection and concentration of appropriate fractions provided the title product. Residual protic solvent was removed by co-evaporation with benzene (3×). ES MS M-OCH$_3$=276

Step 2: 2-(4-Fluorobenzyl)-8,9-dihydroxy-1,6-dioxo-1,3,4,6-tetrahydro-2H-pyrido[1,2-a]-pyrazine-7-carbonitrile The title compound was prepared using a procedure similar to that described in Example 2 (Step 5), except that 4-acetyl-1-(4-fluorobenzyl)piperazin-2-one was substituted with 3-[4-(4-fluorobenzyl)-3-oxopiperazin-1-yl]-3-oxopropanenitrile. After the product solution was concentrated, the residue was treated with a mixture of dichloromethane and aqueous HCl. The chalky organic extract was isolated and concentrated under vacuum. The residue was subjected to HPLC purification on C-18 stationary phase eluted with water/acetonitrile/TFA mobile phase. Collection and lyophilization of appropriate fractions provided the title compound.

$^1$H NMR (400 MHz, DMSO-d$_6$) δ 12.23 (s, 1H), 10.10 (br s, 1H), 7.43 (dd, J=8.6, 5.7 Hz, 2H), 7.20 (t, J=8.6 Hz, 2H), 4.68 (s, 2H),. 3.97 (t, J=5.3 Hz, 2H), 3.56 (t, J=5.3 Hz, 2H).
ES MS M+1=330

EXAMPLE 20

2-(4-Fluorobenzyl)-8,9-dihydroxy-7-[(4-methyl-3-oxopiperazin-1-yl)methyl]-3,4-dihydro-2H-pyrido[1,2-a]pyrazine-1,6-dione

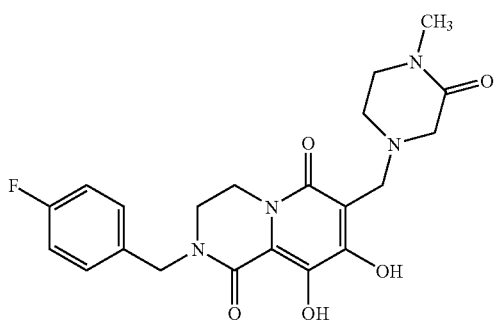

The title compound was prepared using a procedure similar to that described in Example 11, except that piperidine was substituted with 4-methyl-3-oxopiperazine.

$^1$H NMR (400 MHz, DMSO-d$_6$) δ 12.63 (s, 1H), 11.90 (br s, 1H), 7.41 (dd, J=6.0, 8.4 Hz, 2H), 7.21 (t, J=8.8 Hz, 2H), 4.72 (s, 2H), 4.19 (br s, 2H), 4.07 (t, J=5.1 Hz, 2H), 3.78 (br s, 2H), 3.63 (t, J=5.1 Hz, 2H), 2.84 (s, 3H).
ES MS M+1=545

EXAMPLE 21

2-(4-Fluorobenzyl)-8,9-dihydroxy-7-[(3-oxopiperazin-1-yl)methyl]-3,4-dihydro-2H-pyrido[1,2-a]pyrazine-1,6-dione

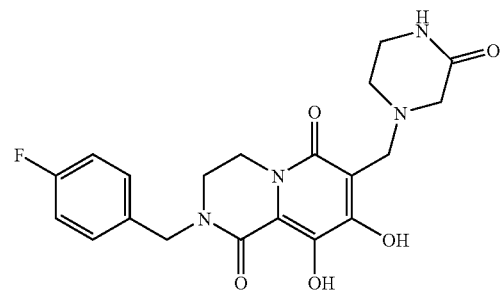

The title compound was prepared using a procedure similar to that described in Example 11, except that piperidine was substituted with 2-oxopiperazine.

$^1$H NMR (400 MHz, DMSO-d$_6$) δ 12.60 (s, 1H), 11.92 (br s, 1H), 8.32 (s, 1H), 7.41 (dd, J=6.0, 8.4 Hz, 2H), 7.21 (t, J=8.8 Hz, 2H), 4.71 (s, 2H), 4.21 (br s, 2H), 4.07 (t, J=5.1 Hz, 2H), 3.74(br s, 2H), 3.62 (t, J=5.1 Hz, 2H), 3.37 (br s, 2H).
ES MS M+1=530

EXAMPLE 22

4-[(Benzyloxy)methyl]-2-(4-fluorobenzyl)-8,9-dihydroxy-3,4-dihydro-2H-pyrido[1,2-a]pyrazine-1,6-dione

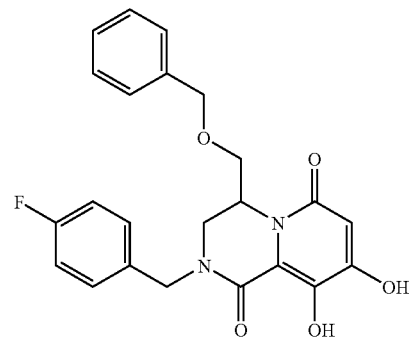

Step 1: 2-[(Benzyloxy)methyl]-1-tritylaziridine

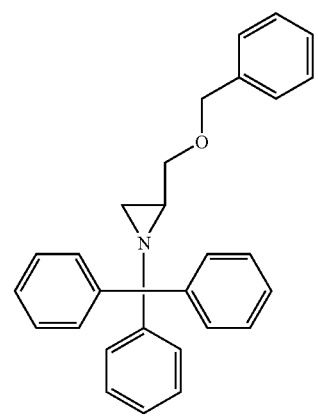

To a cold (0° C.) solution of lithium aluminum hydride in diethyl ether (1 M, 15 mL, 15 mmol) under an atmosphere of nitrogen, a solution of methyl 1-trityl-2-aziridinecarboxylate (5.04 g, 14.7 mmol) in anhydrous ether (60 mL) was added over a period of 0.5 h. The resultant mixture was allowed to slowly warm up and stirred at room temperature for 1 hour. The resultant mixture was cooled back to 0° C. and treated successively with water (0.57 mL) over a period of 10 minutes, followed by addition of 15% aq NaOH (0.57 mL), and water (1.7 mL). The resultant suspension was filtered through a pad of Celite. The filtrate was washed with brine, dried over anhydrous sodium sulfate, filtered, and concentrated under vacuum. The residue was treated with a mixture of ether (40 mL) and hexane (200 mL) with cooling. The precipitate was collected by filtration to provide (1-tritylaziridin-2-yl)methanol as white solid. Without further purification, the alcohol (1.0 g, 3.17 mmol) was added portionwise to a suspension of sodium hydride (60% dispersion in mineral oil, 0.24 g, 6.0 mmol). To the resultant mixture, terta-n-butylammonium iodide (50 mg, 0.14 mmol) and benzyl bromide (0.65 g, 3.8 mmol) were added. The reaction mixture was stirred at room temperature overnight and treated with water (20 mL). The organic extract was diluted with ether, washed with brine, dried over anhydrous sodium sulfate, filtered, and concentrated under vacuum. The residue was subjected to column chromatography on silica gel eluting with a mixture of 5% ethyl acetate in hexane. Collection and concentration of appropriate fractions provided the title compound.

$^1$H NMR (400 MHz, CDCl$_3$) δ 7.52-7.18 (m, 20 H), 4.52 (s, 2H), 3.86 (dd, J=10.1, 5.1 Hz, 1H), 3.52 (dd, J=10.1, 5.9 Hz, 1H), 1.72 (d, J=3 Hz, 1H), 1.54 (m, overlap with H$_2$O signal), 1.18 (d, J=5.9 Hz, 1H).

ES MS M+1=406

Step 2: Methyl {2-[(benzyloxy)methyl]aziridin-1-yl}acetate

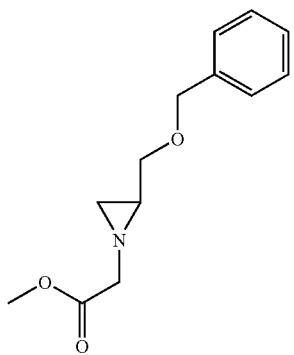

To a cold (0° C.) solution of 2-[(benzyloxy)methyl]-1-tritylaziridine (1.28 g, 3.16 mmol) in dichloromethane (13 mL), trifluoroacetic acid (1 mL) and triethylsilane (2.0 mL) was added and stirred at the temperature for 1 h. The resultant mixture was concentrated under vacuum, and the residue was partitioned between ether and brine. The organic extract was dried with anhydrous magnesium sulfate, filtered, and concentrated under vacuum. The residue was subjected to column chromatography on silica gel eluting with a mixture of 50-100% THF in hexane. Collection and concentration of appropriate fractions provided 2-[(benzyloxy)methyl]aziridine.

To a cold (−78° C.) solution of 2-[(benzyloxy)methyl] aziridine (0.42 g, 2.57 mmol) and N,N-diisopropylethylamine (0.5 mL, 2.90 mmol) in dichloromethane (15 mL) under an atmosphere of nitrogen, ethyl bromoacetate (0.39, 2.5 mmol) was added over a period of 1 h. The resultant mixture was allowed to slowly warm up to room temperature and stirred overnight. The resultant mixture was washed with brine, dried over anhydrous magnesium sulfate, filtered, and concentrated under vacuum. The residue was subjected to column chromatography on silica gel eluting with a mixture of 70% ethyl acetate in hexane. Collection and concentration of appropriate fractions provided the title compound.

$^1$H NMR (400 MHz, CDCl$_3$) δ 7.35-7.26 (m, 5 H), 4.59 (d, J=11.9 Hz, 1H), 4.53 (d, J=11.9 Hz, 1H), 3.74 (s, 3H), 3.52 (m, 2H), 3.25 (d, J=16.1 Hz, 1H), 2.98 (d, J=16.1 Hz, 1H), 1.83(d, J=3.6 Hz, 1H), 1.79 (m, 1H), 1.43 (d, J=6.4 Hz, 1H).

ES MS M+1=236

Step 3: 4-Acetyl-5-[(benzyloxy)methyl]-1-(4-fluorobenzyl)piperazin-2-one

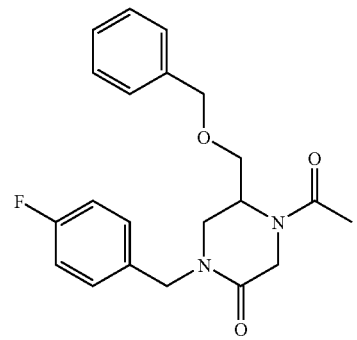

A mixture of methyl {2-[(benzyloxy)methyl]aziridin-1-yl}acetate (0.4 g, 1.7 mmol), 4-fluorobenzylamine (0.38 g, 3.3 mmol), and boron trifluoride etherate (50 μL) was heated in a sealed glass tube at 95° C. for 68 h (Bull. Chem. Soc. Jpn., 1986, 59, 321). The resulting mixture was dissolved in dichloromethane (50 mL), cooled to 0° C., and treated with a mixture of triethylamine (0.95 mL, 6.8 mmol), DMAP (21 mg, 0.17 mmol), and acetic anhydride (0.48 mL, 5.1 mmol). The mixture was stirred at room temperature overnight, and extracted successively with saturated aqueous solution of sodium bicarbonate, dilute aqueous HCl, and brine. The organic extract was dried over anhydrous magnesium sulfate, filtered, and concentrated under vacuum. The residue was subjected to column chromatography on silica gel eluting with a mixture of 2% methanol in ethyl acetate. Collection and concentration of appropriate fractions provided the title piperazinone.

ES MS M+1=371

Step 4: 4-[(Benzyloxy)methyl]-2-(4-fluorobenzyl)-8,9-dihydroxy-3,4-dihydro-2H-pyrido[1,2-a]pyrazine-1,6-dione The title compound was prepared using a procedure similar to that described in Example 1 (Step 3), except that 4-acetyl-1-benzylpiperazin-2-one was substituted with 4-acetyl-5-[(benzyloxy)methyl]-1-(4-fluorobenzyl)piperazin-2-one.

$^1$H NMR (400 MHz, CDCl$_3$) δ 12.50 (s, 1H), 8.20 (br s, 1H), 7.33-6.99 (m, 9H), 6.14 (s, 1H), 5.09 (m, 1H), 4.75 (d, J=14.6 Hz, 2H), 4.47 (d, J=14.6 Hz, 1H), 4.37 (d, J=11.7, Hz,

1H), 4.25 (d, J=11.7 Hz, 1H), 3.73 (d, J=13.2 Hz, 1H), 3.66 (m, 1H), 3.49 (m, 2H), 3.35 (d, J=9.3 Hz, 1H).

ES MS M+1=425

EXAMPLE 23

4-(Hydroxymethyl)-2-(4-fluorobenzyl)-8,9-dihydroxy-3,4-dihydro-2H-pyrido[1,2-a]pyrazine-1,6-dione

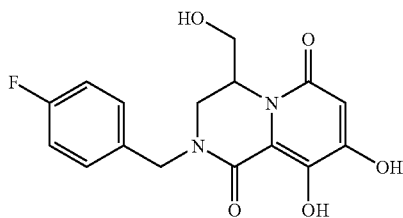

A mixture of 4-[(benzyloxy)methyl]-2-(4-fluorobenzyl)-8,9-dihydroxy-3,4-dihydro-2H-pyrido[1,2-a]pyrazine-1,6-dione (151 mg) and 5% Pd/C (57 mg) in ethanol (20 mL) was stirred under an atmosphere of hydrogen (1 atm) at room temperature overnight. The product mixture was filtered through a pad of Celite, and concentrated under vacuum. The residue was subjected to HPLC purification on C-18 stationary phase eluted with water/acetonitrile/TFA mobile phase. Collection and lyophilization of appropriate fractions provided the title compound.

$^1$H NMR (400 MHz, DMSO-d$_6$) δ 12.39 (s, 1H), 11.10 (s, 1H), 7.41 (dd, J=5.6, 8.6 Hz, 2H), 7.21 (t, J=9.0 Hz, 2H), 5.93 (s, 1H), 5.11 (t, J=5.7 Hz, 1H), 4.72-4.60 (m, 2H), 3.69 (br s, 2H).

ES MS M+1=335

EXAMPLE 24

4-[(1,1-Dioxido-1,2-thiazinan-2-yl)methyl]-2-(4-fluorobenzyl)-8,9-dihydroxy-3,4-dihydro-2H-pyrido[1,2-a]pyrazine-1,6-dione

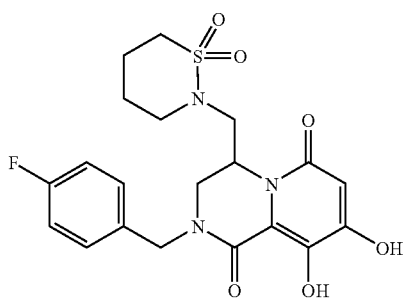

Step 1: 4-Acetyl-5-[(1,1-Dioxido-1,2-thiazinan-2-yl)methyl]-1-(4-fluorobenzyl)-piperazin-2-one

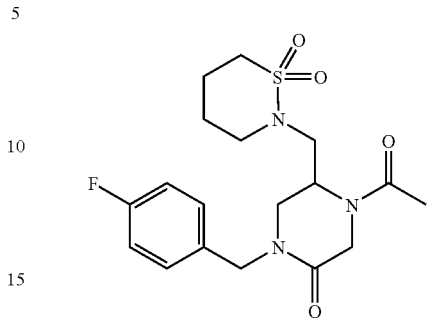

A mixture of 4-acetyl-5-[(benzyloxy)methyl]-1-(4-fluorobenzyl)piperazin-2-one (6.5 g) and 20% Pd/C (1.4 g) in ethanol (175 mL) was shaken under an atmosphere of hydrogen (60 psi) at room temperature overnight. The product mixture was filtered through a pad of Celite, and concentrated under vacuum. Residual ethanol was removed by co-evaporation with toluene under vacuum (3×). The resultant alcohol was used without further purification. A mixture of the alcohol (1.0 g, 3.57 mmol), 1,2-thiazinane 1,1-dioxide (0.73, 5.4 mmol), and cyanomethylenetri-n-butylphosphorane (1.3 g, 5.4 mmol; [157141-27-0]) in benzene (20 mL) was purged with nitrogen and heated in a sealed tube at 100° C. overnight. The reaction mixture was concentrated under vacuum, and the residue was subjected to column chromatography on silica gel eluting with a mixture of 5% methanol in ethyl acetate. Collection and concentration of appropriate fractions provided the title compound.

High Resolution FT-ICR M+H=398.1556; C$_{18}$H$_{24}$FN$_3$O$_4$S+H calculated 398.1545.

Step 2: 4-[(1,1-dioxido-1,2-thiazinan-2-yl)methyl]-2-(4-fluorobenzyl)-8,9-dihydroxy-3,4-dihydro-2H-pyrido[1,2-a]pyrazine-1,6-dione To a cold (0° C.) solution of 4-acetyl-5-[(1,1-dioxido-1,2-thiazinan-2-yl)methyl]-1-(4-fluorobenzyl)-piperazin-2-one (75 mg, 0.19 mmol) and diethyl oxalate (29 μL, 0.21 mmol) in DMF (3 mL) under an atmosphere of nitrogen, a solution of sodium bis(trimethylsilyl)amide in THF (1M, 0.21 mL, 0.21 mmol) was added over a period of 0.5 h and stirred at the temperature for 30 min. Then additional sodium bis(trimethylsilyl)amide in THF (1M, 0.21 mL, 0.21 mmol) was added over a period of 0.5 h and stirred at the temperature for 1 h. The product mixture was concentrated under vacuum, and the residue partitioned between aqueous HCl and ethyl acetate. The organic extract was dried over anhydrous magnesium sulfate, filtered, and concentrated under vacuum. The residue was subjected to HPLC purification on C-18 stationary phase eluted with water/acetonitrile/TFA mobile phase. Collection and lyophilization of appropriate fractions provided the title compound.

$^1$H NMR (400 MHz, CDCl$_3$) δ 12.39 (s, 1H), 11.16 (s, 1H), 7.40 (dd, J=8.3, 5.8 Hz, 2H), 7.20 (t, J=8.3 Hz, 2H), 5.93 (s, 1H), 5.07 (d, J=14.6 Hz, 1H), 4.82 (m, 1H), 4.25 (d, J=14.6 Hz, 1H), 3.68 (dd, J=13.4, 4.4 Hz, 1H), 3.56 (d, J=13.5, Hz, 1H), 3.4-2.9 (m), 1.98 (m, 2H), 1.49 (m, 2H).

EXAMPLE 25

2-(4-Fluorobenzyl)-8,9-dihydroxy-7-(piperidin-1-ylmethyl)-2H-pyrido[1,2-a]pyrazine-1,6-dione

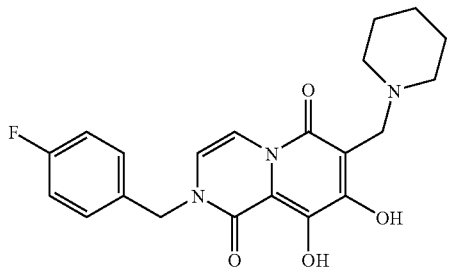

The title compound was prepared using a procedure similar to that described in Example 11, except that 2-(4-fluorobenzyl)-8,9-dihydroxy-3,4-dihydro-2H-pyrido[1,2-a]pyrazine-1,6-dione was substituted with 2-(4-fluorobenzyl)-8,9-dihydroxy-2H-pyrido[1,2-a]pyrazine-1,6-dione (Example 14).

$^1$H NMR (500 MHz, DMSO-$d_6$) δ 12.00 (br s, 1H), 9.08 (br s, 1H), 7.50 (d, J=6.3 Hz, 1H), 7.45 (dd, J=8.4, 5.7 Hz, 2H), 7.22 (t, J=8.7 Hz, 2H), 6.89 (d, J=6.3 Hz, 1H), 4.97 (s, 2H), 4.15 (s, 2H), 3.6-2.9 (br m), 1.8-1.4 (br m).

HRMS FT-ICR m/z obsd 400.1655, $C_{21}H_{22}FN_3O_4$+H required 400.1667

EXAMPLE 26

2-(4-Fluorobenzyl)-8,9-dihydroxy-7-[(3-oxopiperazin-1-yl)methyl]-2H-pyrido[1,2-a]pyrazine-1,6-dione

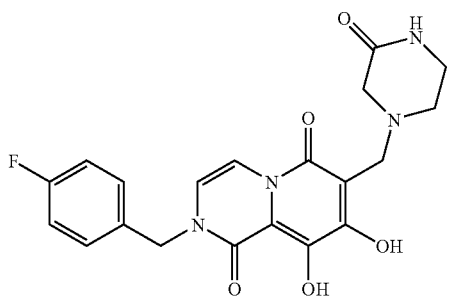

The title compound was prepared using a procedure similar to that described in Example 25, except that piperidine was substituted with 3-oxopiperazine.

$^1$H NMR (500 MHz, DMSO-$d_6$) δ 12.00 (br s, 1H), 8.28 (s, 1H), 7.49 (d, J=6.6 Hz, 1H), 7.45 (dd, J=8.8, 5.4 Hz, 2H), 7.22 (t, J=8.9 Hz, 2H), 6.89 (d, J=6.6 Hz, 1H), 4.97 (s, 2H), 4.24 (s, 2H), 3.72 (s, 2H), 3.35 (br s, 4H).

HRMS FT-ICR m/z obsd 415.1406, $C_{20}H_{19}FN_4O_5$+H required 415.1412.

EXAMPLE 27

2-(4-Fluorobenzyl)-8,9-dihydroxy-7-[(4-methyl-3-oxopiperazin-1-yl)methyl]-2H-pyrido[1,2-a]pyrazine-1,6-dione

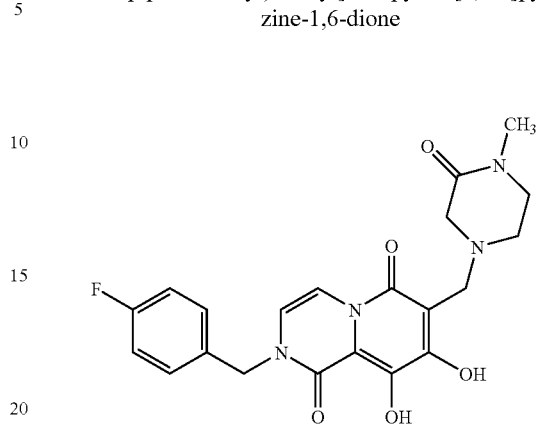

The title compound was prepared using a procedure similar to that described in Example 25, except that piperidine was substituted with 4-methyl-3-oxopiperazine.

$^1$H NMR (400 MHz, DMSO-$d_6$) δ 12.00 (br s, 1H), 7.49 (d, J=6.5 Hz, 1H), 7.45 (dd, J=8.7, 5.6 Hz, 2H), 7.20 (t, J=8.9 Hz, 2H), 6.88 (d, J=6.6 Hz, 1H), 4.97 (s, 2H), 4.22 (s, 2H), 3.76 (s, 2H), 3.43(m, 4H), 2.83 (s, 3H).

HRMS FT-ICR m/z obsd 429.1562, $C_{21}H_{21}FN_4O_5$+H required 429.1569.

EXAMPLE 28

2-(4-Fluorobenzyl)-8,9-dihydroxy-7-[(morpholin4yl)methyl]-2H-pyrido[1,2-a]pyrazine-1,6-dione

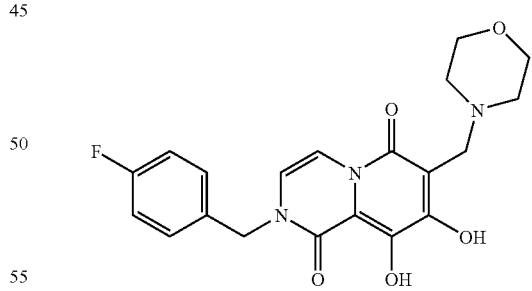

The title compound was prepared using a procedure similar to that described in Example 25, except that piperidine was substituted with morpholine.

$^1$H NMR (400 MHz, DMSO-$d_6$) δ 12.00 (br s, 1H), 7.47 (d, J=6.5 Hz, 1H), 7.45 (dd, J=8.4, 5.6 Hz, 2H), 7.22 (t, J=8.8 Hz, 2H), 6.83 (d, J=6.5 Hz, 1H), 4.96 (s, 2H), 4.19 (s, 2H), 3.79 (br s, 4H), 3.18(br s, 4H).

HRMS FI-ICR m/z obsd 402.1452, $C_{20}H_{20}FN_3O_5$+H required 402.1460.

EXAMPLE 29

2-(4-Fluorobenzyl)-8,9-dihydroxy-7-[(thiomorpholin-4-yl)methyl]-2H-pyrido[1,2-a]pyrazine-1,6-dione

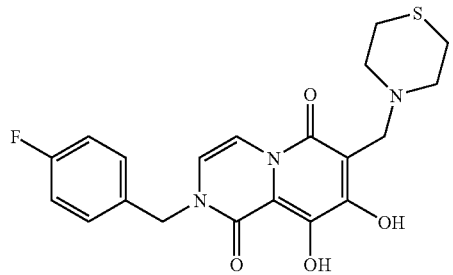

The title compound was prepared using a procedure similar to that described in Example 25, except that piperidine was substituted with thiomorpholine.

$^1$H NMR (400 MHz, DMSO-d$_6$) δ 7.44 (m, 3H), 7.22 (t, J=8.8 Hz, 2H), 6.79 (d, J=6.4 Hz, 1H), 4.94 (s, 2H), 4.16 (s, 2H), 3.35 (br s, 4H), 2.90(br s, 4H).

HRMS FT-ICR m/z obsd 418.1215, C$_{20}$H$_{20}$FN$_3$O$_4$S+H required 418.1232.

EXAMPLE 30

2-[4-Fluoro-2-(methylthio)benzyl]-8,9-dihydroxy-2H-pyrido[1,2-a]pyrazine-1,6-dione

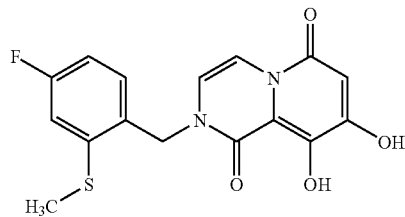

The title compound was prepared using procedures similar to that described in Examples 2 and 14, except that 4-fluorobenzaldehyde was substituted with 4-fluoro-2-(methylthio)benzaldehyde in Step 1, Example 2.

$^1$H NMR (400 MHz, DMSO-d$_6$) δ 12.7-12.3 (br signal, 2H), 7.39 (d, J=6.5 Hz, 1H), 7.25 (dd, J=8.4, 6.4 Hz, 1H), 7.18 (dd, J=10.4, 2.4 Hz, 1H), 6.98 (br t, 1H), 6.53 (d, J=6.5 Hz, 1H), 6.10 (s, 1H), 4.89 (s, 2), 2.54 (s, 3H).

HRMS FT-ICR m/z obsd 349.0656, C$_{16}$H$_{13}$FN$_2$O$_4$S+H required 349.0653

EXAMPLE 31

7-[(1-Acetylpiperidin-4-yl)methyl]-2-(4-fluorobenzyl)-8,9-dihydroxy-3,4-dihydro-2H-pyrido[1,2-a]pyrazine-1,6-dione

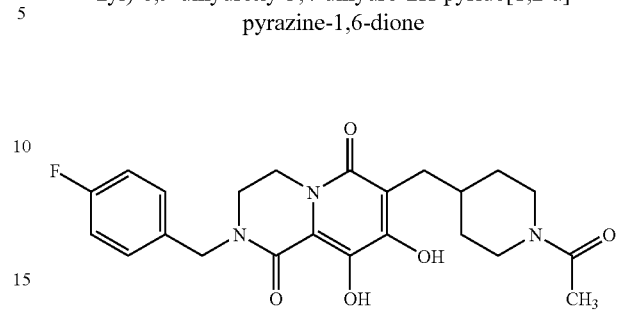

Step 1: tert-Butyl 4-{3-[4-(4-fluorobenzyl)-3-oxopiperazin-1-yl]-3-oxopropyl}piperidine-1-carboxylate

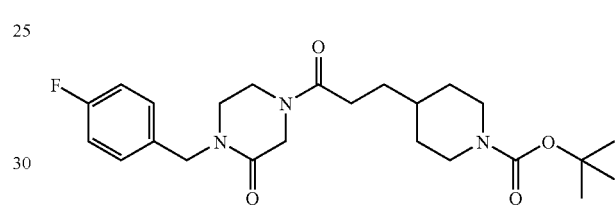

To a solution of 1-boc-piperidin-4-ylpropionic acid (1.20 g, 4.7 mmol, Astatech) in DMF (10 mL), 1-(3-dimethylaminopropyl)-3-ethylcarbodiimide hydrochloride (1.16 g, 6.1 mmol) and 1-hydroxy-7-azabenzotriazole (0.83 g, 6.1 mmol) were added and the solution was stirred at room temperature for 30 min. To the resultant solution, a solution of 1-(4-fluorobenzyl)piperazin-2-one (1.07 g, 5.1 mmol, see Example 31, Steps 5-8) in DMF (2 mL) was added and the mixture was stirred for two hours. The product mixture was concentrated under vacuum, and the residue partitioned between water and ethyl acetate. The combined organic extracts were washed with brine, dried over anhydrous sodium sulfate, filtered, and concentrated under reduced pressure. The residue was purified by flash column chromatography (ISCO column, 120 g silica gel) eluting with a 0-6% MeOH/CHCl$_3$ gradient over 40 min. Collection and concentration of appropriate fractions provided the coupled product as a white solid.

$^1$H NMR (400 MHz, d$_6$ DMSO) δ 7.31 (m, 21), 7.18 (m, 2H), 4.53 (s, 2H), 4.19 (s, 1H), 4.07 (s, 1H), 3.91 (m, 2H), 3.67 (m, 2H), 3.31 (m, 2H), 3.21 (m, 1H), 2.64 (m, 2H), 2.34 (m, 2H), 1.62 (m, 2H), 1.41 (m, 2H), 1.39 (s, 9H), and 0.95 (m, 2H).

ES MS M+1=448

Step 2: tert-Butyl 4-{[2-(4-fluorobenzyl)-8,9-dihydroxy-1,6-dioxo-1,3,4,6-tetrahydro-2H-pyrido[1,2-a]pyrazin-7-yl]methyl}piperidine-1-carboxylate

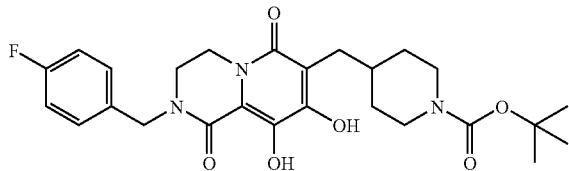

The title compound was prepared using a procedure similar to that described in Example 2 (Step 5) using tert-butyl 4-{3-[4-(4-fluorobenzyl)-3-oxo-piperazin-1-yl]-3-oxopropyl}piperidine-1-carboxylate (1.0 g, 2.23 mmol). The crude product was taken on as is to the next step.

ES MS M+1=402

Step 3: 2-(4-Fluorobenzyl)-8,9-dihydroxy-7-(piperidin-4-ylmethyl)-3,4-dihydro-2H-pyrido[1,2-a]pyrazine-1,6-dione mono TFA salt

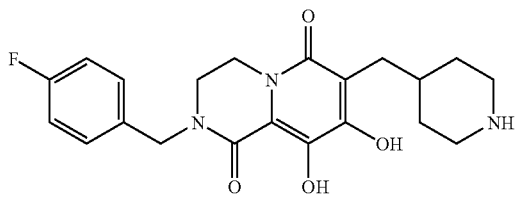

To a cold (0° C.) solution of tert-butyl 4-{[2-(4-fluorobenzyl)-8,9-dihydroxy-1,6-dioxo-1,3,4,6-tetrahydro-2H-pyrido[1,2-a]pyrazin-7-yl]methyl}piperidine-1-carboxylate (1.12 g, 2.23 mmol) in methylene chloride (10 mL), trifluoroacetic acid (3.4 mL, 45 mmol) was added and the mixture was stirred for 2 hours. The mixture was concentrated in vacuo and the residue was purified by prep HPLC (Waters prep LC 4000 System using a Waters Nova Pak column [3*10×40 mm I.D. cartridges, C18, 6 μM pore size) eluting with 95-5% water (0.10% TFA)/acetonitrile (0.10% TFA) gradient at 60 mL/min]. Combined and concentrated the product fractions to give a yellow solid. The solids were triturated with acetonitrile and collected by vacuum filtration.

$^1$H NMR (400 MHz, $d_6$ DMSO) δ 12.61 (s, 1H), 10.42 (s, 1H), 8.41 (m, 1H), 8.10 (m, 1H), 7.40 (m, 2H), 7.20 (m, 2H), 4.68 (s, 2H), 4.02 (m, 2H), 3.57 (m, 2H), 3.22 (m, 2H), 2.80 (m, 2H), 2.43 (m, 2H), 1.84 (m, 1H), 1.67 (m, 2H), and 1.37 (m, 2H), High Resolution FF-ICR $C_{21}H_{24}FN_3O_4$+H=402.1833; calculated 402.1824.

Step 4: 7-[(1-Acetylpiperidin-4-yl)methyl]-2-(4-fluorobenzyl)-8,9-dihydroxy-3,4-dihydro-2H-pyrido[1,2-a]pyrazine-1,6-dione To a suspension of 2-(4-fluorobenzyl)-8,9-dihydroxy-7-(piperidin-4-ylmethyl)-3,4-dihydro-2H-pyrido[1,2-a]pyrazine-1,6-dione mono TFA salt (50 mg, 0.125 mmol) in anhydrous methylene chloride (2 mL), pyridine (12 μL, 0.149 mmol) and acetic anhydride (14 μL, 0.149 mmol) were added. The reaction mixture was stirred at room temperature overnight. The reaction mixture was concentrated under vacuum, and the residue was purified by prep HPLC (Gilson semi preparative HPLC system using a Waters Nova Pak column [10×40 mm I.D. cartridge, C18, 6 μM pore size) eluting with 95-5% water (0.10% TPA)/acetonitrile (0.10% TFA) gradient at 35 mL/min]. Collection and lyophilization of appropriate fractions provided he title compound as white solid.

$^1$H NMR (400 MHz, $d_6$ DMSO) δ 12.60 (s, 1H), 10.25 (br s, 1H), 7.40 (m, 2H), 7.20 (m, 2H), 4.68 (s, 2H), 4.28 (d, 1H, J=12.9 Hz), 4.03 (m, 2H), 3.74 (d, 1H, J=13.2 Hz), 3.58 (m, 2H), 2.91 (m, 1H), 2.42 (m, 3H), 1.96 (s, 3H), 1.79 (m, 1H), 1.53 (m, 2H), and 0.96-1.17 (m, 2H).

High Resolution FT-ICR $C_{23}H_{26}FN_3O_5$+H=444.1929; calculated 444.1929.

Step 5: N-(2,2-Dimethoxyethyl)-N-(4-fluorobenzyl)amine

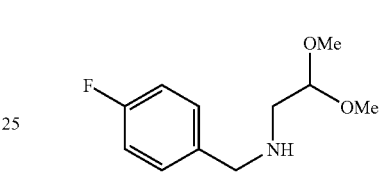

A mixture of 4-fluorobenzaldehyde (227.6 g, 1.83 mol) and dimethoxy-ethylamine (192.6 g, 1.83 mol) in methanol (2.5 L) was heated at 65° C. for 1.5 h. The solution was allowed to cool to room temperature overnight and treated with sodium borohydride (47.6 g 1.26 mol) in portions over a period of 2 h. The resultant mixture was stirred at room temperature for 3 h and quenched with water (1 L). The product mixture was concentrated to about 1 L and extracted with diethyl ether (3×). The ethereal extracts were combined, washed with brine, dried over anhydrous sodium sulfate, filtered, and concentrated under vacuum to provide the title compound as yellow oil.

$^1$H NMR (400 MHz, CDCl$_3$) δ 7.28 (dd, J=5.5, 8.6 Hz, 2H), 7.00 (t, J=6.8 Hz, 2H), 4.48 (t, J=5.5 Hz, 1H), 3.77 (s, 2H), 3.37 (s, 6H), 2.73 (d, J=5.5 Hz, 2H).

ES MS M+1=214

Step 6: N$^2$-Benzyloxycarbonyl-N$^1$-(2,2dimethoxyethyl)-N$^1$-(4-fluorobenzyl)-glycinamide

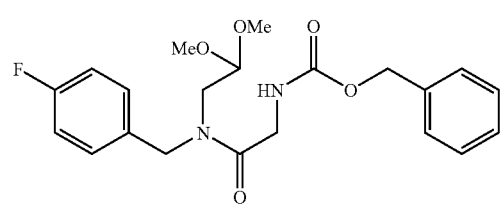

To a solution of N-(2,2-dimethoxyethyl)-N-(4-fluorobenzyl)amine (50.6 g, 237.3 mmol), N—CBZ-glycine (54.6 g, 260.8 mmol), EDC (50.0 g, 260.8 mmol), and HOBt (4.2 g, 27 mmol) in anhydrous DMF (500 mL), N,N-diisopropylethylamine (~10 mL) was added until the solution is about pH 7. The reaction mixture was stirred at room temperature overnight and concentrated under vacuum. The residue was partitioned between dichloromethane (1 L) and water (250 mL).

The organic extract was washed with brine, dried over anhydrous sodium sulfate, filtered, and concentrated under vacuum to provide the title compound.

ES MS M-OCH$_3$=374

Step 7: 4-Benzyloxycarbonyl-1-(4-fluorobenzyl)-3,4-dihydropyrazin-2(1H)-one

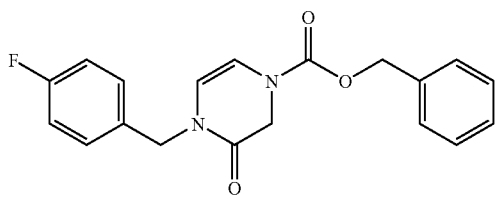

To a solution of N$^2$-benzyloxycarbonyl-N$^1$-(2,2-dimethoxyethyl)-N$^1$-(4-fluorobenzyl)glycinamide (61.5 g, 152 mmol) and p-toluenesulfonic acid monohydrate (3 g) in toluene (450 mL) was stirred at 75° C. for 5 days. Each day an additional 3 g of toluenesulfonic acids was added. The resultant reaction mixture was cooled to room temperature and filtered through a pad of Celite. The filtrate was concentrated under vacuum, and the residue dissolved in dichloromethane. The organic solution was washed successively with saturated aqueous sodium bicarbonate, brine, dried over anhydrous sodium sulfate, filtered, and concentrated under vacuum. To the residual solid was subjected to column chromatography on silica gel eluting with dichloromethane and then 5% ethyl acetate in dichloromethane. Appropriate fractions were collected and concentrated under vacuum. Residual ethyl acetate and dichloromethane was removed by co-evaporation with toluene for 3 time for subsequent hydrogenation. The residue was triturated with hexane, and filtered to provide the cyclization product as an off-white solid.

$^1$H NMR (400 MHz, CDCl$_3$) δ 7.37 (br s, 5H), 7.23 (m, 2H), 7.02 (t, J=8.6 Hz, 2H), 6.44 (d, J=6.0 Hz, ½H), 6.32 (d, J=6.0 Hz, ½H), 5.53 (d, J=6.0 Hz, ½H), 5.42 (d, J=6.0 Hz, ½H), 5.21 (s, 2H), 4.65 (s, 2H), 4.38 (s, 2H).

ES MS M+1=341

Step 8: 1-(4-Fluorobenzyl)piperazin-2-one

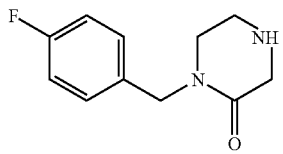

A mixture of 4-benzyloxycarbonyl-1-(4-fluorobenzyl)-3,4-dihydro-pyrazin-2(1H)-one (0.5 g, 14.5 mmol) and Pearlman's catalyst (26 mg; 20% palladium hydroxide on carbon) in methanol (25 mL) was stirred under an atmosphere of hydrogen (1 atm) at room temperature overnight. The product mixture was filtered through a pad of Celite, and concentrated under vacuum to provide 1-(4-fluorobenzyl)piperazin-2-one.

$^1$H NMR (400 MHz, d$_6$DMSO) δ 7.29 (dd, J=8.4, 5.7 Hz, 2H), 7.16 (t, J=9.0 Hz, 2H), 4.48 (s, 2H), 3.28 (s, 2H), 3.14 (t, J=5.3 Hz, 2H) 2.84 (t, J=5.3 Hz, 2H).

ES MS M+1=209

EXAMPLE 32

2-(4-Fluorobenzyl)-8,9-dihydroxy-7-{[1-(trifluoroacetyl)piperidin-4-yl]methyl}-3,4-dihydro-2H-pyrido[1,2-a]pyrazine-1,6-dione

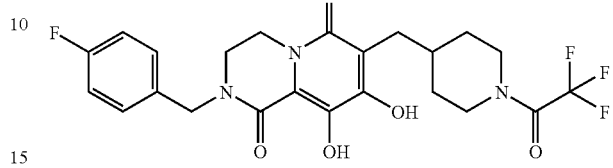

To a solution of 2-(4-fluorobenzyl)-8,9-dihydroxy-7-(piperidin-4-ylmethyl)-3,4-dihydro-2H-pyrido[1,2-a]pyrazine-1,6-dione mono TFA salt [50 mg, 0.125 mmol; Example 31 (Step 3)] in methylene chloride (2 mL), pyridine (12 μL, 0.149 mmol), trifluoroacetic anhydride (26 mg, 0.149 mmol) and a couple drops of DMF were added. After one hour, the reaction mixture was concentrated under vacuum, and the residue was purified by prep HPLC [Gilson semi preparative HPLC system using a Waters Nova Pak column (10×40 mm I.D. cartridge, C18, 6 μM pore size) eluting with 95-5% water (0.10% TFA)/acetonitrile (0.10% TFA) gradient at 35 mL/min]. The product fractions were collected and lyophilized to provide the title compound as a white solid.

$^1$H NMR (400 MHz, d$_6$ DMSO) δ 12.59 (s, 1H), 10.33 (s, 1H), 7.42 (m, 2H), 7.20 (m, 2H), 4.69 (s, 2H), 4.23 (m, 1H), 4.03 (m, 2H), 3.82 (m, 1H), 3.57 (m, 2H), 3.17 (m, 1H), 2.83 (t, 1H, J=12.3 Hz), 2.44 (m, 2H), 1.91 (m, 1H), 1.67 (m, 2H), and 1.17 (m, 2H). High Resolution FT-ICR C$_{23}$H$_{23}$F$_4$N$_3$O$_5$+ H=498.1655; calculated 498.1647.

EXAMPLE 33

7-{[1-(Cyclopropylmethyl)piperidin-3-yl]methyl}-2-(4-fluorobenzyl)-8,9-dihydroxy-3,4dihydro-2H-pyrido[1,2-a]pyrazine-1,6-dione mono TFA salt

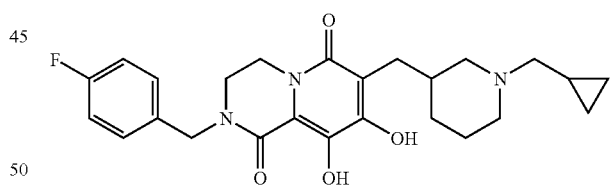

Step 1: 2-(4-Fluorobenzyl)-8,9-dihydroxy-7-(piperidin-3-ylmethyl)-3,4-dihydro-2H-pyrido[1,2-a]pyrazine-1,6-dione mono TFA salt

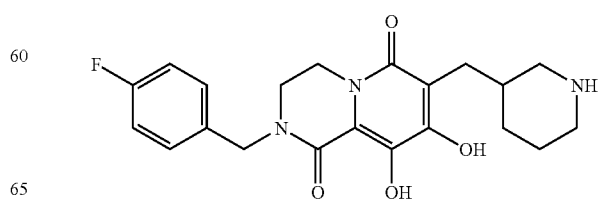

In a manner similar to that described in Example 31 (Step 1 to 3), the title compound was prepared as a white solid using 1-boc-piperidin-3-ylpropionic acid from Astatech in Step 1.

$^1$H NMR (400 MHz, d$_6$ DMSO) δ 12.61 (s, 1H), 10.54 (s, 1H), 8.49 (m, 1H), 8.18 (m, 1H), 7.40 (m, 2H), 7.20 (m, 2H), 4.69 (s, 2H), 4.02 (m, 2H), 3.57 (m, 2H), 3.17 (d, 1H, J=12.0 Hz), 3.06 (d, 1H, J=12.0 Hz), 2.79 (m, 1H), 2.61 (m, 1H), 2.43 (m, 2H), 1.98 (m, 1H), 1.67-1.78 (m, 2H), 1.52 (m, 1H), and 1.24 (m, 1H).

High Resolution FT-ICR C$_{21}$H$_{24}$FN$_3$O$_4$+H=402.1834; calculated 402.1824.

Step 2: 7-{[1-(Cyclopropylmethyl)piperidin-3-yl]methyl}-2-(4-fluorobenzyl)-8,9-dihydroxy-3,4-dihydro-2H-pyrido[1,2-a]pyrazine-1,6-dione mono TFA salt To a solution of 2-(4-fluorobenzyl)-8,9-dihydroxy-7-(piperidin-3-ylmethyl)-3,4-dihydro-2H-pyrido[1,2-a]pyrazine-1,6-dione mono TFA salt (50 mg, 0.097 mmol) in anhydrous methanol (2 mL) under nitrogen, cyclopropanecarboxaldehyde (9 μL, 0.116 mmol) was added and the solution was stirred at room temperature for one hour. Sodium cyanoborohydride (8 mg, 0.129 mmol) was added and the solution was stirred for another hour. The reaction mixture was concentrated under vacuum and the residue was purified by prep "HPLC [Gilson semi preparative HPLC system using a Waters Nova Pak column (10×40 mm I.D. cartridge, C18, 6 μM pore size) eluting with 95-5% water (0.10% TFA)/acetonitrile (0.10% TFA) gradient at 35 mL/min]. The product fractions were collected and lyophilized to provide the title compound as white solid.

$^1$H NMR (400 MHz, d$_6$ DMSO) δ 12.61 (s, 1H), 10.57 (s, 1H), 9.01 (br s, 1H), 7.41 (m, 2H), 7.20 (m, 2H), 4.69 (s, 2H), 4.02 (m, 2H), 3.58 (m, 2H), 3.49 (m, 1H), 3.32 (m, 1H), 2.80-2.99 (m, 3H), 2.68 (m, 1H), 2.38-2.47 (m, 2H), 2.09 (m, 1H), 1.83 (m, 1H), 1.57-1.70 (m, 2H), 1.17 (m,1H), 1.01 (m, 1H), 0.61 (m, 2H), and 0.33 (m, 2H).

High Resolution FT-ICR C$_{25}$H$_{30}$FN$_3$O$_4$+H=456.2296; calculated 456.2293.

EXAMPLE 34

7-[(1-Acetylpiperidin-3-yl)methyl]-2-(4-fluorobenzyl)-8,9-dihydroxy-3,4-dihydro-2H-pyrido[1,2-a]pyrazine-1,6-dione

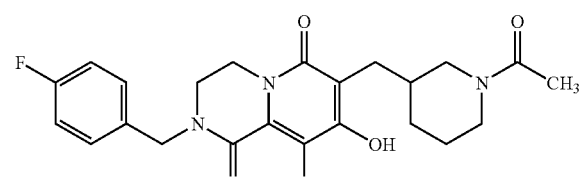

In a manner similar to that described in Example 31 (Step 4), the title compound was prepared as a white solid from 2-(4-fluorobenzyl)-8,9-dihydroxy-7-(piperidin-3-ylmethyl)-3,4-dihydro-2H-pyrido[1,2-a]pyrazine-1,6-dione mono TFA salt from Example 33 (Step 1).

$^1$H NMR (400 MHz, d$_6$ DMSO) δ 12.61 (s, 1H), 10.33 (br s, 1H), 7.40 (m, 2H), 7.19 (m, 2H), 4.68 (s, 2H), 4.28 (m, 1H), 4.02 (m, 2H), 3.69 (m, 1H), 3.59 (m, 2H), 2.92 (m, 1H), 2.32-2.43 (m, 2H), 2.26 (m, 1H), 1.94 (s, 3H), 1.62-1.76 (m, 3H), and 1.13-1.32 (m, 2H). High Resolution FT-ICR C$_{23}$H$_{26}$FN$_3$O$_5$+H=444.1911; calculated 444.1929.

EXAMPLE 35

7-[(1-Acetylpiperidin-2-yl)methyl]-2-(4-fluorobenzyl)-8,9-dihydroxy-3,4-dihydro-2H-pyrido[1,2-a]pyrazine-1,6-dione

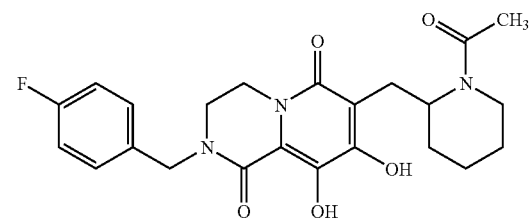

In a manner similar to that described in Example 31 (Step 1 to 4), the title compound was prepared as white solid using 1-boc-piperidin-2-ylpropionic acid from Astatech instead of 1-boc-piperidin-3-ylpropionic acid in Step 1.

$^1$H NMR (400 MHz, d$_6$ DMSO) δ 12.59 (s, 1H), 10.59 (s, 1H), 7.41 (m, 2H), 7.19 (m, 2H), 4.68 (s, 2H), 4.23-4.31 (m, 2H), 4.02 (m, 2H), 3.56 (m, 2H), 2.91 (m, 1H), 2.67-2.78 (m, 2H), 1.95 (s, 3H), and 1.12-1.87 (m, 6H).

High Resolution FT-ICR C$_{23}$H$_{26}$FN$_3$O$_5$+H=444.1912; calculated 444.1929.

EXAMPLE 36

7-{[1-(Cyclopropylmethyl)piperidin-2-yl]methyl}-2-(4-fluorobenzyl)-8,9-dihydroxy-3,4-dihydro-2H-pyrido[1,2-a]pyrazine-1,6-dione mono TFA salt

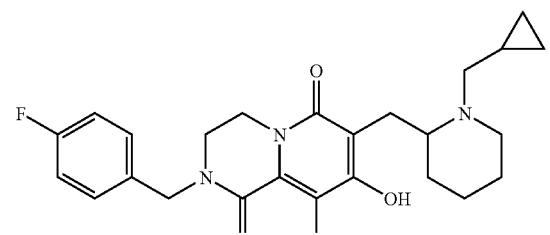

In a manner similar to that described in Example 33, the title compound was prepared as white solid using 1-boc-piperidin-2-ylpropionic acid from Astatech in Step 1.

$^1$H NMR (400 MHz, d$_6$ DMSO) δ 12.62 (s, 1H), 10.95 (d, 1H, J=7.7 Hz), 9.22 (br s, 1H), 7.41 (m, 2H), 7.20 (m, 2H), 4.69 (s, 2H), 4.03 (m, 2H), 3.57 (m, 2H), 3.03-3.42 (m, 5H), 3.00 (m, 1H), 2.78 (m, 1H), 1.20-1.79 (m, 7H), 0.65 (m, 2H), and 0.42 (m, 2H).

High Resolution FT-ICR C$_{25}$H$_{30}$FN$_3$O$_4$+H=456.2291; calculated 456.2293.

EXAMPLE 37

2-(3-Cyanobenzyl)-8,9-dihydroxy-3,4-dihydro-2H-pyrido[1,2-a]pyrazine-1,6-dione

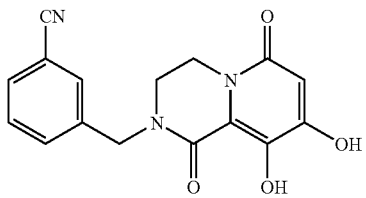

Step 1: tert-Butyl 4-(3-cyanobenzyl)-3-oxopiperazine-1-carboxylate

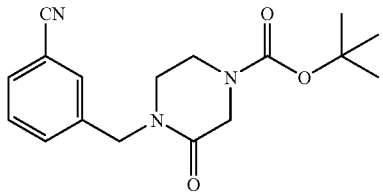

To a stirred solution of 4-Boc-2-piperazinone (2.0 g, 10 mmol), 3-cyanobenzyl bromide (1.8 g, 10 mmol) in DMF (35 mL) at 0° C. was added sodium hydride (480 mg of a 60% suspension in mineral oil, 12 mmol) in several portions over a period of 15 min. The mixture was stirred a 0° C. for 1 h and then at ambient temperature for 1 h. Acetic acid (1 mL) was added and the solvent was removed in vacuo. The residue was partitioned between EtOAc and saturated aqueous sodium bicarbonate solution. The EtOAc layer was separated, dried (MgSO$_4$), filtered, and the solvent was removed in vacuo. The residue was triturated in ether and the white solid was collected by filtration to give 1-(3-cyanobenzyl)4-Boc-2-piperazinone (2.6 g).

LC-MS m/z=316

Step 2: 3-[(4-Acetyl-2-oxopiperazin-1-yl)methyl]benzonitrile

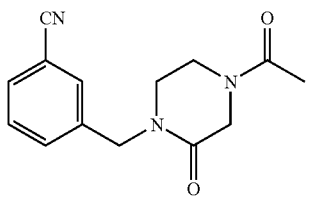

To a stirred solution of 1-(3-cyanobenzyl)-4-Boc-2-piperazinone (2.5 g, 7.9 mmol) in CH$_2$Cl$_2$ (20 mL) at 0° C. was added TFA (10 mL). The mixture was stirred at 0° C. for 2 h, then the solvents were removed in vacuo. The crude 1-(3-cyanobenzyl)-2-piperazinone TFA salt was partitioned between EtOAc (30 mL) and saturated aqueous sodium bicarbonate solution (30 mL). To the stirred two-phase mixture was added acetic anhydride (1.5 mL, 15 mmol) dropwise over a period of 5 min. The mixture was stirred at ambient temperature for 16 h. The EtOAc layer was separated, dried (MgSO$_4$), filtered, and the solvent was removed in vacuo. The residue was purified on a silica gel column using a gradient mobile phase of 2%, 3%, 4% MeOH in CH$_2$Cl$_2$. 1-(3-cyanobenzyl)-4-acetyl-2-piperazinone was obtained as a solid.

$^1$H NMR (CDCl$_3$), 7.4-7.6 ppm (m, 3H), 4.65 (minor) and 4.63 (major) ppm (s, 2H), 4.34 (minor) and 4.23 (major) ppm (s, 2H), 3.81 (major) and 3.68 (minor) ppm (t, J=7 Hz, 2H), 3.34 (minor) and 3.30 (major) ppm (t, J=7 Hz, 2H), 2.13 ppm (s, 3H).

LC-MS m/z=258.

Step 3: 2-(3-Cyanobenzyl)-8,9-dihydroxy-3,4-dihydro-2H-pyrido[1,2-a]pyrazine-1,6-dione In a manner similar to that described in Example 1, Step 3, and 4-acetyl-1-benzylpiperazin-2-one was substituted with 3-[(4-acetyl-2-oxopiperazin-1-yl)methyl]benzonitrile, the title compound was prepared.

$^1$H NMR (400 MHz, CD$_3$OD) δ 7.77 (s, 1H), 7.72-7.66 (m, 2H), 7.6-7.54 (t, 1H), 6.08 (s, 1H), 4.8 (s, 2H), 4.16-4.10 (m, 2H), 3.68-3.62 (m, 2H

EXAMPLE 38

2-(Biphenyl-3-ylmethyl)-8,9-dihydroxy-3,4-dihydro-2H-pyrido[1,2-a]pyrazine-1,6-dione

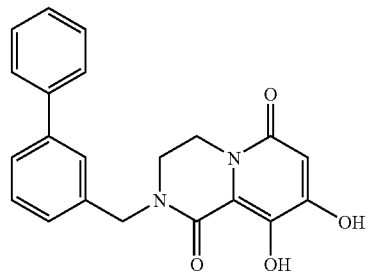

Step 1: 8,9-Dihydroxy-2-(3-iodobenzyl)-3,4-dihydro-2H-pyrido[1,2-a]pyrazine-1,6-dione

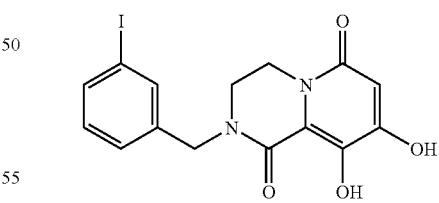

To a cold (0° C.) solution of 4-acetyl-1-(3-iodobenzyl)piperazin-2-one (0.22 g, 0.614 mmol) in DMF (5 mL) under an atmosphere of nitrogen, a solution of sodium bis(trimethylsilyl)amide in THF (1 M, 0.74 mL, 0.74 mmol) was added and stirred at the temperature for 30 min. The resultant solution was treated with diethyl oxalate (16.7 mL, 123 mmol), and stirred at room temperature for 30 min. The resultant mixture was then treated with additional sodium bis(trimethylsilyl)amide in THF (1 M, 2.2 mL, 2.2 mmol) and stirred at room temperature overnight. The product mixture was concentrated under vacuum, and the residue treated with a mixture of aqueous HCl and ethyl acetate. The resultant precipitate was obtained by filtration to provide the title compound as a brown solid.

$^1$H NMR (400 MHz, DMSO-d$_6$) δ 7.63 (m, 2H), 7.30 (d, J=7.3 Hz, 1H), 7.15 (m, 1H), 4.99 (s, 1H), 4.59 (s, 2H), 3.83 (s, 2H), 3.34 (br s, 4H).

ES MS M+1=413

Step 2: 2-(1,1'-Biphenyl-3-ylmethyl)-8,9-dihydroxy-3,4-dihydro-2H-pyrido[1,2-a]pyrazine-1,6-dione A solution of 8,9-dihydroxy-2-(3-iodobenzyl)-3,4-dihydro-2H-pyrido[1,2-a]pyrazine-1,6-dione (0.05 g, 0.121 mmol) in DMF (5 mL) was degassed for 5 minutes with nitrogen and placed under an atmosphere of nitrogen. To this was added phenyl boronic acid (0.015 g, 0.123 mmol), triethylamine (0.051 mL, 0.364 mmol), and bis(tri-t-butylphosphine)palladium(0) (0.003 g, 0.006 mmol) and heated with stirring at 110° C. overnight. The product mixture was concentrated under vacuum, and the residue was triturated with methylene chloride. The resultant precipitate was filtered off and the filtrate concentrated under vacuum. The filtrate residue was subjected to HPLC purification on C-18 stationary phase eluted with water/acetonitrile/TFA mobile phase. Desired fractions were concentrated under vacuum to afford the title compound as off white solid.

$^1$H NMR (400 MHz, CD$_3$OD) δ 7.6 (m, 4H), 7.42 (m, 3H), 7.32 (m, 2H), 6.07 (s, 1H), 4.84 (s, 2H), 4.09 (t, J=5.8 Hz, 2H), 3.63 (t, J=5.8 Hz, 2H).

ES MS M+1=363

EXAMPLE 39

(±)-1-[(Benzyloxy)methyl]-2-(4-fluorobenzyl)4,5-dihydroxy-1,1a,2,8a-tetrahydrocyclo-propa[e]pyrido[1,2-a]pyrazine-3,7-dione Error! Objects cannot be created from editing field codes.

Step 1: (±)-Ethyl 5-acetyl-2-(4-fluorobenzyl)-3-oxo-2,5-diazabicyclo[4.1.0]-heptane-7-carboxylate

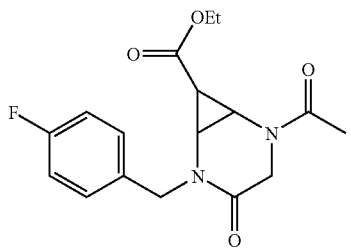

To a suspension of 4-acetyl-1-(4-fluorobenzyl)-3,4-dihydropyrazin-2(1H)-one (5.0 g, 20.0 mmol; Example 2, Step 3) and copper bronze (320 mg, 5.0 mmol) in anhydrous toluene (50 mL) under nitrogen at 120° C. (oil bath) was added ethyl diazoacetate (6.4 mL, 60.0 mmol) via a syringe pump at a speed of 2.5 mL/h. After 3 h, TLC (eluted with ethyl acetate) showed no starting material left. The reaction mixture was cooled to room temperature, filtered and concentrated. The residue was purified by column chromatography on silica gel using ethyl acetate and methanol as eluents to give both exo and endo diastereomers.

Exo diastereomer (Rf higher isomer):

$^1$H NMR (400 MHz, CDCl$_3$) ~6:1 mixture of rotomers δ 7.26-7.32 (m, 2H), 7.02-7.08 (m, 2H), 4.60-4.83 (m, 3H), 4.10-4.20 (m, 2H), 3.50-3.59 (m, 2H), 3.22-3.32 (m, 1H), 2.16 (s, .2.6H), 2.13 (s, 0.4H), 1.63-1.72 (m, 1H), 1.27 (q, J=7.2 Hz, 3H).

ES MS M+1=335.3

Endo diastereomer (Rf lower isomer):

$^1$H NMR (400 MHz, CDCl$_3$) ~1:1 mixture of rotomers δ 7.30-7.35 (m, 2H), 7.04 (t, J=8.6 Hz, 2H), 4.80-4.98 (m, 1.5H), 4.18-4.36 (m, 1.5H), 3.80-4.10 (m, 2.5), 3.56-3.64 (m, 1.5H), 3.28-3.38 (m, 1H), 2.16 (s, .0.5H), 2.13 (s, 0.5H), 2.02-2.06 (m, 1H), 1.14-1.20 (m, 3H).

ES MS M+1=335.3

Step 2: (±)-5-Acetyl-2-(4-fluorobenzyl)-7-(hydroxymethyl)-2,5-diazabicyclo-[4.1.0]heptane-3-one

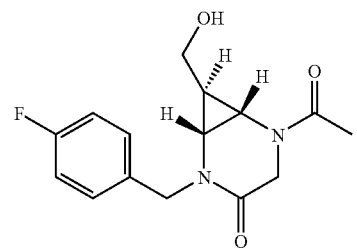

To a solution of the exo isomer of ethyl 5-acetyl-2-(4-fluorobenzyl)-3-oxo-2,5-diazabicyclo[4.1.0]heptane-7-carboxylate (3.3 g, 9.87 mmol) in 32 ml EtOH at room temperature was added sodium borohydride (398 mg, 10.5 mmol). After stirring overnight, the reaction mixture was treated with 200 mL MeOH, stirred for 1 h and then concentrated. The residue was dissolved in dichloromethane (100 mL), treated with 1N HCl (10 mL) and water (20 mL). The aqueous phase was back extracted with chloroform (2×50 mL). The combined organic phases were dried over sodium sulfate, filtered and concentrated. The residue was purified by column chromatography on silica gel using ethyl acetate and methanol as eluents to give title product.

$^1$H NMR (400 MHz, CDCl$_3$) ~3:2 mixture of rotomers δ 7.26-7.35 (m, 21), 7.05 (t, J=8.6 Hz, 2H), 4.42-4.88 (m, 3H), 4.00-4.18 (m, 1H), 3.46-3.76 (m, 2.6H), 3.19 (dd, J=10.0, 9.2 Hz, 0.4H), 3.07 (dd, J=7.9, 3.7 Hz, 0.6H), 2.92 (dd, J=7.9, 4.0Hz, 0.4H), 2.72-2.80 (m, 1H), 2.21 (s, 1.8H), 2.12 (s, 1.2H), 1.16-1.22 (m, 1H).

ES MS M+1=293.3

Step 3: (±)-5-Acetyl-2-(4-fluorobenzyl)-7-[(benzyloxy)methyl]-2,5-diazabicyclo[4.1.0]heptane-3-one

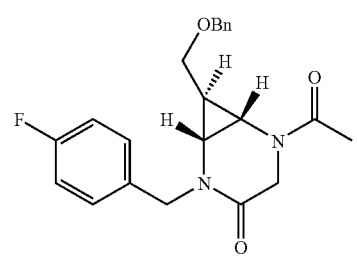

To a solution of 5-acetyl-2-(4-fluorobenzyl)-7-(hydroxymethyl)-2,5-diazabicyclo[4.1.0]heptane-3-one (1.3 g, 4.45 mmol) in 40 mL anhydrous THF under nitrogen, sodium hydride (60% in mineral oil, 231 mg, 5.78 mmol) was added. After stirring for 1 h, benzyl bromide (0.58 ml, 4.89 mmol) in THF (1 mL) was added. The reaction mixture was stirred at room temperature overnight. The reaction was quenched with saturated aqueous ammonium chloride solution. The aqueous layer was extracted with chloroform three times. The combined organic phases were dried over sodium sulfate, filtered and concentrated. The residue was purified by column chromatography on silica gel using hexanes and ethyl acetate as eluents to give the title product.

$^1$H NMR (400 MHz, CDCl$_3$) ~9:1 mixture of rotomers δ 7.22-7.40 (m, 7H), 6.99 (t, J=8.6 Hz, 2H), ), 4.94 (d, J=14.1 Hz, 0.1H), 4.83 (d, J=17.1 Hz, 0.9H), 4.74 (d, J=14.3 Hz, 0.9H), 4.44-4.50 (m, 2.9H), 4.26 (d, J=14.1 Hz, 0.1H), 4.08 (d, J=16.5 Hz, 0.1H), 3.95 (d, J=16.3 Hz, 0.1H), 3.78 (dd, J=10.2, 4.7 Hz, 0.1H), 3.46 (d, J=17.1 Hz, 0.9H), 3.37 (dd, J=10.0, 5.8 Hz, 0.9H), 3.26 (dd, J=10.0, 6.7 Hz, 0.9H), 3.13 (dd, J=10.2, 7.8 Hz, 0.1H), 3.03 (dd, J=7.9, 3.5 Hz, 1H), 2.71 (dd, J=7.9, 3.6 Hz, 1H), 2.20 (s, .2.7H), 2.10 (s, 0.3H), 1.16-1.24 (m, 1H).

ES MS M+1=383.3

Step 4: (±)-1-[(Benzyloxy)methyl]-2-(4-fluorobenzyl)-4,5-dihydroxy-1,1a,2,8a-tetrahydrocyclopropa[e]pyrido[1,2-a]pyrazine-3,7-dione To a cold (0° C.) solution of 5-acetyl-2-(4-fluorobenzyl)-7-[(benzyloxy)-methyl]-2,5-diazabicyclo[4.1.0]heptane-3-one (700 mg, 1.83 mmol) in DMF (10 mL) under nitrogen, a solution of lithium bis(trimethylsilyl)amide in THF (1.0 M, 2.0 mL, 2.0 mmol) was added. After 30 min, diethyl oxalate (401 mg, 2.74 mmol) in DMF (2 mL) was added. After stirring for 1 h at room temperature, the resultant mixture was treated with additional lithium bis(trimethylsilyl)amide (1.0 M, 7.1 mL, 7.1 mmol), and stirred at room temperature overnight. The reaction mixture was treated with 1 N HCl, concentrated under vacuum. The residue was partitioned between brine and chloroform. The aqueous layer was extracted with chloroform twice. The combined organic phases were dried over sodium sulfate, filtered and concentrated. The residue was subjected to HPLC purification on C-18 stationary phase eluted with water/acetonitrile/TFA mobile phase. Collection and lyophilization of appropriate fractions provided the title compound.

$^1$H NMR (400 MHz, CD$_3$OD) δ 7.42 (dd, J=8.6, 5.5 Hz, 2H), ), 7.26-7.36 (m, 5H), 7.02 (t, J=8.7 Hz, 2H), 6.09 (s, 1H), 4.96 (d, J=14.4 Hz, 1H), 4.69 (d, J=14.5 Hz, 1H), 4.48 (s, 2H), 3.81 (dd, J=8.8, 4.6 Hz, 1H), 3.57 (dd, J=10.6, 5.3 Hz, 1H), 3.31-3.34 (m, 1H), 3.14 (dd, J=8.8, 4.2 Hz, 1H), 1.20-1.25 (m, 1H).
ES MS M+1=437.2

EXAMPLE 40

(±)-1-(Methoxymethyl)-2-(4-fluorobenzyl)-4,5-dihydroxy-1,1a,2,8a-tetrahydrocyclo-propa[e]pyrido[1,2-a]pyrazine-3,7-dione

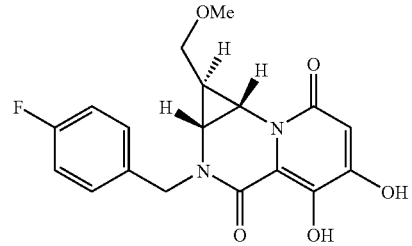

The title compound was prepared using a procedure similar to that described in Example 39, except that benzyl bromide was substituted with methyl iodide in Step 3.

$^1$H NMR (400 MHz, CDCl$_3$) δ 7.40 (dd, J=8.6, 5.3 Hz, 2H), ), 7.07 (t, J=8.4 Hz, 2H), 6.25 (s, 1H), 4.81 (d, J=14.3 Hz, 1H), 4.75 (d, J=14.5 Hz, 1H), 3.87 (dd, J=8.8, 4.4 Hz, 1H), 3.59 (dd, J=10.6, 5.0 Hz, 1H), 3.31 (s, 3H), 3.18 (dd, J=10.6, 7.1 Hz, 1H), 2.98 (dd, J=8.7, 4.2 Hz, 1H), 1.12-1.18 (m, 1H).
ES MS M+1=361.2

EXAMPLE 41

(±)-1-[(Allyloxy)methyl]-2-(4-fluorobenzyl)-4,5-dihydroxy-1,1a,2,8a-tetrahydrocyclo-propa[e]pyrido[1,2-a]pyrazine-3,7-dione

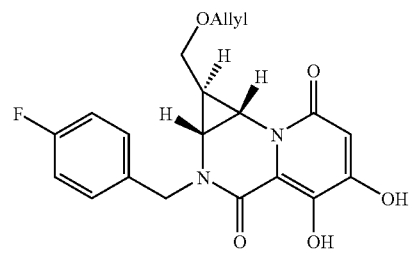

The title compound was prepared using a procedure similar to that described in Example 39, except that benzyl bromide was substituted with allyl bromide in Step 3.

$^1$H NMR (400 MHz, CDCl$_3$) δ 7.40 (dd, J=8.6, 5.1 Hz, 2H), ), 7.06 (t, J=8.6 Hz, 2H), 6.28 (s, 1H), 5.82-5.90 (m, 1H), 5.19-5.28 (m, 2H), 4.81 (d, J=14.1 Hz, 1H), 4.75 (d, J=14.1 Hz, 1H), 3.92-3.98 (m, 2H), 3.87 (dd, J=8.6, 4.4 Hz, 1H), 3.70 (dd, J=10.6, 4.7Hz, 1H), 3.19 (dd, J=10.6, 7.1 Hz, 1H), 2.99 (dd, J=8.6, 4.0 Hz, 1H), 1.12-1.18 (m, 1H).
ES MS M+1=387.2

EXAMPLE 42

(±)-1-(Ethoxymethyl)-2-(4-fluorobenzyl)-4,5-dihydroxy-1,1a,2,8a-tetrahydrocyclo-propa[e]pyrido[1,2-a]pyrazine-3,7-dione

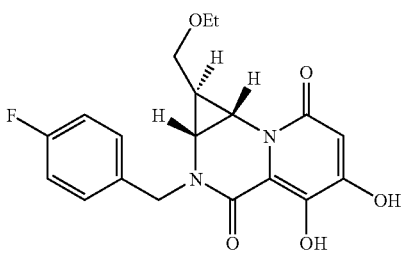

The title compound was prepared using a procedure similar to that described in Example 39, except that benzyl bromide was substituted with iodoethane in Step 3.

$^1$H NMR (400 MHz, CDCl$_3$) δ 13.0 (s, 1H), 7.41 (dd, J=8.0, 5.6 Hz, 21H), ), 7.07 (t, J=8.4 Hz, 2H), 6.26 (s, 1H), 4.81 (d, J=14.3 Hz, 1H), 4.77 (d, J=14.5 Hz, 1H), 3.86 (dd, J=8.6, 4.4 Hz, 1H), 3.65 (dd, J=10.6, 4.8 Hz, 1H), 3.40-3.50 (m, 2H), 3.19 (dd, J=10.6, 7.3 Hz, 1H), 2.99 (dd, J=8.7, 4.1 Hz, 1H), 1.12-1.20 (m, 4H).

ES MS M+1=375.3

EXAMPLE 43

(±)-1-(n-Propoxymethyl)-2-(4-fluorobenzyl)-4,5-dihydroxy-1,1a,2,8a-tetrahydrocyclo-propa[e]pyrido[1,2-a]pyrazine-3,7-dione

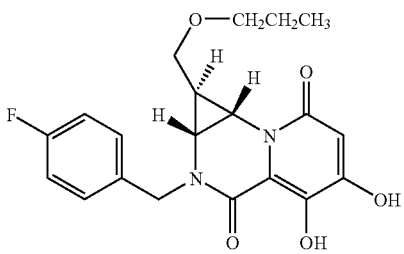

The title compound was prepared using a procedure similar to that described in Example 39, except that benzyl bromide was substituted with 1-iodopropane in Step 3.

$^1$H NMR (400 MHz, CDCl$_3$) δ 13.0 (s, 1H), 7.41 (dd, J=8.5, 5.3 Hz, 2H), ), 7.07 (t, J=8.4 Hz, 2H), 6.24 (s, 1H), 4.81 (d, J=14.3 Hz, 1H), 4.75 (d, J=14.3 Hz, 1H), 3.85 (dd, J=8.4, 4.2 Hz, 1H), 3.68 (dd, J=10.6, 4.5 Hz, 1H), 3.30-3.40 (m, 2H), 3.18 (dd, J=10.6, 7.3 Hz, 1H), 2.99 (dd, J=8.6, 4.0 Hz, 1H), 1.52-1.60 (m, 2H), 1.15-1.20 (m, 1H), 0.92 (t, J=7.3 Hz, 3H).

ES MS M+1=389.3

EXAMPLE 44

2-[1-(4-Fluorophenyl)ethyl]-8,9-dihydroxy-3,4-dihydro-2H-pyrido[1,2-a]pyrazine-1,6-dione

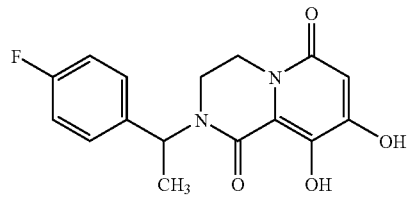

The title compound was prepared using a procedure similar to that described in Example 1, Steps 1 to 3, except that benzyl bromide (Step 1) was substituted with 1-[4-fluorophenyl]-1-bromoethane.

$^1$H NMR (400 MHz, DMSO-d$_6$) δ 12.36 (s, 1H), 11.05 (br s, 1H), 7.43 (dd, J=8.5, 5.6 Hz, 2H), 7.21 (t, J=8.5 Hz, 2H), 5.92 (s, 1H), 5.80 (q, J=7.1 Hz, 1H), 4.05 (m, 1H), 3.74 (m, 1H), 3.54 (m, 1H), 3.15 (m, 1H), 1.55 (d, J=7.0 Hz, 3H).

ES MS M+1=319

EXAMPLE 45

5-(4-Fluorobenzyl)-7,8-dihydroxy-5H-pyrido[1,2-a]quinoxaline-6,10-dione

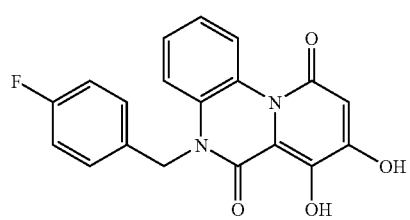

Step 1: 4-Acetyl-3,4-dihydroquinoxalin-2(1H)-one

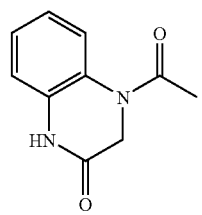

To a cold (0° C.) solution of 3,4-dihydroquinoxalin-2(1H)-one (1.0 g, 6.7 mmol; J. Med. Chem. 758, 1994) and N,N-diisopropyl-N-ethylamine (1.7 mL, 10.1 mmol) in dichloromethane (30 mL) under an atmosphere of nitrogen, acetic anhydride (0.76 mL, 8.1 mmol) was added and stirred at room temperature overnight. The resultant solution was concentrated under vacuum. The residue was subjected to column chromatography on silica gel eluting with a 1% methanol in chloroform. Collection and concentration of appropriate fractions provided the acetylation product.

$^1$H NMR (400 MHz, CDCl$_3$) δ 10.1 (br s, 1H), 7.23-7.04 (m, 4H), 4.53 (br, s, 2H), 2.28 (br s, 3H).
ES MS M+1=191

Step 2: 4-Acetyl-1-(4-fluorobenzyl)-3,4-dihydroquinoxalin-2(1H)-one

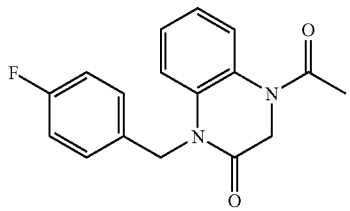

To a cold (0° C.) solution of 4-acetyl-3,4-dihydroquinoxalin-2(1H)-one (0.13 g, 0.68 mmol) in DMF (3.5 mL) under an atmosphere of nitrogen, a solution of lithium bis(trimethylsilyl)amide in THF (0.75 mL, 0.75 mmol) was added and stirred at the temperature for 30 min. The resultant solution was treated with 4-fluorobenzyl bromide (0.089 mL, 0.72 mmol), and stirred at room temperature for 3 hours. The product mixture was concentrated under vacuum, and the residue partitioned between aqueous HCl and ethyl acetate. The organic extract was washed with brine, dried over anhydrous magnesium sulfate, filtered, and concentrated under vacuum. The residue was subjected to column chromatography on silica gel eluting with 50% ethyl acetate in hexane. Collection and concentration of appropriate fractions provided the title compound.
ES MS M+1=299

Step 3: 5-(4-Fluorobenzyl)-7,8-dihydroxy-5H-pyrido[1,2-a]quinoxaline-6,10-dione

To a cold (0° C.) solution of 4-acetyl-1-(4-fluorobenzyl)-3,4-dihydro-quinoxalin-2(1H)-one (0.15 g, 0.52 mmol) in DMF (5 mL) under an atmosphere of nitrogen, a solution of lithium bis(trimethylsilyl)amide in THF (0.57 mL, 0.57 mmol) was added and stirred at the temperature for 30 min. The resultant solution was treated with diethyl oxalate (0.078 mL, 0.57 mmol), and stirred at room temperature overnight. The resultant mixture was then treated with additional lithium bis(trimethylsilyl)amide in THF (1.6 mL, 1.6 mmol) and stirred at room temperature for 6 h. The product mixture was concentrated under vacuum, and the residue partitioned between aqueous HCl and dichloromethane. The organic extract was dried over anhydrous magnesium sulfate, filtered, and concentrated under vacuum. The residue was subjected to HPLC purification on C-18 stationary phase eluted with water/acetonitrile/TFA mobile phase. Collection and lyophilization of appropriate fractions provided the title compound as white solid.
$^1$H NMR (400 MHz, DMSO-d$_6$) δ 12.86 (s, 1H), 11.53 (br s, 1H), 9.24 (d, J=8.1 Hz, 1H), 7.42 (dd, J=8.2, 5.7 Hz, 2H), 7.20-7.13 (m, 5H), 6.18 (s, 1H), 5.36 (s, 2H).
ES MS M+1=353

EXAMPLE 46

5-(4-Fluorobenzyl)-7,8-dihydroxy-5H-pyrido[1,2-a:3',2'-e]pyrazine-6,10-dione

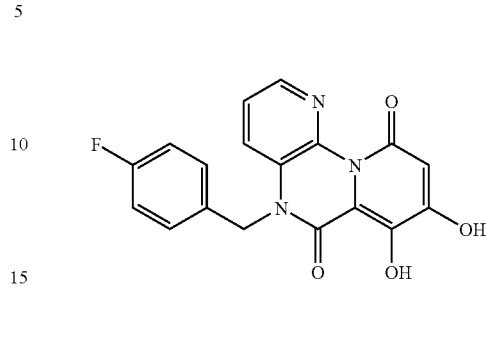

Step 1: N$^3$-(4-Fluorobenzyl)pyridine-2,3-diamine

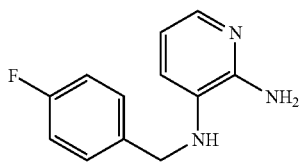

To a suspension of 2,3-diaminopyridine (3.0 g, 27.5 mmol) and dried molecular sieves (4 Å) in THF (230 mL), 4-fluorobenzaldehyde (4.56 mL, 42.3 mmol) was added. The resultant mixture was stirred at room temperature overnight, filtered through a pad of Celite, and the filtrate concentrated under vacuum. The residue was subjected to column chromatography on silica gel eluting with a 25-100% ethyl acetate in hexane gradient. Collection and concentration of appropriate fractions provided the imine intermediate. To a cold (0° C.) solution of resultant imine (3.0 g, 13.9 mmol) in anhydrous ethanol (50 mL), sodium borohydride (1.04 g, 28 mmol) was added portionwise. The resultant solution was stirred at room temperature overnight, and quenched with methanol. The product mixture was concentrated under vacuum, and the residue partitioned between ethyl acetate and water. The organic extract was dried over anhydrous sodium sulfate, filtered and concentrated under vacuum to provide the title compound.
$^1$H NMR (400 MHz, CDCl$_3$) δ 7.61 (d, J=4.7 Hz, 1H), 7.33 (dd, J=8.2, 5.8 Hz, 2H), 7.04 (br t, J=8.2 Hz, 2H), 6.78 (d, J=7.7 Hz, 1H), 6.67 (dd, J=7.7, 4.7 Hz, 1H), 4.26 (d, J=4.2 Hz, 2H), 3.56 (br s, 2H).
ES MS M+1=218

Step 2: 4-Acetyl-1-(4-fluorobenzyl)-3,4-dihydropyrido[2,3-b]pyrazin-2(1H)-one

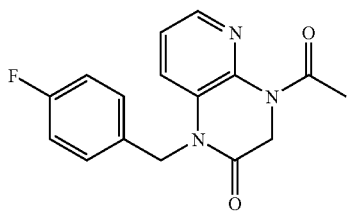

To a cold (0° C.) solution of N³-(4-fluorobenzyl)pyridine-2,3-diamine (4.4 g, 20.28 mmol) and pyridine (2.5 mL, 31 mmol) in dichloromethane (100 mL) under an atmosphere of nitrogen, chloroacetyl chloride (1.8 mL, 22 mol) was added. The resultant solution was stirred at room temperature overnight. The product mixture was concentrated under vacuum, and the residue was partitioned between aqueous HCl and ethyl acetate. The organic extract was washed with brine, dried over anhydrous magnesium sulfate, filtered, and concentrated under vacuum. The residue was subjected to column chromatography on silica gel eluting with 50-100% ethyl acetate in hexane gradient. Collection and concentration of appropriate fractions provided the bis chloroacetylated intermediate. ES MS M+1=370.

To a cold (0° C.) solution of the bis chloroacetylation product (120 mg, 0.32 mmol) in anhydrous THF (3 mL), a solution of lithium bis(trimethylsilyl)amide in THF (0.32 mL, 0.32 mmol) was added. The reaction mixture was stirred at room temperature for a half hour and concentrated under vacuum. The residue was partitioned between aqueous ammonium chloride and ethyl acetate. The organic extract was washed with brine, dried over anhydrous magnesium sulfate, filtered, and concentrated under vacuum. The residue was subjected to column chromatography on silica gel eluting with an ethyl acetate in hexane gradient. Collection and concentration of appropriate fractions provided the cyclization intermediate 4-chloro-acetyl-1-(4-fluorobenzyl)-3,4-dihydropyrido[2,3-b]pyrazin-2(1H)-one as white solid.

A mixture of 4-chloro-acetyl-1-(4-fluorobenzyl)-3,4-dihydropyrido[2,3-b]pyrazin-2(1H)-one (2.2 g, 5.96 mmol) and 10% Pd/C (0.5 g) in methanol (50 mL) was stirred under an atmosphere of hydrogen (1 atm) at room temperature for 5 hours. The product mixture was filtered through a pad of Celite, and concentrated under vacuum. The residue was subjected to column chromatography on silica gel eluting with ethyl acetate and hexane. Collection and concentration of appropriate fractions provided the title compound.

¹H NMR (400 MHz, CDCl₃) δ 8.09 (d, J=4.8 Hz, 1H), 7.24-7.01 (m, 6H[), 5.11 (s, 2H), 4.72 (s, 2H), 2.48 (s, 3H).

ES MS M+1=300

Step 3: 5-(4-Fluorobenzyl)-7,8-dihydroxy-5H-pyrido[1,2-a:3',2'-e]pyrazine-6,10-dione To a cold (0° C.) solution of 4-acetyl-1-(4-fluorobenzyl)-3,4-dihydro-pyrido[2,3-b]pyrazin-2(1H)-one (0.275 g, 0.903 mmol) in DMF (10 mL) under an atmosphere of nitrogen, a solution of lithium bis(trimethylsilyl)amide in THF (1.44 mL, 1.44 mmol) was added and stirred at the temperature for 30 min. The resultant solution was treated with dimethyl oxalate (0.21 g, 1.8 mmol), and stirred at room temperature overnight. The resultant mixture was then treated with additional lithium bis(trimethylsilyl)amide in THF (3.6 mL, 3.6 mmol) and stirred at room temperature for 6 h. The product mixture was concentrated under vacuum, and the residue partitioned between aqueous HCl and dichloromethane. The organic extract was dried over anhydrous magnesium sulfate, filtered, and concentrated under vacuum. The residue was subjected to HPLC purification on C-18 stationary phase eluted with water/acetonitrile/TFA mobile phase. Collection and lyophilization of appropriate fractions provided the title compound as white solid.

¹H NMR (400 MHz, DMSO-d₆) δ 8.18 (d, J=3.7 Hz, 1H), 7.64 (d, J=7.5 Hz, 1H), 7.45 (dd, J=8.2, 5.7 Hz, 2H), 7.33 (dd, J=8.2, 4.7 Hz, 1H), 7.18 (t, J=8.8 Hz, 2H), 6.10 (s, 1H), 5.32 (s, 2H).

ES MS M+1=354

EXAMPLE 47

5-(4-Fluorobenzyl)-7,8-dihydroxy-5H-pyrido[1,2-a:2',3'-e]pyrazine-6,10-dione

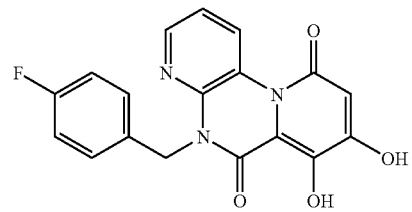

Step 1: N²-(4-Fluorobenzyl)pyridine-2,3-diamine

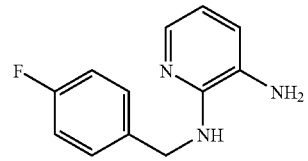

A mixture of 2-fluoro-3-nitropyridine (2.5 g, 17.6 mmol), 4-fluorobenzyl-amine (4.40 g, 35.2 mmol), and N,N-diisopropyl-N-ethylamine (4.55 g, 35.2 mmol) in anhydrous acetonitrile (30 mL) was stirred at room temperature for 1 hour. The reaction mixture was concentrated under vacuum, and the residue partitioned between water and ethyl acetate. The organic extract was dried over anhydrous magnesium sulfate, filtered, and concentrated under vacuum. The residue was subjected to column chromatography on silica gel eluting with 15% ethyl acetate in hexane. Collection and concentration of appropriate fractions provided the 2-(4-fluorobenzylamino)-3-nitropyridine intermediate as yellow solid.

A mixture of 2-(4-fluorobenzylamino)-3-nitropyridine (1.0 g, 4.05 mmol) and 10% Pd/C (0.3 g) in methanol (50 mL) was stirred under an atmosphere of hydrogen (1 atm) at room temperature for 5 hours. The product mixture was filtered through a pad of Celite, and concentrated under vacuum. The residual methanol was removed by co-evaporation with benzene. The resultant N²-(4-Fluorobenzyl)pyridine-2,3-diamine was used in the following step without further purification.

¹H NMR (400 MHz, CDCl₃) δ 7.79 (d, J=4.7 Hz, 1H), 7.38 (dd, J=8.2, 5.8 Hz, 2H), 7.05 (br t, J=8.2 Hz, 2H), 6.88 (d, J=7.7 Hz, 1H), 6.58 (dd, J 7.7, 4.7 Hz, 1H), 4.60 (d, J=4.2 Hz, 2), 3.49 (br s,2H).

ES MS M+1=218

Step 2: 1-Acetyl-4-(4-fluorobenzyl)-1,4-dihydropy-rido[2,3-b]pyrazin-3(2H)-one

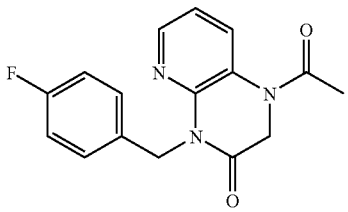

The title compound was prepared using a procedure similar to that described in Example 46, Step 2, except that N³-(4-luorobenzyl)pyridine-2,3-diamine was substituted with N²-(4-fluorobenzyl)pyridine-2,3-diamine.

Step 3: 5-(4-Fluorobenzyl)-7,8-dihydroxy-5H-pyrido [1,2-a:2',3'-e]pyrazine-6,10-dione The title compound was prepared using a procedure similar to that described in Example 46, Step 3, except that 4-acetyl-1-(4-fluorobenzyl)-3,4-dihydro-pyrido[2,3-b]pyrazin-2 (1H)-one was substituted with 1-acetyl4-(4-fluorobenzyl)-1,4-dihydropyrido[2,3-b]pyrazin-3 (2H)-one.

¹H NMR (400 MHz, DMSO-d$_6$) δ 12.76 (s, 1H), 11.65 (br s, 1H), 9.72 (d, J=8.6 Hz, 1H), 8.22 (d, J=4.0 Hz, 1H), 7.44 (dd, J=8.2, 5.7 Hz, 2H), 7.25 (m, 1H), 7.11 )t, J=8.8 Hz, 2H), 6.17 (s, 1H), 5.44 (s, 2H).

ES MS M+1=354

EXAMPLE 48

Oral Compositions

As a specific embodiment of an oral composition of a compound of this invention, 50 mg of compound of Example 1 is formulated with sufficient finely divided lactose to provide a total amount of 580 to 590 mg to fill a size 0 hard gelatin capsule. Encapsulated oral compositions containing any one of the compounds of Examples 2-47 can be similarly prepared.

EXAMPLE 49

HIV Integrase Assay: Strand Transfer Catalyzed by Recombinant Integrase

Assays for the strand transfer activity of integrase were conducted in accordance with WO 02/30930 for recombinant integrase. Representative compounds of the present invention exhibit inhibition of strand transfer activity in this assay. For example, the compounds prepared in Examples 1-47 were tested in the integrase assay and all were found to have IC$_{50}$'s less than 5 micromolar, and all but the compounds prepared in Examples 37, 38 and 44 were found to have ICIC$_{50}$'s less than 0.5 micromolar.

Further description on conducting the assay using preassembled complexes is found in Wolfe, A. L. et al., *J. Virol.* 1996, 70: 1424-1432, Hazuda et al., *J. Virol.* 1997, 71: 7005-7011; Hazuda et al., *Drug Design and Discovery* 1997, 15: 17-24; and Hazuda et al., *Science* 2000, 287: 646-650.

EXAMPLE 50

Assay for Inhibition of HIV Replication

Assays for the inhibition of acute HIV infection of T-lymphoid cells were conducted in accordance with Vacca, J. P. et al., *Proc. Natl. Acad. Sci. USA* 1994, 91: 4096. Representative compounds of the present invention exhibit inhibition of HIV replication in this assay. For example, the compounds prepared in Examples 1-47 were tested in the present assay and all were found to have IC$_{95}$'s less than 10 micromolar. In particular, the compounds of Examples 1-18 were found to have IC$_{95}$'s less than 5 micromolar, and the compounds of Examples 2, 6, 8-12, 14, 15, 25, 27-30, 34, 35, 42 and 43 were found to have IC$_{95}$'s less than 1 micromolar.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of Formula (I), or a pharmaceutically acceptable salt thereof:

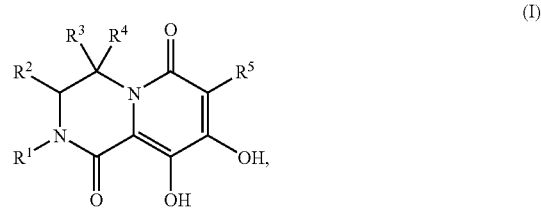

wherein

R¹ is —C$_{1-4}$ alkyl mono-substituted with aryl; wherein the aryl is optionally substituted with from 1 to 4 substituents each of which is independently (1) —C$_{1-4}$ alkyl, optionally mono-substituted with —OH, —O—C$_{1-4}$ alkyl, —O—C$_{1-4}$ haloalkyl, —CN, —N(R$^a$R$^b$), —C(=O)N(R$^a$R$^b$), —C(=O)R$^a$, —CO$_2$R$^c$, —S(O)$_n$R$^c$, —SO$_2$N(R$^a$R$^b$), —N(R$^a$)C(=O) R$^b$, —N(R$^a$)CO$_2$R$^c$, —N(R$^a$)SO$_2$R$^c$, —N(R$^a$)SO$_2$N (R$^a$R$^b$), —OC(=O)N(R$^a$R$^b$), or —N(R$^a$)C(=O)N (R$^a$R$^b$), (2) —O—C$_{1-4}$ alkyl, optionally mono-substituted with —OH, —O—C$_{1-4}$ alkyl, —O—C$_{1-4}$ haloalkyl, —S(O)$_n$ R$^c$, —N(R$^a$)—CO$_2$R$^c$, —C(=O)N(R$^a$R$^b$), —SO$_2$N (R$^a$R$^b$), —N(R$^a$)C(=O)R$^b$, —N(R$^a$)CO$_2$R$^c$, —N(R$^a$) SO$_2$R$^c$, —N(R$^a$)SO$_2$N(R$^a$R$^b$), —OC(=O)N(R$^a$R$^b$), or —N(R$^a$)C(=O)N(R$^a$R$^b$), (3) —C$_{1-4}$ haloalkyl,
(4) —O—C$_{1-4}$ haloalkyl,
(5) —OH,
(6) halo,
(7) —CN,
(8) —NO$_2$,
(9) —N(R$^a$R$^b$),
(10) —SR$^c$,
(11) —S(=O)R$^c$,
(12) —SO$_2$R$^2$,
(13) —N(R$^a$)SO$_2$R$^c$,
(14) —SO$_2$N(R$^a$R$^b$),
(15) —N(R$^a$)C(=O)R$^b$,
(16) —N(R$^a$)CO$_2$R$^c$, or
(17) phenyl;

$R^2$ is —H or —$C_{1-6}$ alkyl;

$R^3$ is —H, —$C_{1-6}$ alkyl, —$C_{1-6}$ haloalkyl, or —$C_{1-6}$ alkyl substituted with one of —OH, —O—$C_{1-6}$ alkyl, —O—$C_{1-6}$ haloalkyl, —CN, —$NO_2$, —N($R^aR^b$), —C(=O)N($R^aR^b$), —C(=O)$R^a$, —$CO_2R^c$, —S(O)$_nR^c$, —$SO_2$N($R^aR^b$), —N($R^a$)C(=O)$R^b$, —N($R^a$)$CO_2R^c$, —N($R^a$)$SO_2R^c$, —N($R^a$)$SO_2$N($R^aR^b$), —OC(=O)N($R^aR^b$), or —N($R^a$)C(=O)N($R^aR^b$);

$R^4$ is:
(1) —H,
(2) —$C_{1-6}$ alkyl optionally substituted with one of —OH, —O—$C_{1-6}$ alkyl, —O—$C_{1-6}$ haloalkyl, —CN, —$NO_2$, —N($R^aR^b$), —C(=O)N($R^aR^b$), —C(=O)$R^a$, —$CO_2R^c$, —S(O)$_nR^c$, —$SO_2$N($R^aR^b$), —N($R^a$)—C($R^b$)=O, —N($R^a$)$SO_2R^c$, —N($R^a$)$SO_2$N($R^aR^b$), —OC(=O)N($R^aR^b$), —N($R^a$)C(=O)N($R^aR^b$), —O—$C_{1-6}$ alkyl-C(=O)N($R^aR^b$), —S—$C_{1-6}$ alkyl—C(=O)N($R^aR^b$), —N($R^a$)—$C_{1-6}$ alkyl-C(=O)N($R^aR^b$), or —N($SO_2R^c$)—$C_{1-6}$ alkyl-C(=O)N($R^aR^b$),
(3) —$C_{1-6}$ haloalkyl,
(4) —C(=O)$R^a$,
(5) —$CO_2R^c$,
(6) —C(=O)N($R^aR^b$),
(7) —$SO_2$N($R^aR^b$),
(8) —$C_{2-6}$ alkenyl,
(9) —$C_{2-6}$ alkenyl-C(=O)—N($R^a$)$_2$,
(10) —$C_{2-5}$ alkynyl,
(11) —$C_{2-5}$ alkynyl-$CH_2$N($R^a$)$_2$,
(12) —$C_{2-5}$ alkynyl-$CH_2OR^a$,
(13) —$C_{2-5}$ alkynyl-$CH_2$S(O)$_nR^c$, or
(14) —$R^k$,
(15) —$C_{1-6}$ alkyl substituted with $R^k$,
(16) —$C_{1-6}$ haloalkyl substituted with $R^k$,
(17) —$C_{1-6}$ alkyl-O—$R^k$,
(18) —$C_{1-6}$ alkyl-O—$C_{1-6}$ alkyl-$R^k$,
(19) —$C_{1-6}$ alkyl-S(O)$_n$—$R^k$,
(20) —$C_{1-6}$ alkyl-S(O)$_n$—$C_{1-6}$ alkyl—$R^k$,
(21) —$C_{1-6}$ alkyl-N($R^a$)—$R^k$,
(22) —$C_{1-6}$ alkyl-N($R^a$)—$C_{1-6}$ alkyl-$R^k$,
(23) —$C_{1-6}$ alkyl-N($R^a$)—$C_{1-6}$ alkyl-$OR^k$, with the proviso that the —N($R^a$)— moiety and the —$OR^k$ moiety are not both attached to the same carbon of the —$C_{1-6}$ alkyl-moiety,
(24) —$C_{1-6}$ alkyl-C(=O)—$R^k$,
(25) —$C_{1-6}$ alkyl-C(=O)N($R^a$)—$R^k$,
(26) —$C_{1-6}$ alkyl-N($R^a$)C(=O)—$R^k$,
(27) —$C_{1-6}$ alkyl-C(=O)N($R^a$)—$C_{1-6}$ alkyl-$R^k$, or
(28) —$C_{1-6}$ alkyl-N($R^a$)—$C_{0-6}$ alkyl-S(O)$_nR^k$;
wherein $R^k$ is
(i) aryl, which is optionally substituted with from 1 to 5 substituents each of which is independently —$C_{1-6}$ alkyl, —$C_{1-6}$ alkyl-OH, —$C_{1-6}$ alkyl-O—$C_{1-6}$ alkyl, —$C_{1-6}$ alkyl-O—$C_{1-6}$ haloalkyl, —$C_{1-6}$ alkyl-N($R^aR^b$), —$C_{1-6}$ alkyl-C(=O)N($R^aR^b$), —$C_{1-6}$ alkyl-C(=O)$R^a$, —$C_{1-6}$ alkyl-$CO_2R^c$, —$C_{1-6}$ alkyl-S(O)$_nR^c$, —O—$C_{1-6}$ alkyl, —$C_{1-6}$ haloalkyl, —O—$C_{1-6}$ haloalkyl, —OH, halo, —N($R^aR^b$), —C(=O)N($R^aR^b$), —C(=O)$R^a$, —$CO_2R^c$, —S(O)$_nR^c$, or —$SO_2$N($R^aR^b$);
(ii) a 4- to 7-membered saturated or mono-unsaturated heterocyclic ring containing at least one carbon atom and from 1 to 4 heteroatoms independently selected from N, O and S, wherein the heterocyclic ring is:
(a) optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and (b) optionally mono-substituted with aryl or HetA;
wherein HetA is a 5- or 6-membered heteroaromatic ring containing from 1 to 4 heteroatoms independently selected from N, O and S, wherein the heteroaromatic ring is optionally fused with a benzene ring, and HetA is optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, or oxo; or
(iii) a 5- or 6-membered heteroaromatic ring containing from 1 to 4 heteroatoms independently selected from N, O and S, wherein the heteroaromatic ring is optionally substituted with from optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, or oxo;

or alternatively $R^3$ and $R^4$ are joined together to form $C_{5-8}$ cycloalkyl or a 5- to 7-membered saturated heterocyclic ring containing from 1 to 4 heteroatoms independently selected from N, O and S; wherein
the cycloalkyl is optionally substituted with from 1 to 3 substituents each of which is independently halo, —$C_{1-6}$ alkyl, or —O—$C_{1-6}$ alkyl; and
the heterocyclic ring is optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, or oxo;

$R^5$ is:
(1) —H,
(2) —$C_{1-6}$ alkyl,
(3) —$C_{1-6}$ alkyl-N($R^aR^b$),
(4) —$C_{1-6}$ alkyl-C(=O)N($R^aR^b$),
(5) —$C_{1-6}$ alkyl-C(=O)$R^a$,
(6) —$C_{1-6}$ alkyl-$CO_2R^c$,
(7) —$C_{1-6}$ alkyl-$SR^c$,
(8) —$C_{1-6}$ alkyl-S(=O)$R^c$,
(9) —$C_{1-6}$ alkyl-$SO_2R^c$,
(10) —$C_{1-6}$ alkyl-$SO_2$N($R^aR^b$)
(11) —$C_{1-6}$ haloalkyl,
(12) —O—$C_{1-6}$ alkyl,
(13) —O—$C_{1-6}$ haloalkyl,
(14) halo,
(15) —CN,
(16) —C(=O)$R^a$,
(17) —$CO_2R^c$,
(18) —$SR^c$,
(19) —S(=O)$R^c$,
(20) —$SO_2R^c$,
(21) —N($R^aR^b$),
(22) —C(=O)N($R^aR^b$), or
(23) —$SO_2$N($R^aR^b$);
(24) aryl
(25) —$C_{1-6}$ alkyl-aryl
(26) HetB,
(27) —$C_{1-6}$ alkyl-HetB,
(28) HetC, or
(29) —$C_{1-6}$ alkyl-HetC,
wherein
HetB is a 5- or 6-membered saturated or mono-unsaturated ring containing from 1 to 4 heteroatoms independently selected from N, O and S, wherein the ring is optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, oxo, —C(=O)—$C_{1-6}$ alkyl, —C(=O)—$C_{1-6}$ haloalkyl, or —$C_{1-6}$ alkyl—$C_{3-8}$ cycloalkyl; and HetC is a 5- or 6-membered heteroaromatic ring containing from 1 to 4 heteroatoms independently selected from N, O and S, wherein the heteroaromatic ring is optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, or oxo;

each aryl is independently phenyl or naphthyl;
each $R^a$ and $R^b$ is independently —H or —$C_{1-6}$ alkyl;
each $R^c$ is independently a —$C_{1-6}$ alkyl;
$R^d$ is a —$C_{1-6}$ alkyl, allyl, or benzyl; and
each n is independently an integer equal to 0, 1 or 2.

2. The compound according to claim 1, or a pharmaceutically acceptable salt thereof, wherein $R^1$ is —$(CH_2)_{1-4}$-phenyl, wherein the phenyl is optionally substituted with from 1 to 3 substituents each of which is independently
- (1) —$C_{1-4}$ alkyl, optionally mono-substituted with —OH, —O—$C_{1-4}$ alkyl, —O—$C_{1-4}$ haloalkyl, —CN, —N($R^aR^b$), —C(=O)N($R^aR^b$), —C(=O)$R^a$, —$CO_2R^c$, —S(O)$_nR^c$, or —$SO_2$N($R^aR^b$),
- (2) —O—$C_{1-4}$ alkyl,
- (3) —$C_{1-4}$ haloalkyl,
- (4) —O—$C_{1-4}$ haloalkyl,
- (5) —OH,
- (6) halo,
- (7) —CN,
- (8) —$NO_2$,
- (9) —N($R^aR^b$),
- (10) —$SR^c$,
- (11) —S(=O)$R^c$,
- (12) —$SO_2R^c$,
- (13) —N($R^a$)$SO_2R^c$,
- (14) —$SO_2$N($R^aR^b$),
- (15) —N($R^a$)C(=O)$R^b$,
- (16) —N($R^a$)$CO_2R^c$, or
- (17) phenyl.

3. The compound according to claim 2, or a pharmaceutically acceptable salt thereof, wherein $R^1$ is:

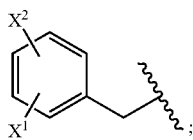

wherein $X^1$ and $X^2$ are each independently
- (1) —H,
- (2) methyl,
- (3) ethyl,
- (4) methoxy,
- (5) ethoxy,
- (6) —$CF_3$,
- (7) fluoro,
- (8) bromo,
- (9) chloro,
- (10) —CN,
- (11) —S—$CH_3$, or
- (12) phenyl.

4. The compound according to claim 3, or a pharmaceutically acceptable salt thereof, wherein $R^1$ is 4-fluorobenzyl.

5. The compound according to claim 1, or a pharmaceutically acceptable salt thereof, wherein
$R^2$ is —H or —$C_{1-4}$ alkyl;
$R^3$ is —H or —$C_{1-4}$ alkyl; and
$R^4$ is:
- (1) —H,
- (2) —$C_{1-4}$ alkyl optionally substituted with one of —OH, —O—$C_{1-4}$ alkyl, —O—$C_{1-4}$ haloalkyl, —CN, —N($R^aR^b$), —C(=O)N($R^aR^b$), —C(=O)$R^a$, —$CO_2R^c$, —S(O)$_nR^c$, —$SO_2$N($R^aR^b$), —N($R^a$)—C($R^b$)=O, —N($R^a$)$SO_2R^b$, or —N($R^a$)$SO_2$N($R^aR^b$),
- (3) —C(=O)N($R^aR^b$),
- (4) —$R^k$,
- (5) —$C_{1-4}$ alkyl substituted with $R^k$,
- (6) —$C_{1-4}$ alkyl-O—$R^k$, or
- (7) —$C_{1-4}$ alkyl-O—$C_{1-4}$ alkyl-$R^k$.

6. The compound according to claim 1, or a pharmaceutically acceptable salt thereof, wherein $R^5$ is:
- (1) —H,
- (2) —$C_{1-4}$ alkyl,
- (3) —$C_{1-4}$ alkyl-N($R^aR^b$),
- (4) —$C_{1-4}$ alkyl-C(=O)N($R^aR^b$),
- (5) —$C_{1-4}$ alkyl-$SO_2$N($R^aR^b$)
- (6) —$C_{1-4}$ haloalkyl,
- (7) halo,
- (8) —CN,
- (9) aryl
- (10) —$C_{1-4}$ alkyl-aryl
- (11) HetB,
- (12) —$C_{1-4}$ alkyl-HetB,
- (13) HetC, or
- (14) —$C_{1-4}$ alkyl-HetC, wherein
HetB is a 5- or 6-membered saturated ring containing a total of from 1 to 4 heteroatoms independently selected from 1 to 4 N atoms, from 0 to 2 O atoms, and from 0 to 2 S atoms, wherein the saturated ring is optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, oxo, —C(=O)—$C_{1-4}$ alkyl, —C(=O)—$C_{1-4}$ haloalkyl, or —$C_{1-4}$ alkyl-$C_{3-6}$ cycloalkyl; and HetC is a 5- or 6-membered heteroaromatic ring containing a total of from 1 to 4 heteroatoms independently selected from 1 to 4 N atoms, from 0 to 2 O atoms, and from 0 to 2 S atoms, wherein the heteroaromatic ring is optionally substituted with from 1 to 3 substituents each of which is independently —$C_{1-4}$ alkyl, —$C_{1-4}$ haloalkyl, —O—$C_{1-4}$ alkyl, —O—$C_{1-4}$ haloalkyl, or oxo.

7. The compound according to claim 6, or a pharmaceutically acceptable salt thereof, wherein $R^5$ is:
- (1) —H,
- (2) —$C_{1-4}$ alkyl,
- (3) —$C_{1-4}$ alkyl-N($R^aR^b$),
- (4) halo,
- (5) —CN, or
- (6) —$C_{1-4}$ alkyl-HetB;

wherein
HetB is a 5- or 6-membered saturated ring containing 1 or 2 N atoms and carbon atoms, wherein the saturated ring is optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, oxo, —C(=O)—$C_{1-4}$ alkyl, —C(=O)—$C_{1-4}$ haloalkyl, or —$C_{1-4}$ alkyl-$C_{3-6}$ cycloalkyl.

8. A compound of Formula (II), or a pharmaceutically acceptable salt thereof:

(II)

wherein:
X$^{1'}$ and X$^{2'}$ are each independently:
(1) —H,
(2) C$_{1-4}$ alkyl,
(2) —O—C$_{1-4}$ alkyl,
(3) —C$_{1-4}$ haloalkyl,
(4) —O—C$_{1-4}$ haloalkyl,
(5) halo,
(6) —CN,
(7) —S—C$_{1-4}$ alkyl, or
(8) phenyl;
R$^{2'}$ is —H or —C$_{1-4}$ alkyl;
R$^{3'}$ is —H or —C$_{1-4}$ alkyl;
R$^{4'}$ is:
(1) —H,
(2) —C$_{1-4}$ alkyl optionally substituted with one of —OH, —N(R$^{a'}$R$^{b'}$), or —C(=O)N(R$^{a'}$R$^{b'}$),
(4) —(CH$_2$)$_{1-3}$—R$^{k'}$,
(5) —(CH$_2$)$_{1-3}$—O—R$^{k'}$, or
(6) —(CH$_2$)$_{1-3}$—O—(CH$_2$)$_{1-3}$—R$^{k'}$;
wherein R$^{k'}$ is:
(i) phenyl, which is optionally substituted with from 1 to 3 substituents each of which is independently —C$_{1-4}$ alkyl, —O—C$_{1-4}$ alkyl, —C$_{1-4}$ haloalkyl, —O—C$_{1-4}$ haloalkyl, or halo; or
(ii) HetD, wherein HetD is a 5- or 6-membered saturated ring containing 1 or 2 N atoms, 0 or 1 S atoms, and a balance of carbon atoms, wherein the saturated ring is optionally substituted with from 1 to 4 substituents each of which is independently halo, —C$_{1-4}$ alkyl, —C$_{1-4}$ haloalkyl, —O—C$_{1-4}$ alkyl, —O—C$_{1-4}$ haloalkyl, or oxo;
R$^{5'}$ is:
(1) —H,
(2) —C$_{1-4}$ alkyl,
(3) —C$_{1-4}$ alkyl-N(R$^{a'}$R$^{b'}$),
(4) halo,
(5) —CN, or
(6) —(CH$_2$)$_{1-3}$-HetB;
wherein
HetB is a 5- or 6-membered saturated ring containing 1 or 2 N atoms, zero or 1 O atom, zero or 1 S atom, and a balance of carbon atoms, wherein the saturated ring is optionally substituted with from 1 to 4 substituents each of which is independently halogen, —C$_{1-4}$ alkyl, —C$_{1-4}$ haloalkyl, —O—C$_{1-4}$, alkyl, —O—C$_{1-4}$ haloalkyl, oxo, —C(=O)—C$_{1-4}$ alkyl, —C(=O)—C$_{1-4}$ haloalkyl, or —C$_{1-4}$ alkyl-C$_{3-6}$ cycloalkyl;
R$^{6'}$ is —H or methyl;
each R$^{a'}$ and R$^{b'}$ is independently —H or —C$_{1-4}$ alkyl; and
R$^{d'}$ is —C$_{1-4}$ alkyl, allyl, or benzyl.

9. A compound according to claim 8, or a pharmaceutically acceptable salt thereof, wherein:
wherein X$^{1'}$ and X$^{2'}$ are each independently:
(1) —H,
(2) methyl,
(2) —OCH$_3$,
(3) —CF$_3$,
(4) —O—CF$_3$,
(5) chloro,
(6) fluoro,
(7) bromo;
(6) —CN,
(7) —S—CH$_3$, or
(8) phenyl;
R$^{2'}$ is —H or methyl;
R$^{3'}$ is —H or methyl;
R$^{4'}$ is:
(1) —H,
(2) methyl,
(3) —CH$_2$OH,
(3) —C(=O)N(CH$_3$)$_2$,
(4) —CH$_2$—R$^{k'}$, or
(5) —CH$_2$—O—CH$_2$R$^{k'}$;
wherein R$^{k'}$ is:
(i) phenyl, which is optionally substituted with from 1 to 3 substituents each of which is independently —CH$_3$, —OCH$_3$, —CF$_3$, —OCF$_3$, chloro, bromo or fluoro; or
(ii) HetD, wherein HetD is a 5- or 6-membered saturated ring containing 1 or 2 N atoms, 0 or 1 S atoms, and a balance of carbon atoms, wherein the saturated ring is optionally substituted with from 1 to 4 substituents each of which is independently chloro, bromo, fluoro, —CH$_3$, —CF$_3$, —OCH$_3$, —OCF$_3$, or oxo;
R$^{5'}$ is:
(1) —H,
(2) methyl,
(3) —(CH$_2$)$_{1-2}$—N(CH$_3$)$_2$,
(4) fluoro,
(5) bromo,
(6) iodo,
(7) —CN, or
(8) —CH$_2$-HetB;
wherein
HetB is a 5- or 6-membered saturated ring containing 1 or 2 N atoms, zero or 1 O atom, zero or 1 S atom, and a balance of carbon atoms, wherein the saturated ring is optionally substituted with from 1 to 4 substituents each of which is independently chloro, bromo, fluoro, —CH$_3$, —CF$_3$, —OCH$_3$, —OCF$_3$, oxo, —C(=O)—CH$_3$, —C(=O)—CF$_3$, or —CH$_2$-cyclopropyl; and
R6' is —H or methyl.

10. The compound according to claim 8, which is a compound of Formula (IIa), or a pharmaceutically acceptable salt thereof:

(IIa)

wherein:

X$^{1'}$ and X$^{2'}$ are each independently:
(1) —H,
(2) C$_{1-4}$ alkyl,
(2) —O—C$_{1-4}$ alkyl,
(3) —C$_{1-4}$ haloalkyl,
(4) —O—C$_{1-4}$ haloalkyl, or
(5) halo;

R$^{2'}$ is —H or —C$_{1-4}$ alkyl;
R$^{3'}$ is —H or —C$_{1-4}$ alkyl;
R$^{4'}$ is:
(1) —H,
(2) —C$_{1-4}$ alkyl optionally substituted with one of —OH, —N(R$^{a'}$R$^{b'}$), or —C(=O)N(R$^{a'}$R$^{b'}$),
(3) —C(=O)N(R$^{a'}$R$^{b'}$),
(4) —(CH$_2$)$_{1-3}$—R$^{k'}$,
(5) —(CH$_2$)$_{1-3}$—O—R$^{k'}$, or
(6) —(CH$_2$)$_{1-3}$—O—(CH$_2$)$_{1-3}$—R$^{k'}$;
wherein R$^{k'}$ is:
(i) phenyl, which is optionally substituted with from 1 to 3 substituents each of which is independently —C$_{1-4}$ alkyl, —O—C$_{1-4}$ alkyl, —C$_{1-4}$ haloalkyl, —O—C$_{1-4}$ haloalkyl, or halo; or
(ii) HetD, wherein HetD is a 5- or 6-membered saturated ring containing 1 or 2 N atoms, 0 or 1 S atoms, and a balance of carbon atoms, wherein the saturated ring is optionally substituted with from 1 to 4 substituents each of which is independently halo, —C$_{1-4}$ alkyl, —C$_{1-4}$ haloalkyl, —O—C$_{1-4}$ alkyl, —O—C$_{1-4}$ haloalkyl, or oxo;

R$^{5'}$ is:
(1) —H,
(2) —C$_{1-4}$ alkyl,
(3) —C$_{1-4}$ alkyl-N(R$^{a'}$R$^{b'}$),
(4) halo,
(5) —CN, or
(6) —(CH$_2$)$_{1-3}$-HetB;
wherein
HetB is a 5- or 6-membered saturated ring containing 1 or 2 N atoms and carbon atoms, wherein the saturated ring is optionally substituted with from 1 to 4 substituents each of which is independently halogen, —C$_{1-4}$ alkyl, —C$_{1-4}$ haloalkyl, —O—C$_{1-4}$ alkyl, —O—C$_{1-4}$ haloalkyl, or oxo; and
each R$^{a'}$ and R$^{b'}$ is independently —H or —C$_{1-4}$ alkyl.

11. The compound according to claim 8, which is a compound of Formula (III), or a pharmaceutically acceptable salt thereof:

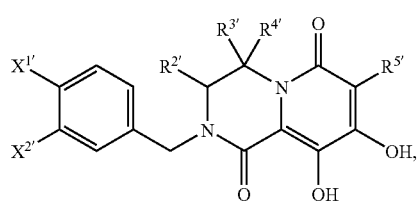

(III)

wherein:
X$^{1'}$ and X$^{2'}$ are each independently —H or halo.

12. The compound according to claim 11, or a pharmaceutically acceptable salt thereof, wherein X$^{1'}$ and X$^{2'}$ are each independently —H, fluoro, chloro, or bromo;
R$^{2'}$ is —H or methyl;
R$^{3'}$ is —H or methyl;
R$^{4'}$ is:
(1) —H,
(2) methyl,
(3) —CH$_2$OH,
(3) —C(=O)N(CH$_3$)$_2$,
(4) —CH$_2$—R$^{k'}$, or
(5) —CH$_2$—R$^{k'}$;
wherein R$^{k'}$ is:
(i) phenyl, which is optionally substituted with from 1 to 3 substituents each of which is independently —CH$_3$, —OCH$_3$, —CF$_3$, —OCF$_3$, chloro, bromo or fluoro; or
(ii) HetD, wherein HetD is a 5- or 6-membered saturated ring containing 1 or 2 N atoms, 0 or 1 S atoms, and a balance of carbon atoms, wherein the saturated ring is optionally substituted with from 1 to 4 substituents each of which is independently chloro, bromo, fluoro, —CH$_3$, —CF$_3$, —OCH$_3$, —OCF$_3$, or oxo; and R$^{5'}$ is:
(1) —H,
(2) methyl,
(3) —(CH$_2$)$_{1-2}$—N(CH$_3$)$_2$,
(4) fluoro,
(5) bromo,
(6) iodo,
(7) —CN, or
(8) —CH$_2$-HetB;
wherein
HetB is a 5- or 6-membered saturated ring containing 1 or 2 N atoms, zero or 1 O atom, zero or 1 S atom, and a balance of carbon atoms, wherein the saturated ring is optionally substituted with from 1 to 4 substituents each of which is independently chloro, bromo, fluoro, —CH$_3$, —CF$_3$, —OCH$_3$, —OCF$_3$, oxo, —C(=O)—CH$_3$, —C(=O)—CF$_3$, or —CH$_2$-cyclopropyl.

13. The compound according to claim 12, or a pharmaceutically acceptable salt thereof, wherein X$^{1'}$ is fluoro and X2' is —H.

14. A compound selected from the group consisting of:
2-benzyl-8,9-dihydroxy-3,4-dihydro-2H-pyrido[1,2-a]pyrazine-1,6-dione;
2-(4-fluorobenzyl)-8,9-dihydroxy-3,4-dihydro-2H-pyrido[1,2-a]pyrazine-1,6-dione;
2-(4-fluorobenzyl)-8,9-dihydroxy-7-methyl-3,4-dihydro-2H-pyrido[1,2-a]pyrazine-1,6-dione;
2-(4-fluorobenzyl)-8,9-dihydroxy-7-bromo-3,4-dihydro-2H-pyrido[1,2-a]pyrazine-1,6-dione;
2-(4-fluorobenzyl)-8,9-dihydroxy-7-iodo-3,4-dihydro-2H-pyrido[1,2-a]pyrazine-1,6-dione;
2-(3-chlorobenzyl)-8,9-dihydroxy-3,4-dihydro-2H-pyrido[1,2-a]pyrazine-1,6-dione;
2-(4-chlorobenzyl)-8,9-dihydroxy-3,4-dihydro-2H-pyrido[1,2-a]pyrazine-1,6-dione
2-(3,4-dichlorobenzyl)-8,9-dihydroxy-3,4-dihydro-2H-pyrido[1,2-a]pyrazine-1,6-dione;
2-(3,4-difluorobenzyl)-8,9-dihydroxy-3,4-dihydro-2H-pyrido[1,2-a]pyrazine-1,6-dione
2-(3-chloro-4-fluorobenzyl)-8,9-dihydroxy-3,4-dihydro-2H-pyrido[1,2-a]pyrazine-1,6-dione
2-(4-fluorobenzyl)-8,9-dihydroxy-7-(piperidin-1-ylmethyl)-3,4-dihydro-2H-pyrido[1,2-a]pyrazine-1,6-dione;
2-(3-chloro-4-fluorobenzyl)-8,9-dihydroxy-7-(piperidin-1-ylmethyl)-3,4-dihydro-2H-pyrido[1,2-a]pyrazine1,6-dione;

2-(4-fluorobenzyl)-8,9-dihydroxy-7-[(dimethylamino)methyl]-3,4-dihydro-2H-pyrido[1,2-a]pyrazine-1,6-dione;

2-(4-fluorobenzyl)-8,9-dihydroxy-2H-pyrido[1,2-a]pyrazine-1,6-dione 2-benzyl-8,9-dihydroxy-2H-pyrido[1,2-a]pyrazine-1,6-dione;

2-(4-fluorobenzyl)-8,9-dihydroxy-4-methyl-3,4-dihydro-2H-pyrido[1,2-a]pyrazine-1,6-dione 2-(4-fluorobenzyl)-8,9-dihydroxy-4,4-dimethyl-3,4-dihydro-2H-pyrido[1,2-a]pyrazine-1,6-dione;

2-(4-fluorobenzyl)-8,9-dihydroxy-3-methyl-3,4-dihydro-2H-pyrido[1,2-a]pyrazine-1,6-dione;

2-(4-fluorobenzyl)-8,9-dihydroxy-1,6-dioxo-1,3,4,6-tetrahydro-2H-pyrido[1,2-a]-pyrazine-7-carbonitrile;

2-(4-fluorobenzyl)-8,9-dihydroxy-7-[(4-methyl-3-oxopiperazin-1-yl)methyl]-3,4-dihydro-2H-pyrido[1,2-a]pyrazine-1,6-dione;

2-(4-fluorobenzyl)-8,9-dihydroxy-7-[(3-oxopiperazin-1-yl)methyl]-3,4-dihydro-2H-pyrido[1,2-a]pyrazine-1,6-dione;

4-[(benzyloxy)methyl]-2-(4-fluorobenzyl)-8,9-dihydroxy-3,4-dihydro-2H-pyrido[1,2-a]pyrazine-1,6-dione;

4-(hydroxymethyl-2-(4-flurobenzyl)-8,9-dihydroxy-3,4-dihydro-2H-pyrido[1,2-a]pyrazine-1,6-dione;

4-[(1,1-dioxido-1,2-thiazinan-2-yl)methyl]-2-(4-flurobenzyl)-8,9-dihydroxy-3,4-dihydro-2H-pyrido[1,2-a]pyrazine-1,6-dione;

7-[(1-acetylpiperidin-4-yl)methyl]-2-(4-fluorobenzyl)-8,9-dihydroxy-3,4-dihydro-2H-pyrido[1,2-a]pyrazine-1,6-dione;

2-(4-fluorobenzyl)-8,9-dihydroxy-7-{[1-(trifluoroacetyl)piperidin-4-yl]methyl}-3,4-dihydro-2H-pyrido[1,2-a]pyrazine-1,6-dione;

7-{[1-(cyclopropylmethyl)piperidin-3-yl]methyl}-2-(4-fluorobenzyl)-8,9-dihydroxy-3,4-dihydro-2H-pyrido[1,2-a]pyrazine-1,6-dione;

7-[(1-acetylpiperidin-3-yl)methyl]-2-(4-fluorobenzyl)-8,9-dihydroxy-3,4-dihydro-2H-pyrido[1,2-a]pyrazine-1,6-dione;

7-[(1-acetylpiperidin-2-yl)methyl]-2-(4-fluorobenzyl)-8,9-dihydroxy-3,4-dihydro-2H-pyrido[1,2-a]pyrazine-1,6-dione;

7-{[1-(cyclopropylmethyl)piperidin-2-yl]methyl}-2-(4-fluorobenzyl)-8,9-dihydroxy-3,4-dihydro-2H-pyrido[1,2-a]pyrazine-1,6-dione;

2-(3-cyanobenzyl)-8,9-dihydroxy-3,4-dihydro-2H-pyrido[1,2-a]pyrazine-1,6-dione 2-(biphenyl-3-ylmethyl)-8,9-dihydroxy-3,4-dihydro-2H-pyrido[1,2-a]pyrazine-1,6-dione 2-[1-(4-fluorophenyl)ethyl]-8,9-dihydroxy-3,4-dihydro-2H-pyrido[1,2-a]pyrazine-1,6-dione;

and pharmaceutically acceptable salts thereof.

15. A pharmaceutical composition comprising a compound according to claim 1, or a pharmaceutically acceptable salt thereof, and a pharmaceutically acceptable carrier.

16. A method for treating infection by HIV or for treating AIDS in a subject in need thereof which comprises administering to the subject a therapeutically effective amount of the compound according to claim 1, or a pharmaceutically acceptable salt thereof.

17. A combination useful for treating infection by HIV, or for treating AIDS, which is a therapeutically effective amount of a compound according to claim 1, or a pharmaceutically acceptable salt thereof, and a therapeutically effective amount of an HIV infection/AIDS antiviral agent selected from the group consisting of HIV protease inhibitors, non-nucleoside HIV reverse transcriptase inhibitors and nucleoside HIV reverse transcriptase inhibitors.

* * * * *